US012685879B1

(12) United States Patent
Rahimian

(10) Patent No.: US 12,685,879 B1
(45) Date of Patent: **\*Jul. 21, 2026**

(54) TREATING CANCER USING INTENSITY-MODULATED BRACHYTHERAPY

(71) Applicant: Voxel Rad, Ltd., Irvine, CA (US)

(72) Inventor: Javad Rahimian, Irvine, CA (US)

(73) Assignee: Voxel Rad, Ltd., Irvine, CA (US)

( * ) Notice: Subject to any disclaimer, the term of this patent is extended or adjusted under 35 U.S.C. 154(b) by 1151 days.

This patent is subject to a terminal disclaimer.

(21) Appl. No.: 17/351,013

(22) Filed: Jun. 17, 2021

Related U.S. Application Data

(60) Provisional application No. 63/041,037, filed on Jun. 18, 2020.

(51) Int. Cl.
*A61N 5/10* (2006.01)
*A61B 1/00* (2006.01)
(Continued)

(52) U.S. Cl.
CPC ........ *A61N 5/1016* (2013.01); *A61B 1/00165* (2013.01); *A61B 1/303* (2013.01);
(Continued)

(58) Field of Classification Search
CPC .......... A61N 5/1016; A61N 2005/1003; A61B 1/00165; A61B 1/303; A61B 8/12; A61B 1/00154; A61M 25/0026
(Continued)

(56) References Cited

U.S. PATENT DOCUMENTS 2,959,166 A    11/1960    Clayton
3,807,386 A    4/1974    Rocoplan et al.
(Continued)

FOREIGN PATENT DOCUMENTS

EP    0335022 A1    10/1989
EP    1004272 A    5/2000
(Continued)

OTHER PUBLICATIONS

"ACR Standard for the Performance of Stereotactic Radiosurgery: Practice Guideline", American College of Radiology, 2002, 559-563.

(Continued)

*Primary Examiner* — Sunita Reddy
(74) *Attorney, Agent, or Firm* — Knobbe, Martens Olson & Bear, LLP

(57) ABSTRACT

Systems and methods are provided for treating cervical and/or uterine cancers in brachytherapy with an intracavitary brachytherapy applicator. The system comprises a tandem adapted for insertion into a cervix of a patient. An ovoid assembly comprises first and second inflatable ovoids and an ovoid support mechanism. The first and second inflatable ovoids are adapted for insertion within fornices of a patient. First and second retractors are adapted to be coupled to the ovoid assembly. The first retractor is adapted to be positioned to retract the bladder of a patient during treatment. The second retractor is adapted to be positioned to retract the rectum of a patient during treatment. The tandem and the first and second inflatable ovoids are adapted to be coupled to a radioactive source to deliver an implant radiation dose suitable for cancer treatment at a cancerous cervical treatment site in a patient.

21 Claims, 33 Drawing Sheets

(51) Int. Cl.
  *A61B 1/303* (2006.01)
  *A61B 8/12* (2006.01)
  *A61M 25/00* (2006.01)

(52) U.S. Cl.
  CPC ............ *A61B 8/12* (2013.01); *A61B 1/00154*
      (2013.01); *A61M 25/0026* (2013.01); *A61N*
                            *2005/1003* (2013.01)

(58) Field of Classification Search
  USPC ........................................................ 600/3–8
  See application file for complete search history.

(56) References Cited

U.S. PATENT DOCUMENTS

| | | | |
|---|---|---|---|
| 4,132,896 A | 1/1979 | Klotz et al. |
| 4,237,901 A | 12/1980 | Taenzer |
| 4,249,106 A | 2/1981 | Maruyama et al. |
| 4,292,960 A | 10/1981 | Paglione |
| 4,294,264 A | 10/1981 | Fischell et al. |
| 4,331,131 A | 5/1982 | Kumar |
| 4,583,538 A | 4/1986 | Onik et al. |
| 5,012,357 A | 4/1991 | Schoeppel et al. |
| 5,067,981 A | 11/1991 | Hooykaas |
| 5,197,476 A | 3/1993 | Nowacki et al. |
| 5,207,223 A | 5/1993 | Adler |
| 5,222,499 A | 6/1993 | Allen et al. |
| 5,278,886 A | 1/1994 | Kobiki et al. |
| 5,394,875 A | 3/1995 | Lewis et al. |
| 5,397,329 A | 3/1995 | Allen |
| 5,411,026 A | 5/1995 | Carol |
| 5,427,097 A | 6/1995 | Depp |
| 5,446,548 A | 8/1995 | Gerig et al. |
| 5,447,154 A | 9/1995 | Cinquin |
| 5,537,452 A | 7/1996 | Shepherd et al. |
| 5,562,594 A | 10/1996 | Weeks |
| 5,588,430 A | 12/1996 | Bova et al. |
| 5,622,187 A | 4/1997 | Carol |
| 5,628,315 A | 5/1997 | Vilsmeier et al. |
| 5,727,554 A | 3/1998 | Kalend et al. |
| 5,748,700 A | 5/1998 | Shepherd et al. |
| 5,769,861 A | 6/1998 | Vilsmeier |
| 5,784,431 A | 7/1998 | Kalend et al. |
| 5,797,849 A | 8/1998 | Vesely et al. |
| 5,943,719 A | 8/1999 | Feldman et al. |
| 5,967,981 A | 10/1999 | Watrous |
| 5,971,997 A | 10/1999 | Guthrie et al. |
| 6,006,126 A | 12/1999 | Cosman |
| 6,019,724 A | 2/2000 | Gronningsaeter et al. |
| 6,031,888 A | 2/2000 | Ivan et al. |
| 6,035,228 A | 3/2000 | Yanof et al. |
| 6,052,611 A | 4/2000 | Yanof et al. |
| 6,076,005 A | 6/2000 | Sontag et al. |
| 6,083,170 A | 7/2000 | Ben-Haim |
| 6,120,453 A | 9/2000 | Sharp |
| 6,144,875 A | 11/2000 | Schweikard et al. |
| 6,149,592 A | 11/2000 | Yanof et al. |
| 6,246,898 B1 | 6/2001 | Vesely et al. |
| 6,256,372 B1 | 7/2001 | Aufrichtig et al. |
| 6,275,721 B1 | 8/2001 | Darrow et al. |
| 6,285,902 B1 | 9/2001 | Kienzle, III et al. |
| 6,301,495 B1 | 10/2001 | Gueziec et al. |
| 6,307,914 B1 | 10/2001 | Kunieda et al. |
| 6,312,375 B1 | 11/2001 | Montebello |
| 6,314,312 B1 | 11/2001 | Wessels et al. |
| 6,380,958 B1 | 4/2002 | Guendel et al. |
| 6,405,072 B1 | 6/2002 | Cosman |
| 6,416,510 B1 | 7/2002 | Altman et al. |
| 6,464,648 B1 | 10/2002 | Nakamura |
| 6,470,207 B1 | 10/2002 | Simon et al. |
| 6,473,634 B1 | 10/2002 | Barni |
| 6,482,142 B1 | 11/2002 | Winkler et al. |
| 6,484,118 B1 | 11/2002 | Govari et al. |
| 6,501,981 B1 | 12/2002 | Schweikard et al. |
| 6,681,129 B2 | 1/2004 | Matsuzaki et al. |

| | | | |
|---|---|---|---|
| 6,699,171 B2 | 3/2004 | Harmon |
| 6,778,850 B1 | 8/2004 | Adler |
| 7,318,805 B2 | 1/2008 | Schweikard et al. |
| 7,534,202 B2 | 5/2009 | Eng |
| 7,666,130 B2 | 2/2010 | Mick |
| 7,678,040 B2 | 3/2010 | Francescatti et al. |
| 7,728,868 B2 | 6/2010 | Razzaque et al. |
| 8,218,846 B2 | 7/2012 | Trumer et al. |
| 8,295,435 B2 | 10/2012 | Wang et al. |
| 8,346,344 B2 | 1/2013 | Pfister et al. |
| 8,494,246 B2 | 7/2013 | Trumer et al. |
| 8,500,618 B2 | 8/2013 | Isham |
| 8,758,263 B1 | 6/2014 | Rahimian et al. |
| 9,295,491 B2 | 3/2016 | Rahimian |
| 9,295,856 B2 | 3/2016 | Rahimian |
| 9,649,168 B2 | 5/2017 | Rahimian et al. |
| 10,016,619 B2 | 7/2018 | Rahimian |
| 10,391,221 B2 | 8/2019 | Rahimian et al. |
| 10,806,339 B2 | 10/2020 | Rahimian |
| 11,491,346 B2 | 11/2022 | Rahimian |
| 11,577,049 B2 | 2/2023 | Rahimian et al. |
| 11,617,503 B2 | 4/2023 | Rahamian et al. |
| 12,137,882 B2 | 11/2024 | Rahamian et al. |
| 2002/0032453 A1 | 3/2002 | Cosman |
| 2002/0065461 A1 | 5/2002 | Cosman |
| 2002/0154728 A1 | 10/2002 | Morita et al. |
| 2003/0179308 A1 | 9/2003 | Zamorano et al. |
| 2004/0006305 A1 | 1/2004 | Hebert |
| 2004/0097806 A1 | 5/2004 | Hunter et al. |
| 2005/0004580 A1 | 1/2005 | Jokiniemi et al. |
| 2005/0054910 A1 | 3/2005 | Tremblay et al. |
| 2006/0116546 A1 | 6/2006 | Eng |
| 2006/0235260 A1 | 10/2006 | Mourtada et al. |
| 2007/0083193 A1 | 4/2007 | Werneth et al. |
| 2007/0185396 A1 | 8/2007 | Zan |
| 2007/0225553 A1 | 9/2007 | Shahidi |
| 2008/0021297 A1 | 1/2008 | Boosten |
| 2008/0043901 A1 | 2/2008 | Maschke |
| 2008/0064916 A1 | 3/2008 | Mick |
| 2008/0118135 A1 | 5/2008 | Averbuch et al. |
| 2008/0167514 A1 | 7/2008 | Lim et al. |
| 2008/0171934 A1 | 7/2008 | Greenan et al. |
| 2009/0069672 A1 | 3/2009 | Pfister et al. |
| 2009/0088756 A1 | 4/2009 | Anderson |
| 2009/0129545 A1 | 5/2009 | Adler et al. |
| 2009/0171157 A1 | 7/2009 | Diederich et al. |
| 2009/0198093 A1 | 8/2009 | Meissner et al. |
| 2009/0216221 A1 | 8/2009 | Davis et al. |
| 2009/0234176 A1 | 9/2009 | Lebovic et al. |
| 2009/0312629 A1 | 12/2009 | Razzaque et al. |
| 2010/0048977 A1 | 2/2010 | Sing et al. |
| 2010/0063387 A1 | 3/2010 | Timinger |
| 2010/0063514 A1 | 3/2010 | Maschke |
| 2010/0069878 A1 | 3/2010 | Parsai et al. |
| 2010/0094081 A1 | 4/2010 | Rothe et al. |
| 2010/0268067 A1 | 10/2010 | Razzaque et al. |
| 2010/0274311 A1 | 10/2010 | Vaidyanathan |
| 2010/0286465 A1 | 11/2010 | Benson |
| 2010/0317962 A1 | 12/2010 | Jenkins et al. |
| 2011/0130651 A1 | 6/2011 | Chen et al. |
| 2013/0317276 A1 | 11/2013 | D'Andrea |
| 2019/0070434 A1* | 3/2019 | Rahimian ............. A61B 17/42 |
| 2021/0093179 A1 | 4/2021 | Rahimian et al. |
| 2023/0085476 A1 | 3/2023 | Rahimian et al. |
| 2023/0233071 A1 | 7/2023 | Rahamian et al. |
| 2023/0248942 A1 | 8/2023 | Rahimian et al. |
| 2025/0134367 A1 | 5/2025 | Rahimian et al. |

FOREIGN PATENT DOCUMENTS

| | | | |
|---|---|---|---|
| EP | 1695740 | 4/2014 |
| JP | 62-206798 | 9/1987 |
| JP | 5-188199 | 7/1993 |
| JP | 6-502330 | 3/1994 |
| JP | 6-181918 | 7/1994 |
| JP | 8112272 | 5/1996 |
| JP | A-10-201863 | 8/1998 |
| JP | 11-019082 | 1/1999 |
| JP | 2000-201922 | 7/2000 |

(56)                References Cited

FOREIGN PATENT DOCUMENTS

| JP | 2000-217810 | 8/2000 | | |
| JP | 2008023347 | 2/2008 | | |
| JP | 4718551 | 7/2011 | | |
| WO | WO 92/06644 | 4/1992 | | |
| WO | WO 97/40766 | 11/1997 | | |
| WO | WO 00/07669 | 2/2000 | | |
| WO | WO 03/034705 A2 | 4/2003 | | |
| WO | WO 2011/011731 | 1/2011 | | |
| WO | WO-2015023307 A1 * | 2/2015 | ........... | A61N 5/1016 |

OTHER PUBLICATIONS

Brommeland, "Mechanical accuracy of a new stereotactic guide", Acta Neurochir (Wien). 2000, 142(4), 449-54.

Chen et al., "Control of brain metastases using frameless image-guided radiosurgery", Neurosurgical Focus, Dec. 2009; 27(6): 1-7.

Chen et al., "Contemporary methods of radiosurgery treatment with the Novalis linear accelerator system", Neurosurgical Focus, Dec. 2007; 23(6): 1-10.

Chen et al., "Treatment of trigeminal neuralgia with linear accelerator radiosurgery: initial results", Journal of Neurosurgery, vol. 101, Supplement 3 101:346-26, 2004.

Cleary, "Tracking Systems", Georgetown University Medical Center, Washington, DC, MICCAI 2009. www.isis.georgetown.edu/CAIMR/ . . . /Cleary%20tracking%20systems.pdf.

Coste-Manière, "Robotic whole body stereotactic radiosurgery: clinical advantages of the CyberKnife® integrated system", The International Journal of Medical Robotics+Computer Assisted Surgery, 2005, www.roboticpublications.com, pp. 28-39.

Dorward et al., "The advantages of frameless stereotactic biopsy over frame-based biopsy", Br J Neurosurg, Apr. 2002, 16(2), 110-18.

Drzymala et al., "Assurance of high quality linac-based stereotactic radiosurgery", International Journal of Radiation Oncology Biology Physics. Sep. 30, 1994; 30(2): 459-472.

Dukkipati et al., "Pulmonary Vein Isolation Using a Visually Guided Laser Balloon Catheter: The First 200-Patient Multicenter Clinical Experience", Circ Arrhythm Electrophysiol, 2013, No. 6, 467-142; originally published online Apr. 4, 2013.

Dukkipati et. al. Visual Balloon-Guided Point-by-Point Ablation: Reliable, Reproducible, an Persistent Pulmonary Vein Isolation, http://circep.ahajournals.org/content/3/3/266.full; and William W.B. Chik, et. al. In Vivo Evaluation of Virtual Electrode Mapping and Ablation Utilizing a Direct Endocardial Visualization Ablation Catheter. Journal of Cardiovascular Electrophysiology vol. 23, No. 1,pp. 88-96, Jan. 2012).

Dukkipati et al., "The Durability of Pulmonary Vein Isolation Using the Visually Guided Laser Balloon Catheter: Multicenter Results of Pulmonary Vein Remapping Studies", Heart Rhythm Society, pp. 919-925, 2012.

Dupuy et al., "Accuracy of CT-guided needle biopsy of musculoskeletal neoplasms", AJR Am J Roentgenol. Sep. 1998., 171(3):759-62.

http://en.wikipedia.org/wiki/Brain_pacemaker, in 2 pages, Jan. 26, 2011.

Everly et al., "Intracardiac acoustic radiation force: A novel imaging method for intraprocedural evaluation of radiofrequency ablation lesions", Heart Rhythm, 2012, 9:1855-1862.

Examination Report Issued in European Patent Application No. 01 970 945.0, dated Jan. 16, 2007, 7 pages.

Examination Report Issued in European Patent Application No. 01 970 945.0, dated Feb. 23, 2010, 6 pages.

International Search Report in International PCT Application No. PCT/EP2010/043121, dated Apr. 20, 2011 issued in the name of Voxel Rad, Ltd in 10 pages.

Khan, "Physics of Radiation Therapy", 3rd ed. Lippincott Williams & Wilkins, 2003, Chapter 21: 507-520.

Larsson et al.,"Irradiation of Small Structures Through the Intact Skull", Acta Oncologica, 1974, vol. 13, No. 6, pp. 512-534.

Leksell, "The stereotactic method and radiosurgery of the brain", Acta Chirurgica Scandinavica. 1951; 102:316-319.

Leksell, "Cerebral radiosurgery", Acta Chir Scandinavica. 134:585-595, 1968.

Lis et al., "Percutaneous CT-Guided Biopsy of Osseous Lesion of the Spine in Patients with Known or Suspected Malignancy", American Journal of Neuroradiology, 25:1583-1588, Oct. 2004.

Lutz et al., "A system for stereotactic radiosurgery with a linear accelerator", International Journal of Radiation Oncology Biology Physics, 1988, 14(2):373-381.

Mack et al., "Quality assurance in stereotactic space. A system test for verifying the accuracy of aim in radiosurgery", Medical Physics, Apr. 29, 2002, (4): 561-568.

Magjarevic et al., "IFMBE Proceedings", vol. 14/1 to 14/6, World Congress on Medical Physics and Biomedical Engineering 2006, held Aug. 27, 2006-Sep. 1, 2006, Table of Contents, dated 2007, in 145 pages.

Malatesta et al. "Dosimetric, mechanical, and geometric verification of conformal dynamic arc treatment", Journal of Applied clinical Medical Physics, 2003, 4(3):195-203.

Malhotra et al., "Duplicating a tandem and ovoids distribution with intensity-modulated radiotherapy;|a feasibility study", Journal of Applied Clinical Medical Physics, vol. 8, No. 3, Summer of 2007 in 8 pages.

Medical Physics, AAPM Annual Meeting Issue, Imaging Physics, dated Jun. 1999, vol. 26, No. 6, in 3 pages.

Metzner et al., "One-Year Clinical Outcome After Pulmonary Vein Isolation Using the Novel Endoscopic Ablation System in Patients with Paroxysmal Atrial Fibrillation", Asklepios Klinik St. Georg, Department of Cardiology, Hamburg, Germany, pp. 988-993, 2011.

Metzner et al., "The Influence of Varying Energy Settings on Efficacy and Safety of Endoscopic Pulmonary Vein Isolation", Departments of Cardiology and Internal Medicine, Asklepios Klinik St. Georg, Hamburg, Germany, pp. 1380-1385, 2012.

Minohara et al., "Respiratory Gated Irradiation System for Heavy-Ion Radiotherapy", International Journal of Radiation: Oncology Biology Physics, Pergamon Press, US, vol. 47, No. 4, Jul. 1, 2000, ISSN: 0360-3016.

Miyazaki, et al., "Non-contrast-enhanced MR angiography using 3D ECG-synchronized half-Fourier fast spin echo." Journal of Magnetic Resonance Imaging, vol. 12, Issue 5, Nov. 2000, pp. 776-783.

Park et al., "Frameless Stereotactic Biopsy for the Brain Tumor", IFMBE Proceedings vol. 14/5, vol. 5, Track 17 3143, 2007 in 3 pages.

Rahimian et al., "Frame Based and Frameless Precision of BrainLab Novalis © Stereotactic Radiosurgery System", Submitted for Publication, 2009.

Rahimian et al., "Geometrical accuracy of the Novalis stereotactic radiosurgery system for trigeminal neuralgia", J Neurosurg, (Suppl 3), 101:351-355, 2004.

Rahimian et al., "Geometric Accuracy of Frameless Based Image Guided Stereotactic Radiosurgery of Trigeminal Neuralgia Using BrainLab's Exactrac 6-D Robotic System", International Journal of Radiation Oncology Biology Physics, 75(3): S676, ASTRO 2009.

Rahimian et al., "Geometric Accuracy of Novalis Stereotactic Radiosurgery System for Trigeminal Neuralgia", J. Neurosurgery, (Suppl 3) 101: 351-355, 2004.

Rahimian et al., Frame Based and Frameless Precision of BrainLab Novalis © StereotacticRadiosurgery System:, Shaped Beam Radiosurgery, Chapter 4, A. de Salles, editor, Springer Verlag Publishers, 2011.

Ramaseshan et al., "Comprehensive quality assurance for stereotactic radiosurgery treatments", Physics in Medicine and Biology, 2003; 48:N199-N205.

Reddy, et al., "Visually-Guided Balloon Catheter Ablation of Atrial Fibrillation: Experimental Feasibility and First-in-Human Multicenter Clinical Outcome", Circulation. 2009; 120:12-20; originally published online Jun. 22, 2009.

Rodriguez et al., "Absorbed dose calculations in a brachytherapy pelvic phantom using the Monte Carlo method", Journal of Applied Clinical Medical Physics, Fall 2002, vol. 3, No. 4, pp. 285-292.

(56) References Cited

OTHER PUBLICATIONS

Ryken et al., "Initial clinical experience with frameless stereotactic radiosurgery: analysis of accuracy and feasibility", International Journal of Radiation Oncology Biology Physics, Nov. 15, 2001, vol. 51, Issue 4, pp. 1152-1158,.

Schmidt et al., "Feasibility of Circumferential Pulmonary Vein Isolation Using a Novel Endoscopic Ablation System", Circ Arrhythm Electrophysiol, 2010, 3:481-488; originally published online Jul. 24, 2010.

Supplementary European Search Report for European Patent Application No. 01 970 945.0, dated Oct. 16, 2006, 5 pages.

Supplementary European Search Report for European Patent Application No. 01 970 945.0, dated Apr. 5, 2006, 5 pages.

Supplementary Partial European Search Report, Application No. EP01970945, mailed Jun. 28, 2006.

http://www.richard-wolf.com/imaging/product-highlights/epic-3dhd-video.html.

https://superdimension.com/products/navigation-catheters/.

United States Court of Appeals for the Federal Circuit; *Hologic, Inc., Cytyc Corporation and Hologic L.P.* v *Senorx, Inc.*; Decided Feb. 24, 2011 in 5 pages.

Verellen et al. "Assessment of the uncertainties in dose delivery of a commercial system for LINAC-based stereotactic radiosurgery", International Journal of Radiation Oncolology Biology Physics, May 1, 1999, vol. 44, No. 2, 421-433.

Vinci et al., "Accuracy of cranial coplanar beam therapy using an oblique, stereoscopic x-ray image guidance system", Med. Phys., Aug. 2008, vol. 35, Issue 8, pp. 3809-3819.

Widmann G., M.D., "Image-guided surgery and medical robotics in the cranial area", Biomedical Imaging and Intervention Journal, Feb. 21, 2007, 3(1): 1-9.

Wood et al., "Artifacts, In Magnetic resonance imaging", vol. 1, 3rd ed. Mosby, Chapter 10: 215-230, 1999.

Wurm et. al., "Novalis frameless image-guided noninvasive radiosurgery: Initial experience", Neurosurgery, Vo. 62, No. 5, May 2008, pp. A11-A18.

Yeung et al., "Systematic analysis of errors in target localization and treatment delivery in Stereotactic radiosurgery (SRS)", International Journal of Radiation Oncology Biology Phys., Jan. 15, 1994, vol. 28, No. 2: 493-498.

* cited by examiner

146

150

144

110

100

116

102

122

172

114

106

170

120

112

Anterior

Rt Lateral                          Lt Lateral

Posterior

Position 1

Position 2

Position 3

Position 4

Position 5

TREATING CANCER USING INTENSITY-MODULATED BRACHYTHERAPY

CROSS-REFERENCE TO RELATED APPLICATIONS

This application claims the benefit of priority under 35 U.S.C. § 119 (e) of U.S. Provisional Application No. 63/041,037, filed Jun. 18, 2020, the entirety of this application is hereby incorporated by reference herein.

BACKGROUND

Field of the Invention

The present application relates to devices and methods for treating cancer using intensity-modulated brachytherapy (IMBT). In particular, the present application relates to devices and methods for treating various cancer sites with brachytherapy such as cervical and/or uterine, vaginal, esophagus, bronchus, lung, liver, gall bladder, and prostate cancers using multi lumen catheters.

Description of the Related Art

"Brachy" is derived from the Greek word "brachio" meaning short range, and in reference to brachytherapy is defined as "Short Range Treatment with a Radioisotope." Five years after 226Ra was discovered by Marie and Pierre Curie in Paris, Alexander Graham Bell suggested the implantation of radioactive sources directly into the tumors. That same year in 1903, two cases of facial basal cell carcinoma were treated, using 226Ra surface molds in St. Petersburg.

Brachytherapy typically offers low morbidity by delivering a high dose of ionizing radiation to the target volume, sparing surrounding healthy tissue with rapid dose fall off outside the implanted volume. Selective placement of the radioactive sources allows the dose distribution to be manipulated to match the target shape. Brachytherapy can be used in treating most areas of the body and can be used alone or in conjunction with External Beam Radiotherapy, Chemotherapy, and Surgery for management of cancer. HDR and LDR brachytherapy are well-established techniques with a long history of use in treatment of cervical and uterine cancers. The scientific principle behind this technology is that a highly radioactive source inside an afterloader passes through a transfer guide tube into an applicator implanted in the patient. The radioactive source is programmed to remain in its precise location for a given period to deliver radiation dose according to the prescription. This can be effective in treating, for example, cancers of the cervix and uterus.

One example applicator is the classical Fletcher-Suit-Delclos (FSD) brachytherapy. However, the FSD is tedious and time consuming to implant with superior dosimetry. The FSD implant procedure requires the patient to be consciously sedated or anesthetized as the procedure can be painful and lengthy with the complex design of the current available applicators requiring one to two nurses in assisting the radiation oncologist in implanting the applicator. The non-ideal geometry of the applicator placement, and the inadequate and occasionally painful placement of the vaginal packing retractor used to retract the bladder and the rectum from the plane of the implant, make the radiation dosimetry non-ideal, with high doses reaching the bladder or the rectum causing unwanted morbidities in some cases.

Accordingly, in order to keep the radiation dose within the respective tolerance doses of the organs at risk, in some cases a user lowers the dose to the tumor; thus potentially causing the cancer to reoccur. Some optimization algorithms are currently used in the HDR treatment planning systems, however these cannot and do not adequately substitute or replace a geometrically optimum implant.

In recent years many intracavitary applicators based on the FSD applicator concept have been designed, and used in the clinic, e.g., the Week, Williamson, Henschke and Mick applicators. The typical prescription requires 3 or 4 implants, one week apart, on the same patient. The traditional FSD applicator normally consists of 8-pieces assembled as the patient rests supine in the stirrup position. The current clinical procedure using FSD applicator is typically lengthy, painful, and often requires anesthetics, or conscious sedation. The problems outlined herein have made patients request alternative treatments such as surgery or use of Intensity Modulated Radiotherapy (IMRT). However, the intracavitary brachytherapy for treating cervical and uterine cancers should not be replaced with IMRT since intracavitary brachytherapy provides more conformal therapy, less integral dose, and superior sparing of the organs at risk.

SUMMARY

The present application relates to devices and methods for treating various cancer sites using brachytherapy with multi lumen catheters or applicators such as an Endoscopic multi-lumen Tandem and Inflatable Ovoids afterloading intracavitary brachytherapy applicator, or ETIO applicator. The ETIO intracavitary brachytherapy applicator with proposed multi lumen catheters can be used to treat the cancer using intensity modulated brachytherapy (IMBT) to harness the benefits of brachytherapy and maximize the dose to the tumor and minimize the dose to the organs-at-risk (OARs), thus maximizing the therapeutic ratio and lowering the morbidities due to treatment. HDR brachytherapy currently has two degrees of freedom, namely the radioactive source (i.e. Ir-192) dwell time and the dwell position with which the dose distribution can be made conformal. Described herein are devices to allow for a third degree of freedom, partially shielding the radiation exposure in a direction desired to protect an OAR using a high atomic number metal that is in some embodiments non-ferromagnetic, such as gold or tungsten, to modulate the intensity of radiation for better conformity and OAR sparing. As the radioactive source emits radiation isotropically in 360 degrees ($4\pi$) space, the radiation in the direction of an organ at risk may be blocked. There are organs such as sigmoid colon that cannot be protected when using a Fletcher-Suit-Delclos (FSD) applicator for treating cervical or uterine cancers especially in older and atrophied uteri by vaginal packing or lowering the dose with the current two degrees of freedom. However, with the novel and innovative applicator designs described herein, such as those having multi-lumens, the radiation source and one or more metal-tipped dummy wires (e.g., with gold and/or tungsten) can synchronously dwell in two or more lumens (e.g., in a central lumen with the radioactive wire). This arrangement can allow for the posterior and/or lateral lumens with the metal shielding wires to partially block the radiation and preferentially treat the patient.

Based on a patient's anatomical features and age, dosages and/or OAR location can vary dramatically. Accordingly, in certain circumstances the sigmoid colon may be very close to the tandem in such a way that cannot be easily retracted by means of packing by the radiation oncologist (FIG. 1). A dual or triple lumen (or other multi-lumen) tandem can be used. In some embodiments, a posterior lumen with an internal diameter (ID) of between about 1 mm to 2 mm can include a length and/or layer of a protective material or shielding material. The shielding material may include a solid, non-ferromagnetic, and/or high atomic number (e.g., greater than 70) material. For example, tungsten wire with atomic number 74 or gold wire with atomic number 79 may be used. The shielding material may be inserted into the lumen to shield differentially the organs located posteriorly to the tandem to protect, for example, the sigmoid colon before the treatment initiation. The half-value layer (HVL) of Ir-192 is about 3 mm of tungsten. Accordingly, using a layer that is 1 mm to 2 mm thick of tungsten may lower the dose to the organ (e.g., the sigmoid colon) by about 34% to 57% (see Table I below). A 1 mm and 2 mm diameter solid gold tipped wire shield with the half value layer of 1.44 mm for Ir-192 gamma rays may lower the dose by 38% and 62%, respectively. The recommended 2 cc tolerance doses to the sigmoid colon and bladder by the American Brachytherapy Society (ABS) are 75 Gy and 90 Gy, respectively. Thus, this shielding may be adequate to protect the sigmoid colon from high doses of radiation. Other materials and thicknesses may be used (Table I). Gold and tungsten with an atomic number of 79 and 74 are effective shielding metals for Ir-192 that can be in form of a thin wire, a rod, with round or a flat top shape to modulate the radiation intensity partially and differentially to treat the uterus and protect the more sensitive sigmoid colon or the rectum behind the uterus inaccessible to vaginal packing or our rectal balloon retractor. The gold or tungsten shielding rods can be pre-inserted manually into the posterior lumen of the tandem or ovoids or after the implant and treatment planning is done to modulate the dose posteriorly to lower the dose to the organs at risk (OARs).

4 balloons with the capability of expansion to multiple sizes through iodinated saline. To replace inadequate retraction offered by currently used vaginal packing, two additional semi-cylindrical balloons are preferably attached to the ovoid assembly for retracting the bladder and rectum to lower the radiation dose received by these organs. The applicator preferably provides a geometrically optimum implant where the tandem is positioned to bisect the ovoids, the ovoids are inflated and positioned to the largest size appropriate to fit the anatomy of the patient, and the bladder and the rectum are pushed away from a plane of the implant by one or more retractors. In some embodiments the retractors push the bladder and rectum away from a plane of the implant by at least two centimeters. The applicator implements inflatable retractors for isolating the patient's bladder and the rectum from radioactive sources, lowering the radiation dosage absorbed by these critical structures. An endoscope integrated with the tandem, in some embodiments, can provide advantages such as, for example, locating the cervical os more easily, limiting uterine perforations, sounding the uterus, and guiding the tandem through the uterine canal.

According to one method, an embodiment of the applicator is provided having a tandem and a dual ovoid assembly. The tandem may have a fiberoptic endoscope integrated with it, so the cervical os can easily be found instead of the patient being blindly poked with a speculum placed in the vaginal canal. The tandem and the collapsed balloon dual ovoid assembly can easily be inserted as a single unit into the vaginal canal. The tandem may be guided by endoscope into the cervical os and uterine canal, where the ovoids may be placed in the cervical fornices. The ovoids can comprise two balloons that are inflated with desired volumes of iodinated saline. The ovoids can conform to the cervical tumor and can provide adaptive brachytherapy. The appli-

TABLE I

| | Element | Tungsten W | Gold Au | Lead Pb | Uranium U |
|---|---|---|---|---|---|
| Atomic Number | | 74 | 79 | 82 | 92 |
| Density (gr/cc) | | 19.3 | 19.32 | 11.34 | 19.1 |
| 300 KeV | u/p | 0.3238 | 0.3744 | 0.4031 | 0.4447 |
| 400 KeV | u/p | 0.1925 | 0.218 | 0.2323 | 0.4392 |
| Ir-192 | | 0.21876 | 0.24928 | 0.26646 | 0.4403 |
| u (1/mm) | | 0.4222068 | 0.481609 | 0.30216564 | 0.840973 |
| HVL (mm) | | 1.64 | 1.44 | 2.29 | 0.82 |

| Thickness (mm) | % protection | % protection | % protection | % protection |
|---|---|---|---|---|
| 3 | 34% | 38% | 26% | 57% |
| 2 | 57% | 62% | 45% | 81% |
| 3 | 72% | 76% | 60% | 92% |
| 4 | 82% | 85% | 70% | 97% |
| 5 | 88% | 91% | 78% | 99% |
| 6 | 92% | 94% | 84% | 99% |
| 7 | 95% | 97% | 88% | 100% |
| 8 | 97% | 98% | 91% | 100% |
| 9 | 98% | 99% | 93% | 100% |
| 10 | 99% | 99% | 95% | 100% |

According to one embodiment, an applicator comprises a tandem catheter and comprises two colpostats arranged for introduction of radioactive sources for intracavitary brachytherapy. The tandem can be integrated with an endoscope in some embodiments that gives the capability of locating the cervical os and guiding the tandem into the uterine canal. The conventional FSD applicator colpostats are made of variously sized rigid caps. According to one embodiment, the applicator comprises two inflatable ovoid cator can allow for the tandem and ovoids to be assembled and/or configured rapidly. Adjustments to the system can be completed outside of the patient, similar to a laproscopy procedure. Advantages of the applicator systems and methods of use include simplification of the use of the implant, utilizing fewer parts, adjustable ovoids fitting the patient fornices with comfort, and the inflatable retraction mechanism to separate and give adequate distance to the bladder and rectum. This will optimize the dose to the cervix and uterus, minimizing the dose to these critical structures.

In some embodiments, advantages of applicator systems and methods may include easier and faster implantation. The applicator can cause less or no pain to the patient. The applicator can reduce complications to the patient. The applicator can have simple and integrated applicator parts. Methods of using the applicator and performing treatments can be reproducible. The applicator can provide improved implant geometry. The applicator can be configured to provide for manipulations to be done outside the vaginal and uterine canals, thus making the implant less invasive and geometrically advantageous. The applicator can provide improved radiation dosimetry and lower dose to bladder and rectum.

According to one embodiment, a system for treating cervical and/or uterine cancers in brachytherapy with an intracavitary brachytherapy applicator comprises a tandem adapted for insertion into a cervix of a patient. The tandem comprises an endoscopic viewing element to facilitate treatment and one or more radiographic markers. An ovoid assembly comprises first and second adjustably inflatable ovoids and an ovoid support mechanism. The ovoid support mechanism is adapted to support the ovoids and to allow for user manipulation to control the relative position of the ovoids for insertion of the ovoids within the fornices of a patient. The first and second adjustably inflatable ovoids have a deflated configuration for insertion into a patient and one or more adjustably inflated configurations for positioning the ovoid assembly during treatment. The first and second ovoids each have one or more radiographic markers. The ovoid assembly comprises a tandem connector adapted to releasably and adjustably couple the tandem to the ovoid assembly to allow for pivotal and translational motion of the tandem relative to the ovoid assembly and to limit rotational movement of the tandem about a longitudinal axis of the tandem. First and second adjustably inflatable retractors are adapted to be releasably coupled to the ovoid assembly at first and second retractor connector portions. The first and second inflatable retractors have a deflated configuration for insertion into a patient and an adjustably inflated configuration for retraction of tissue during treatment. The first retractor is adapted to be positioned to retract the bladder of a patient during treatment and the second retractor is adapted to be positioned to retract the rectum of a patient during treatment. The tandem and the first and second inflatable ovoids are adapted to be coupled to a radioactive source to deliver an implant radiation dose suitable for cancer treatment at a cancerous cervical treatment site in a patient.

According to another embodiment, a system for treating cervical and/or uterine cancers in brachytherapy with an intracavitary brachytherapy applicator comprises a tandem adapted for insertion into a cervix of a patient. An ovoid assembly comprises first and second inflatable ovoids and an ovoid support mechanism. The first and second inflatable ovoids are adapted for insertion within fornices of a patient. First and second retractors are adapted to be coupled to the ovoid assembly. The first retractor is adapted to be positioned to retract the bladder of a patient during treatment and the second retractor is adapted to be positioned to retract the rectum of a patient during treatment. The tandem and the first and second inflatable ovoids are adapted to be coupled to a radioactive source to deliver an implant radiation dose suitable for cancer treatment at a cancerous cervical treatment site in a patient.

According to another aspect, a method of treating cervical and/or uterine cancers in brachytherapy with an intracavitary brachytherapy applicator comprises providing an intracavitary brachytherapy applicator having a tandem, an ovoid assembly comprising first and second inflatable ovoids and an ovoid support mechanism, and first and second retractors adapted to be coupled to the ovoid assembly. The tandem is inserted into a cervix of a patient. The first and second inflatable ovoids are inserted within fornices of a patient. The first and second retractors are inserted within a patient. The first and second inflatable ovoids are inflated within a patient. The bladder of a patient is retracted from a treatment site. The rectum of a patient is retracted from a treatment site. An implant radiation dose suitable for treatment is delivered at a treatment site.

According to another aspect, a method of treating cervical and/or uterine cancers in brachytherapy with an intracavitary brachytherapy applicator can comprise one or more of the following steps. First and second retractors can be coupled to the ovoid assembly prior to insertion within a patient. The tandem and the first and second inflatable ovoids can be coupled to a radioactive source. Retracting the bladder can comprise inflating the first retractor. Retracting the rectum can comprise inflating the second retractor. The tandem can be coupled to the ovoid assembly. The tandem can be translated relative to the ovoid assembly. The tandem can be pivoted relative to the ovoid assembly. The tandem can comprise an endoscopic viewing element. A portion of the anatomy of the patient can be viewed with the viewing element upon insertion of the tandem within the patient. Rotational movement of the tandem about a longitudinal axis of the tandem can be limited by a connection between the tandem and ovoid assembly.

According to some embodiments, a system for treating cervical and/or uterine cancers in brachytherapy with an intracavitary brachytherapy applicator comprises a tandem adapted for insertion into a cervix of a patient. An ovoid assembly comprises first and second inflatable ovoids and an ovoid support mechanism. The first and second inflatable ovoids are adapted for insertion within fornices of a patient. The ovoid support mechanism is adapted to support the ovoids and to allow for user manipulation to control the relative position of the ovoids for insertion of the ovoids within the fornices of a patient. The ovoid support mechanism comprises first and second handles wherein the handles are configured to allow for user manipulation to control the relative position of the ovoids using a coarse adjustment mechanism in a first configuration and using a fine adjustment mechanism in a second configuration. First and second retractors are adapted to be coupled to the ovoid assembly. The first retractor is adapted to be positioned to retract the bladder of a patient during treatment and the second retractor is adapted to be positioned to retract the rectum of a patient during treatment. The tandem and the first and second inflatable ovoids are adapted to be coupled to a radioactive source to deliver an implant radiation dose suitable for cancer treatment at a cancerous cervical treatment site in a patient.

According to some embodiments, a system for treating cervical and/or uterine cancers in brachytherapy with an intracavitary brachytherapy applicator comprises a tandem adapted for insertion into a cervix of a patient. An ovoid assembly comprises first and second inflatable ovoids and an ovoid support mechanism. The first and second inflatable ovoids are adapted for insertion within fornices of a patient. The ovoid assembly comprises a tandem connector adapted to releasably and adjustably couple the tandem to the ovoid assembly. The ovoid assembly comprises a first configuration wherein one or more handles coupled to the tandem connector are in an open position and adapted for pivotal and translational movement of the tandem, and a second configuration wherein the one or more handles coupled to the tandem connector are in a closed position and adapted to clamp the tandem connector to limit movement of the tandem. First and second retractors are adapted to be coupled to the ovoid assembly. The first retractor is adapted to be positioned to retract the bladder of a patient during treatment and the second retractor is adapted to be positioned to retract the rectum of a patient during treatment. The tandem and the first and second inflatable ovoids are adapted to be coupled to a radioactive source to deliver an implant radiation dose suitable for cancer treatment at a cancerous cervical treatment site in a patient.

According to some embodiments, a system for treating cervical and/or uterine cancers in brachytherapy with an intracavitary brachytherapy applicator, comprises a tandem adapted for insertion into a cervix of a patient. An ovoid assembly comprises first and second inflatable ovoids and an ovoid support mechanism. The first and second inflatable ovoids are adapted for insertion within fornices of a patient. First and second retractors are adapted to be coupled to the ovoid assembly. The first retractor is adapted to be positioned to retract the bladder of a patient during treatment and the second retractor is adapted to be positioned to retract the rectum of a patient during treatment. The first and second retractors are adapted to be releasably coupled to the ovoid assembly. The first and second retractors have attachment mechanisms comprising spring actuated lock mechanisms adapted to provide for adjustment of the position of the retractor and to provide for a snap fit connection with the ovoid assembly. The tandem and the first and second inflatable ovoids are adapted to be coupled to a radioactive source to deliver an implant radiation dose suitable for cancer treatment at a cancerous cervical treatment site in a patient.

Still other aspects, features, and attendant advantages of the present application will become apparent to those skilled in the art from a reading of the following detailed description of embodiments constructed in accordance therewith, taken in conjunction with the accompanying drawings. Aspects, features, and attendant advantages of the present application provide improvements over known devices, systems and methods. Some devices, systems and methods related to brachytherapy are described in more detail in the following references, each of which is hereby incorporated by reference herein in its entirety. 1. J. Rahimian, Y. Qian, R. Kagan, Effects of Applicator Spatial Placement Variations on Cumulative Dose to Point A in the Treatment of Cervical Cancer with 3 HDR Intracavitary Brachytherapy Treatments. Medical Physics, Vol. 26, No. 6, p. 1142, 1999 (abstract); 2. Faiz M. Khan. The Physics of Radiation Therapy. Third Edition. Lippincott Williams & Wilkins Publishers, 2003; 3. H. K. Malhotra, J. S. Avadhani, S. F. deBoer, et. al. Duplicating a tandem and ovoids distribution with intensity modulated radiotherapy: a feasibility study. J. of Appl. Clin. Med. Phys. Vo. 8, No 3 (2007).

DETAILED DESCRIPTION

Figure 1:
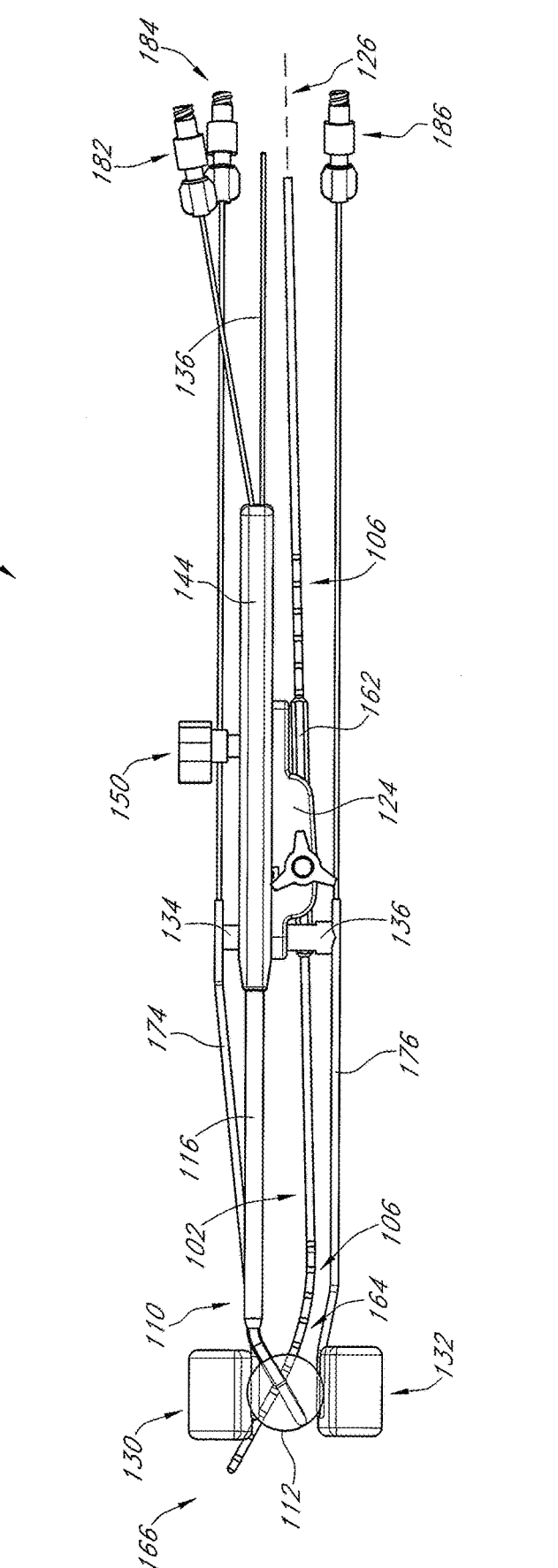
FIG. 1 illustrates a side view of an assembled minimally invasive intracavitary brachytherapy applicator system according to embodiments of the present application.
Figure 2:
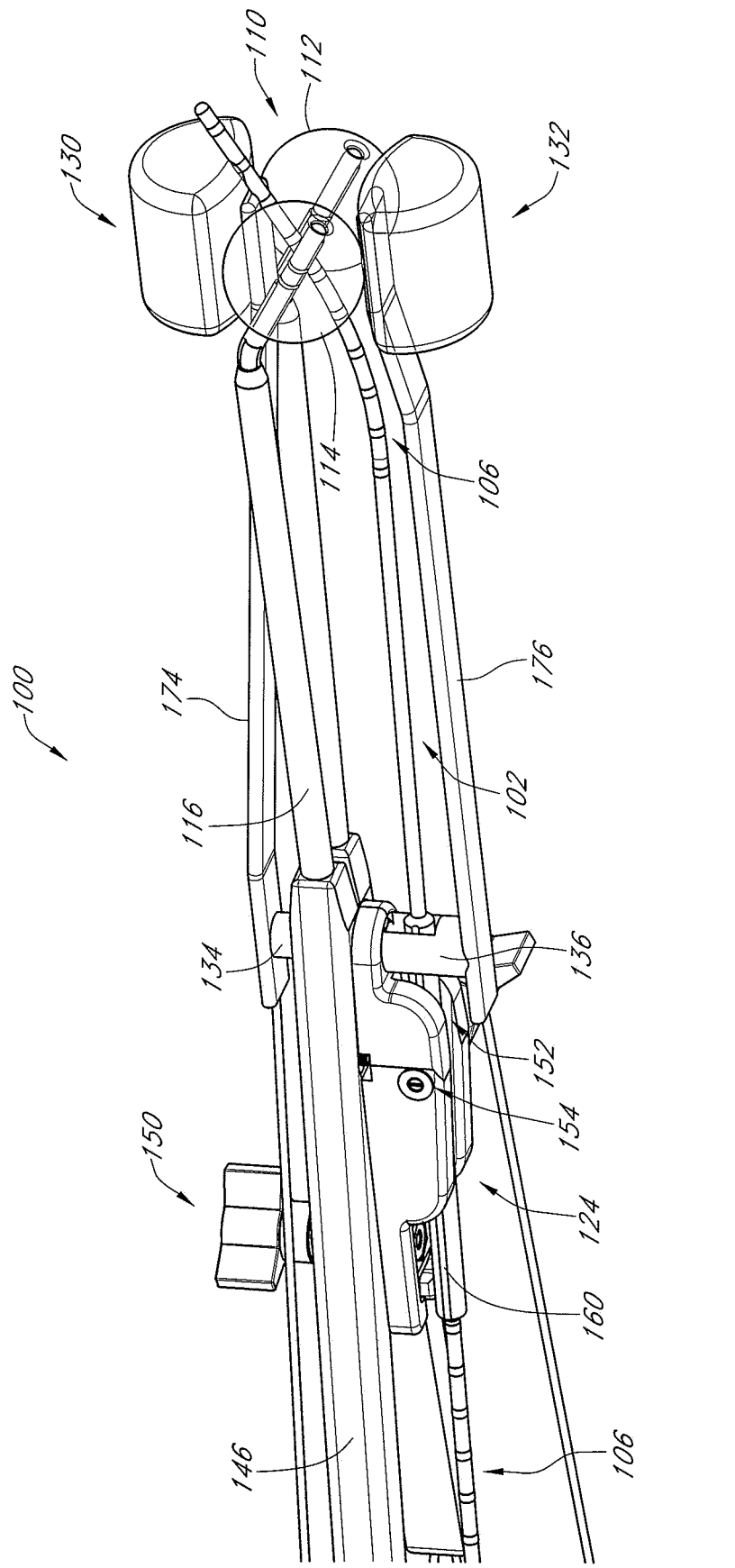
FIG. 2 illustrates a perspective view of a distal portion of the applicator system of FIG. 1 according to embodiments of the present application.
Figure 3:
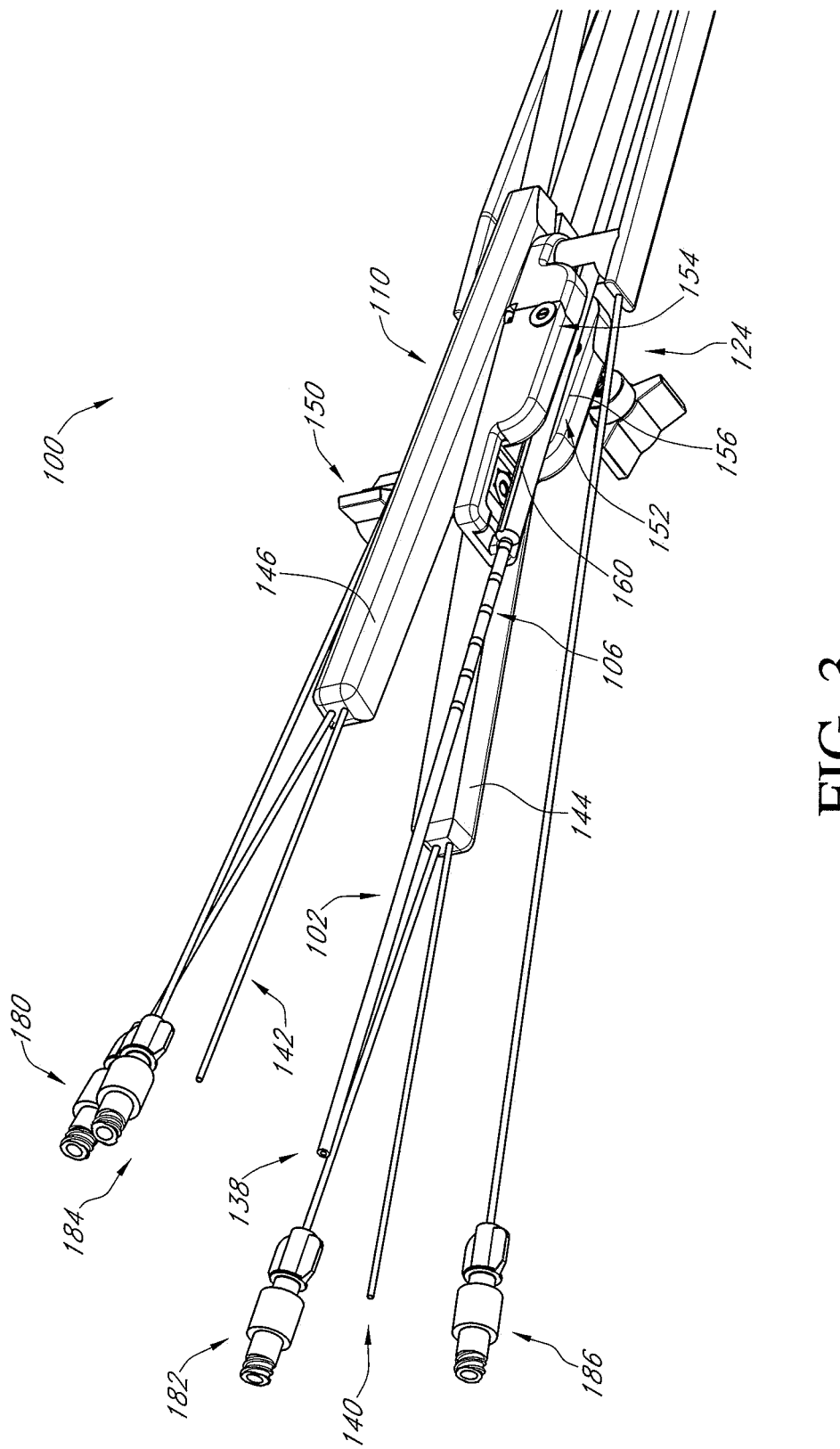
FIG. 3 illustrates a perspective view of a proximal portion of the applicator system of FIG. 1 according to embodiments of the present application.
Figure 4:
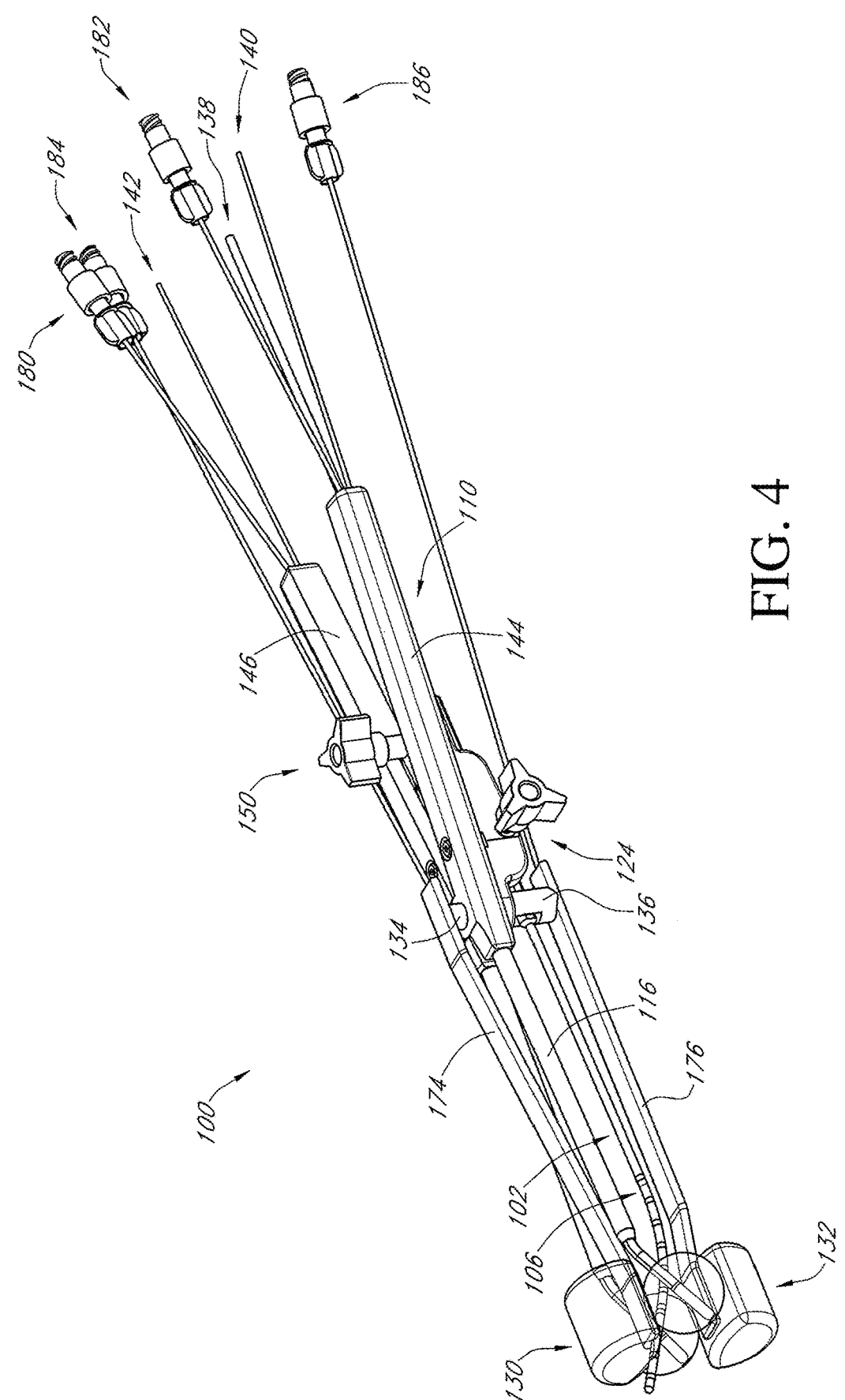
FIG. 4 illustrates a side perspective view of the applicator system of FIG. 1 according to embodiments of the present application.
Figure 5:
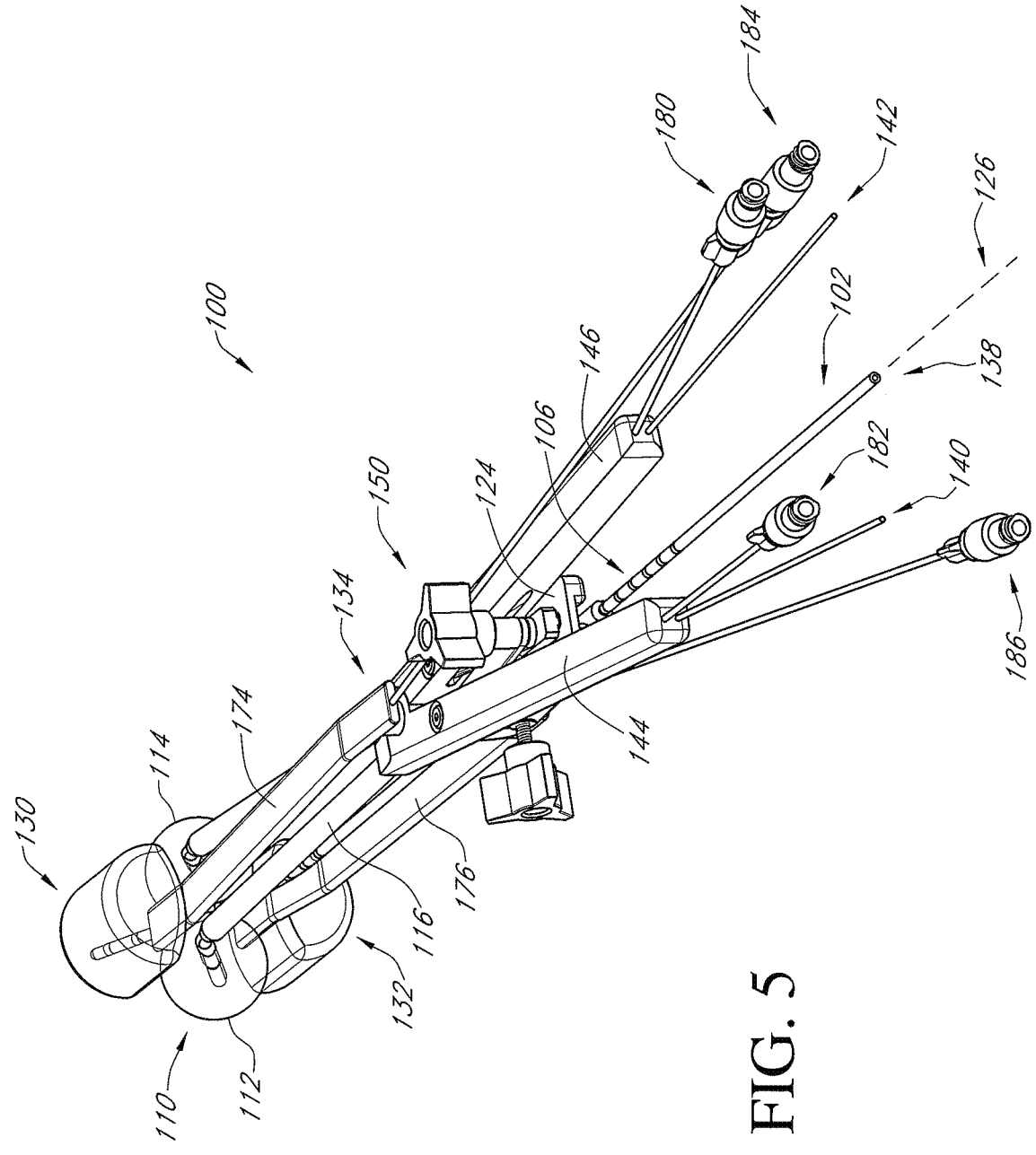
FIG. 5 illustrates a rear perspective view of the proximal portion of the applicator system of FIG. 1 according to embodiments of the present application.
Figure 6:
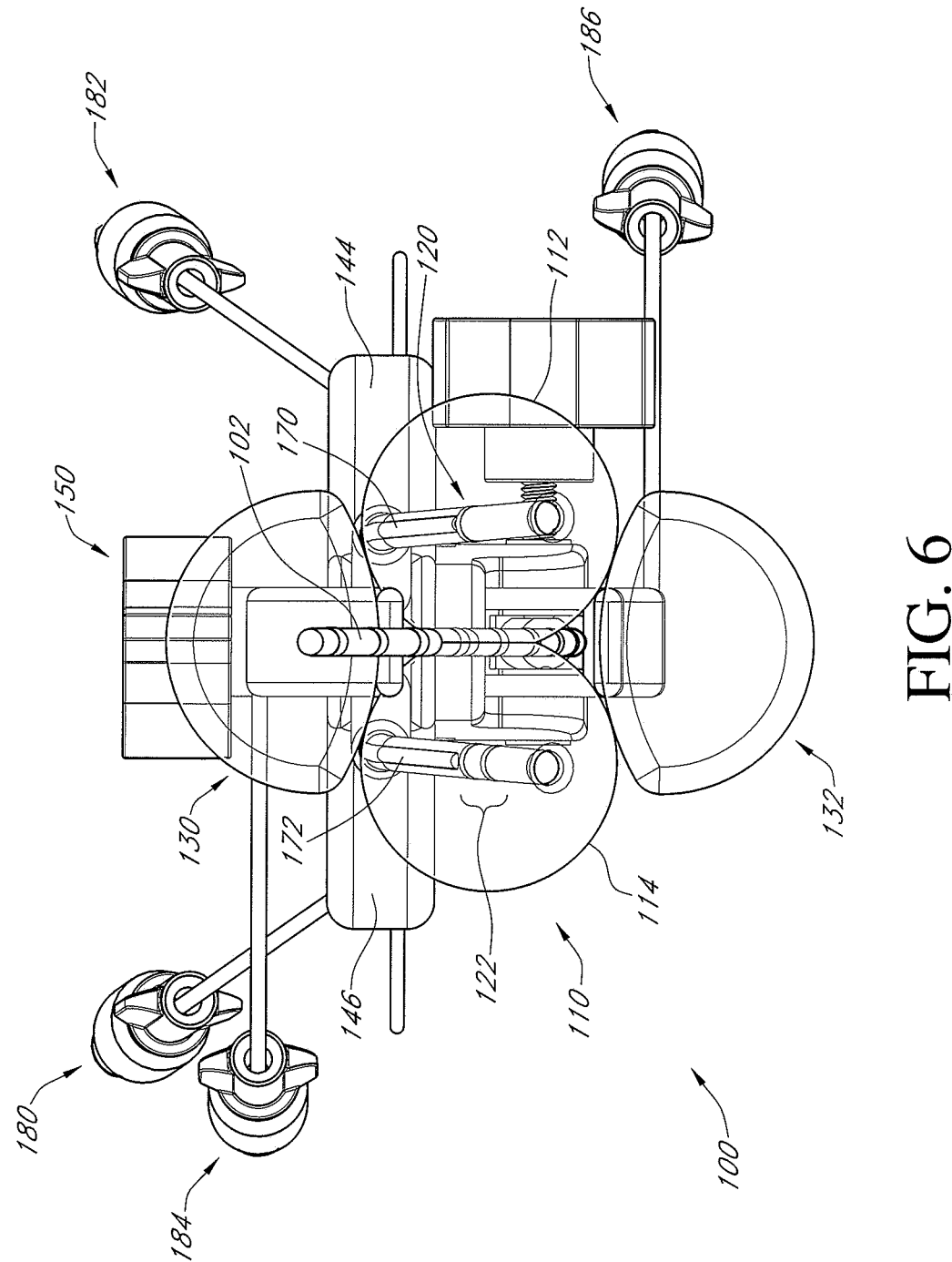
FIG. 6 illustrates a front view of the distal portion of the applicator system of FIG. 1 according to embodiments of the present application.
Figure 7:
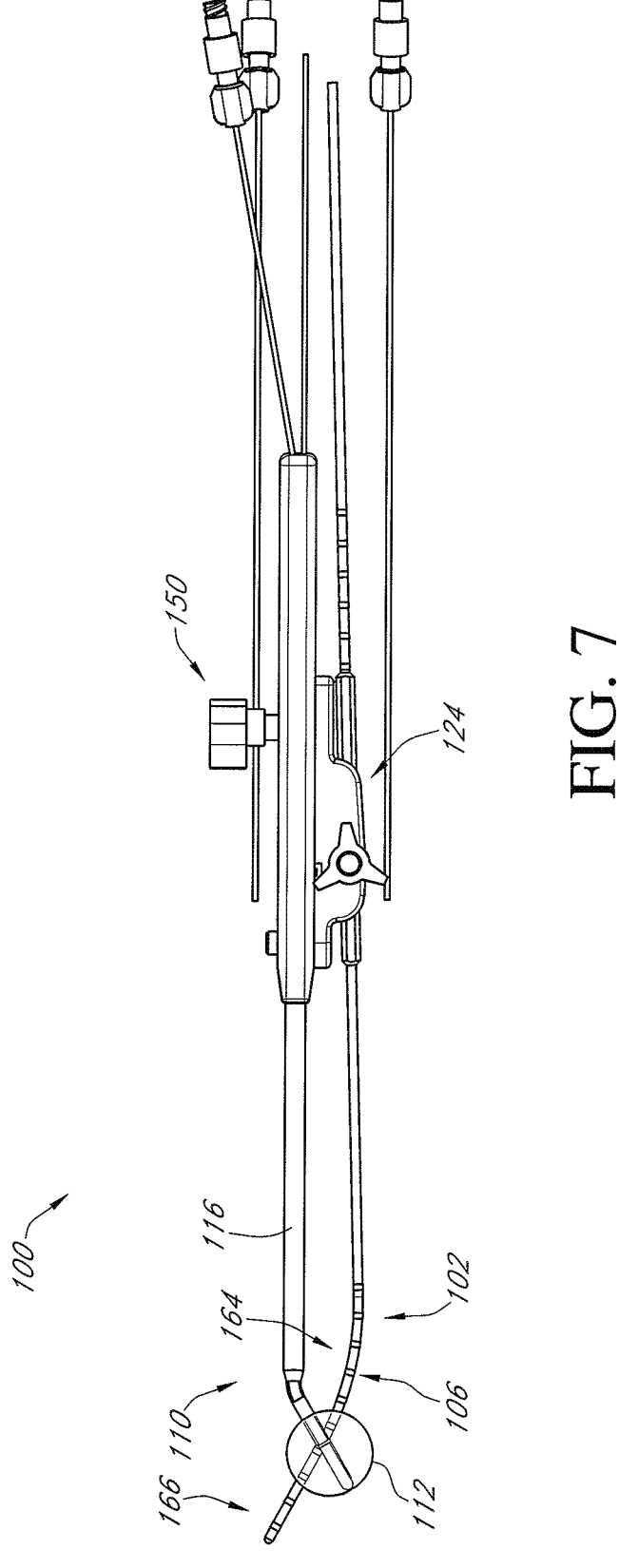
FIG. 7 illustrates a side view of an assembled minimally invasive intracavitary brachytherapy applicator system similar to the system shown in FIG. 1 without the retractor assemblies.
Figure 8:
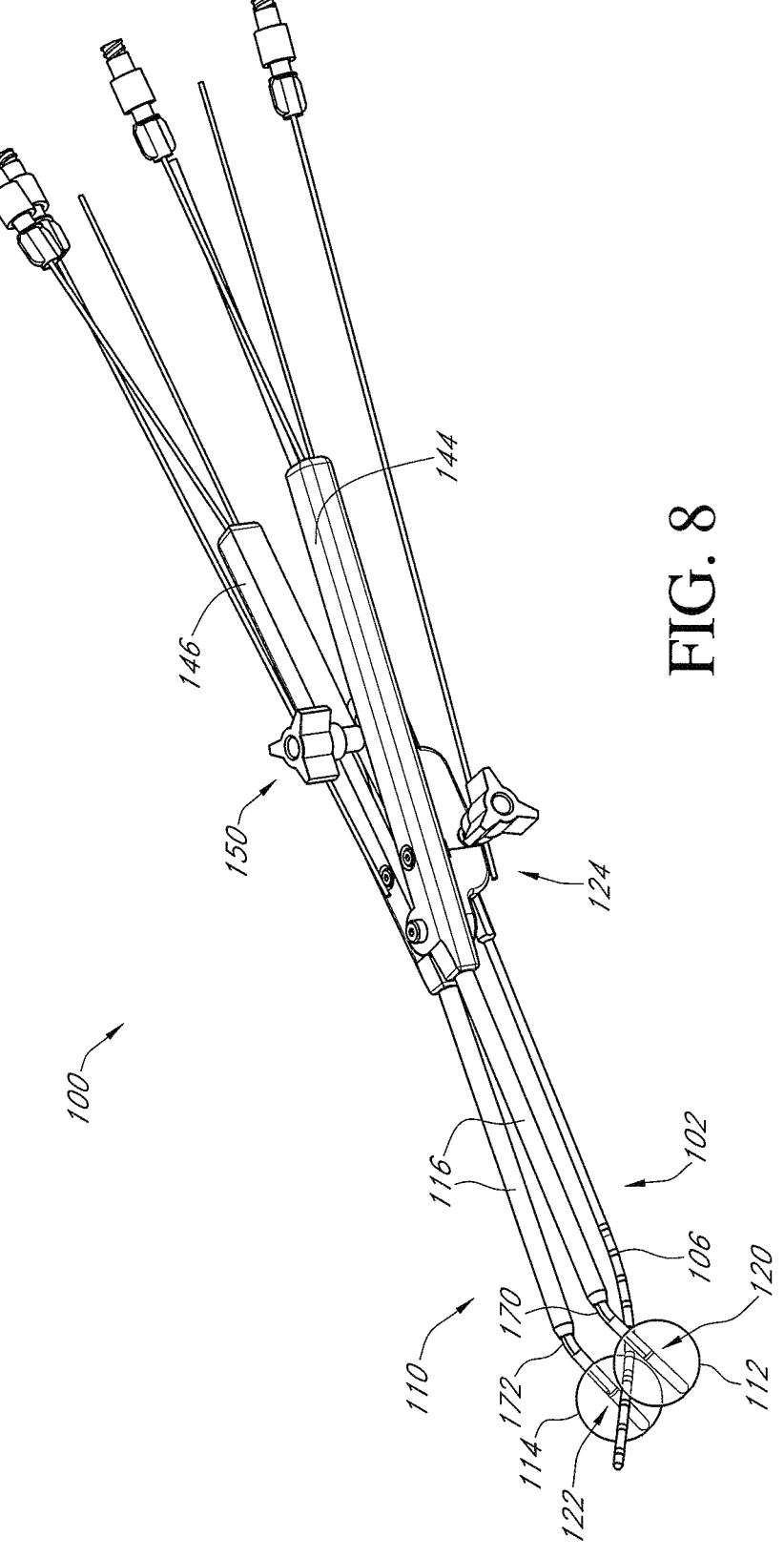
FIG. 8 illustrates a front side perspective view of the applicator system of FIG. 7 according to embodiments of the present application.
Figure 9:
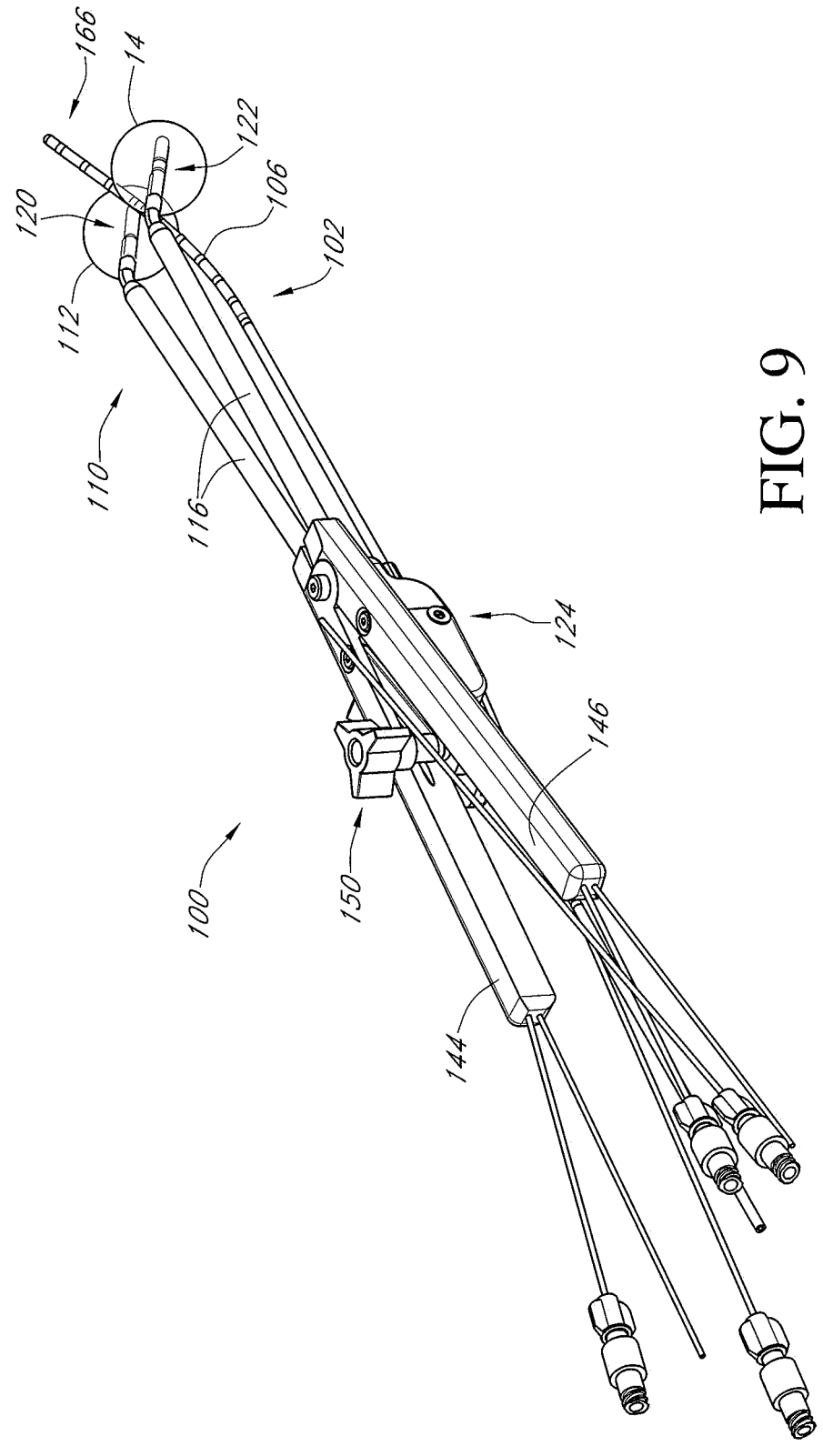
FIG. 9 illustrates a rear side perspective view of the applicator system of FIG. 7 according to embodiments of the present application.
Figure 10:
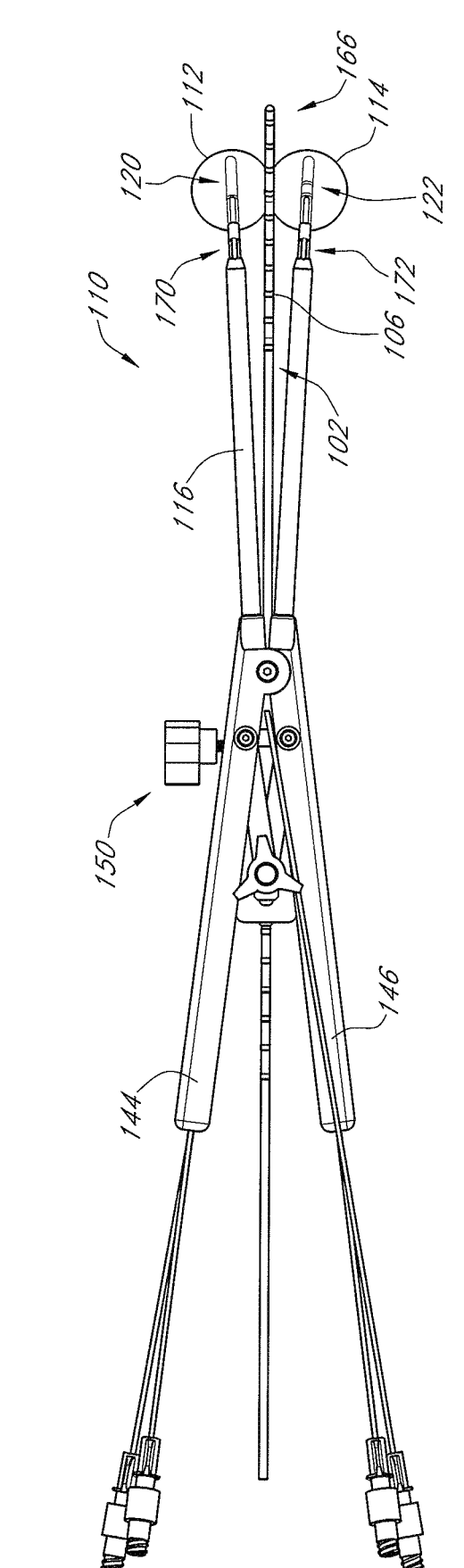
FIG. 10 illustrates a top view of the applicator system of FIG. 7 according to embodiments of the present application.

Papanicolaou testing, routine gynecological screening, and the development of a vaccine against several types of the human papillomavirus have reduced the incidence of cervical cancer. However, cervical cancer remains the second most common cause of cancer in women. While these preventative efforts are likely to have a long term beneficial effect, screening efforts are far from universally effective. Vaccination and screening efforts are expected to lag in developing countries, which will delay the realized benefits of these public health efforts. The American Cancer Society estimates that in 2017 there were 12,820 and 61,380 new cancers of the uterine cervix and uterine corpus, respectively. The organization further estimates that over 15,130 women died of uterine cancers within that year. Nearly 528,000 women received the diagnosis of cervical cancer in 2012 and about 320,000 women learned of their uterine cancer in the world. A major risk factor for cervical cancers is human papilloma virus (HPV) infection, especially with strains like HPV 16, 18, 31, 33, and 45, which are termed as high risk factor strains. Other known risk factors include: smoking, HIV infection, low socioeconomic status, chlamydia infection, oral contraceptives, and multiple pregnancies.

There are several approaches to the treatment of cervical cancer and uterine neoplasms. These methods include hysterectomy, external beam radiation therapy, brachytherapy, and chemotherapy amongst others. The treatment approach depends largely on the stage of the disease, though definitive radiation therapy (external and internal) can be a helpful component of treatment in most stages. Brachytherapy (internal radiation) can be particularly important in many cases since small sources of energetic radioactive substances (e.g. Cesium-137 or Iridium-192 or Cobalt-60) can be placed adjacent to the tumor in an applicator. Because the extent of the effects of these radioisotopes (radiation dose) drop off rather precipitously with distance, brachytherapy has the chance to reduce damage to surrounding organs such as the urinary bladder and rectum compared to external radiation.

Brachytherapy for cervical cancer treatment is classified into low dose-rate (LDR) and high dose-rate (HDR). Multiple studies have documented essentially equal efficacy of LDR and HDR brachytherapy in terms of local control rate, recurrence, metastasis and complications. Nevertheless, HDR may offer some advantages for the patient over LDR. For example, HDR can be performed as an outpatient procedure while LDR requires the patient to remain hospitalized—and in many cases isolated for fear of irradiating others—for a period of three to four days per treatment. In both LDR and HDR brachytherapy, the radiation source must be placed in the applicator and implanted into the vaginal vault in a precise orientation.

One device that is used for this purpose is called the Fletcher-Suit-Delclos (FSD) applicator. The current design of the FSD applicator is the result of modifications to the Fletcher applicator developed in the 1950s. The traditional implant device typically consists of eight pieces.

Components of the FSD are assembled sequentially while the patient is in stirrups position and under anesthesia or conscious sedation. While data on patient attitudes and preferences is quite limited it is generally accepted that the brachytherapy procedure is at best uncomfortable and anxiety-provoking and at worst torturous. Patients are required to endure intravaginal manipulation for up to three hours per brachytherapy treatment. LDR treatment can require two sessions with a lengthy hospital stay while HDR treatment can require three to five insertions, usually as an outpatient. The bulk of insertion time is spent assembling the device and optimizing placement. While some image-guided techniques are in the process of being developed, insertions are largely done blindly and in a trial-and-error fashion.

Brachytherapy treatment of cervical and uterine cancers is not only time-intensive and difficult for the patient, it also is labor-intensive. Treatment requires the coordinated efforts of a number of highly trained personnel including a radiation oncologist, an anesthesiologist, two nurses, a radiation therapist, a dosimetrists, and a medical physicist to implant the applicator in the patient, calculate the dose, and deliver the radiation per radiation oncologist's prescription.

Novel intracavitary brachytherapy applicator systems described herein can improve upon the current treatment process in several ways. First, patient comfort and care are improved. In some embodiments, the device is much easier to assemble and position than the current FSD device. Because of this, brachytherapy application times should be shortened significantly. For instance, our initial estimates indicate that our proposed device (compared to FSD) will decrease insertion and placement times from one to two hours to 15-20 minutes. Expediting the process in this way eases patient discomfort considerably. Moreover, a shortened procedure time reduces the time in which the patient receives sedative or anesthetic, which promotes patient safety.

Another benefit of embodiments disclosed herein is to reduce the number of medical personnel needed to perform the brachytherapy procedure while improving user satisfaction. Because treatment times will likely be shorter and the device is much easier to assemble and use than the FSD, we expect physicians and medical personnel to strongly prefer embodiments disclosed herein. Furthermore, as patients are forced to endure a much less invasive procedure than FSD, patient satisfaction is expected to lead to increased provider satisfaction.

In some embodiments, the device is designed to be disposable and, as such, produced at much lower cost compared with the existing reusable systems. Further, due to inadequate sterilization technique for the reusable applicators, a potentially problematic infectious disease could be prevented by our disposable applicator. Estimates suggest that there is a financial benefit to hospitals and payers by using our device instead of FSD. The dramatically decreased treatment times enjoyed with our device will reduce Operating Room time and costs, medication costs, and (perhaps most expensive) personnel costs. As patients are given an informed choice between a two-hour procedure and a 15-30 minute procedure, our device will provide a competitive advantage for those institutions that adopt it. As described herein, a kit including an ovoid assembly, one or more tandems (e.g., 2, 3, 4, or more) each with an angle (e.g., of about 0°, 15°, 30°, and) 45°, a tandem holder, and/or bladder and/or rectum retractors can be housed in a tray, covered and labeled, and the whole package can be sterilized with gamma emitting radiation. This sterilization process can make the whole package or kit to be ready for implant.

Embodiments of the brachytherapy applicators system disclosed herein are not merely a refinement of the Fletcher instrument described above, but rather greatly depart from the classic FSD device. In some embodiments, the device comprises two main pieces, rather than eight. The device may comprise a tandem and two inflatable ovoids (see FIG. 19 below). The ovoids may be integrated into the device and in such embodiments can be securely attached to the tandem in a single step. The ovoids may be separate and/or variably inflated using a syringe and valve located on the external section of the applicator. This arrangement is similar to the inflatable bladder that is used to secure a Foley catheter in the urinary bladder. The bladders may be inflated with water in order to position and secure the applicator in the vaginal vault.

The entire device can be positioned into any required orientation using controls located outside of the patient's body. In this respect, certain embodiments of the device may be more like an endoscopic surgical instrument than the classic FSD device. This simplified design can allow users to easily and quickly assemble the device and adjust it in lateral and/or anterior-posterior directions.

One of the most troubling treatment-related complications of intracavitary brachytherapy is local damage to radiosensitive organs, namely the urinary bladder and the rectum. Our applicator system can include two separate inflatable bladders that can be used to displace the urinary bladder and the rectum, which can reduce or eliminate the messy packing that is typically used. Since local invasion of cervical and uterine neoplasms may derange the normal anatomy, one, both, or neither bladders may be inserted to provide extra distance between the radiation source and sensitive structures.

Currently, the correct insertion of internal radiation is a technically complex process that requires highly trained and experienced personnel. The training time required to gain competency with the FSD applicator is substantial—it generally takes residents numerous attempts to correctly learn how to place the device. In fact, it has been suggested that intracavitary brachytherapy treatment be relegated to larger universities and teaching hospitals where clinicians perform enough procedures to develop and maintain the necessary proficiency. Optimal positioning of both LDR and HDR radiation sources can greatly benefit the outcome of intracavitary brachytherapy. While imaging has been routinely and successfully integrated into prostate cancer brachytherapy, most cervical and uterine procedures are carried out using a blind approach for insertion and positioning. This prolongs the procedure and extends the patient's discomfort and need for sedation.

The tandem and ovoid assemblies can be sized to fit a low energy radiation source from Electronic Brachytherapy (EBT) systems, such as Xoft EBT systems. Xoft systems produces 50 kVp x-rays at the tip of a 3 mm diameter catheter that is being used for Brachytherapy of the vaginal cylinder, a tandem and ovoid assembly for treating uterine and/or cervical cancers, skin cancer, and/or intraoperative radiotherapy of breast cancer.

Locally advanced cervical cancer and external beam radiotherapy can alter normal intravaginal anatomy. Consequently, finding the cervical os during brachytherapy treatment can be very difficult and time-consuming. Often, ultrasound imaging is required to find the uterine canal. To facilitate faster and more efficient placement of the radiation source, various beneficial aspects may be included, described herein. To place the tandem into the uterine canal, we propose to use a miniaturized CMOS camera, or a miniaturized ultrasonic transducer or both to navigate through the vaginal canal, the cervical os, and the uterine canal. The image guided endoscopic tandem placement should accelerate the insertion time without multiple poking of the cervix to find the os using the speculum, and also to prevent from perforating the uterus. Treating a tandem perforated through the uterus into the small bowel can cause significant radiation damage to the small bowel, as well as there is a significant risk of small bowel obstruction and infection.

The present application relates to devices and methods for treating cervical and/or uterine cancers in brachytherapy with an intracavitary brachytherapy applicator. According to some embodiments, an intracavitary brachytherapy applicator has a tandem and first and second inflatable ovoids. The tandem and ovoids are adapted to deliver an implant radiation dose for treatment of a patient. In some embodiments the applicator comprises one or more retractors. The ovoids are preferably coupled to an ovoid assembly to support the ovoids and to control the relative position of the ovoids. The tandem is preferably releasably coupled to the ovoid assembly and is adjustable relative to the ovoid assembly. The tandem preferably pivots and translates relative to the ovoid assembly. The tandem is preferably coupled to the ovoid assembly in a manner that limits or restricts rotation of the tandem about a longitudinal axis of the tandem. In some embodiments retractors are releasably coupled with the ovoid assembly. In other embodiments retractors can be fixed or attached to the ovoid assembly. A first retractor can be positioned to retract the bladder of a patient during treatment and a second retractor can be positioned to retract the rectum of a patient during treatment. The retractors are preferably inflatable to at least partially retract the bladder and rectum from a treatment site. In some other embodiments the retractors are not inflatable. In some embodiments the tandem is preferably integrated with an endoscope to facilitate applicator placement and treatment.

In some embodiments, an advanced and minimally invasive cervical and uterine HDR and/or LDR applicator system comprises a tandem catheter adapted to be placed inside the uterine canal with two inflatable catheters placed next to the cervical fornices, while using two inflatable semi-cylindrical balloons to retract the bladder and rectum away from the radioactive sources. The tandem central catheter can include endoscopic fiber optics to transmit images of the cervical os, as well as the uterine canal as it is placed. This can facilitate insertion, limit multiple pokes of the cervix, may limit injury to the cervix and uterine perforation causing injury and infection to the uterus as well as to the small bowel. In addition, placement of the applicator is likely to be much faster, preferably on the order of minutes rather than over an hour. The endoscopic tandem and the dual ovoid assembly can be configured as a single piece that advantageously enables the radiation oncologist to implant the applicator possibly without a speculum, reducing pain, anesthetics, and stress on the nursing personnel and the radiation oncologist.

With reference to FIGS. 1-14, according to some embodiments, systems for treating cervical and/or uterine cancers in brachytherapy with an intracavitary brachytherapy applicator 100 comprise a tandem 102 adapted for insertion into a cervix of a patient. The tandem 102 can comprise an endoscopic viewing element 104 to facilitate treatment and one or more radiographic markers 106.

An ovoid assembly 110 comprises first and second adjustably inflatable ovoids 112, 114 and an ovoid support mechanism 116. The ovoid support mechanism 116 is adapted to support the ovoids 112, 114 and to allow for user manipulation to control the relative position of the ovoids for insertion of the ovoids within the fornices of a patient. The first and second adjustably inflatable ovoids 112, 114 have a deflated configuration for insertion into a patient and one or more adjustably inflated configurations for positioning the ovoid assembly during treatment. The first and second ovoids 112, 114 each have one or more radiographic markers 120, 122. The ovoid assembly 110 comprises a tandem connector 124 adapted to releasably and adjustably couple the tandem 102 to the ovoid assembly 110 to allow for pivotal and translational motion of the tandem 102 relative to the ovoid assembly 110 and to limit rotational movement of the tandem 102 about a longitudinal axis of the tandem.

First and second adjustably inflatable retractors 130, 132 are adapted to be releasably coupled to the ovoid assembly at first and second retractor connector portions 134, 136. The first and second inflatable retractors 130, 132 have a deflated configuration for insertion into a patient and an adjustably inflated configuration for retraction of tissue during treatment. The first retractor 130 is adapted to be positioned to retract the bladder of a patient during treatment and the second retractor 132 is adapted to be positioned to retract the rectum of a patient during treatment. The tandem 102 and the first and second inflatable ovoids 112, 114 are adapted to be coupled to a radioactive source to deliver an implant radiation dose suitable for cancer treatment at a cancerous cervical treatment site in a patient.

Some embodiments are described in more detail below. The applicator systems and methods can have one or more of the following advantageous characteristics in some embodiments.

Applicator Assembly

Some embodiments include applicator systems 100 that can be pre-assembled before insertion into the patient such that only a few, and in some cases, preferably one or two adjustable and integrated pieces are inserted into the patient. In contrast, the current FSD applicators require about 8 pieces to be assembled while inserted within a patient during use. Accordingly, use of embodiments of the present application preferably makes insertion and manipulation of the implants faster, more dosimetrically optimal, lessens the need for anesthetics, and reduces pain to the patient.

Ovoid Assembly

As shown in FIGS. 1-12, the applicator system 100 comprises a pair of ovoids 112, 114 in the form of inflatable balloons, each with varying volume capacity, rather than solid caps of varying sizes currently used as colpostats. The inflatable balloon ovoids 112, 114 can advantageously and naturally take on the shape of mini, small, medium, and/or large size ovoids depending on the size of the patient's anatomy. In some embodiments, the ovoids 112, 114 can be independently inflated to 4 different sizes of the following approximate dimensions:

| SIZE | WIDTH | LENGTH | VOLUME |
|---|---|---|---|
| Mini | 1.4 cm | 3.0 | 5 cc |
| Small | 2.0 cm | 3.0 | 10 cc |
| Medium | 2.5 cm | 3.0 | 15 cc |
| Large | 3.0 cm | 3.0 | 21 cc |

Depending on the patient's anatomy, and the extent, and the size, and the side of the gross disease, the two ovoids 112, 114 can be inflated with different volumes. For example, one ovoid can be inflated as small size and the other as medium size ovoid. The left and the right side ovoids are preferably substantially identical in size, even though at the radiation oncologist's and/or the physicist's discretion, one can be inflated larger than the other depending on the extent of the disease and size of the fornices. In some other embodiments the ovoids can have different maximum sizes.

As described above and as shown in FIGS. 1-12, the ovoid support mechanism 116 is adapted to support the ovoids 112, 114 and to allow for user manipulation to control the relative position of the ovoids for insertion of the ovoids within the fornices of a patient. The ovoid support mechanism 116 supports first and second catheter shafts 140, 142 coupled with the ovoids for delivering radiation to the ovoids. The ovoid support mechanism also comprises first and second handle portions 144, 146 coupled for pivotal movement relative to one another. Movement of the handle portions 144, 146 relative to each other controls the distance between the first and second ovoids 112, 114. The relative position of the handle portions 144, 146 can be fixed by tightening a knob 150 at an upper portion of the ovoid support mechanism 116. A lower portion of the ovoid support mechanism 116 comprises the tandem connector 124. The tandem connector 124 comprises a slot 152 for receiving the tandem 102, a spring loaded ball or pin 154 on a first side of the slot 152 and a flat surface 156 on a second side of the slot 152. The tandem 102 comprises a groove 160 for translationally and pivotally coupling to the spring loaded ball or pin 154 when the tandem is positioned in the slot 152. A flat surface 162 of the tandem is positioned opposite the groove 160 and interfaces with the flat surface 156 of the tandem connector 124 when the tandem is positioned in the slot 152 to limit rotational movement of the tandem 102 about a longitudinal axis.

Tandem

Tandems 102 can have different shapes and configurations. For example, some embodiments include tandems having a curved portion 164 of 0, 15, 30, 45, and 60 degrees. The tandem 102 can be provided with or without endoscopic capabilities. Additionally, a tandem 102 can include radiographic markings, for example, one-cm markings, on it for measurement and/or viewing. The markers 106 can be positioned near the tandem tip 166 and/or near the tandem connector portion 124. The tandem 102 and the ovoids 112, 114 are coupled to catheter shafts 138, 140, and 142, respectively. The total internal length of the catheters 138, 140, and 142 are preferably substantially identical for both the tandem 102 and the ovoids 112, 114. In some other embodiments, the total lengths can vary. The internal length of the catheter shafts 138, 140, 142 of the tandem 102 and the two ovoids 112, 114 is preferably about 35 cm. Longer or shorter catheter lengths are also contemplated.

Tandem Coupling

Figure 13:
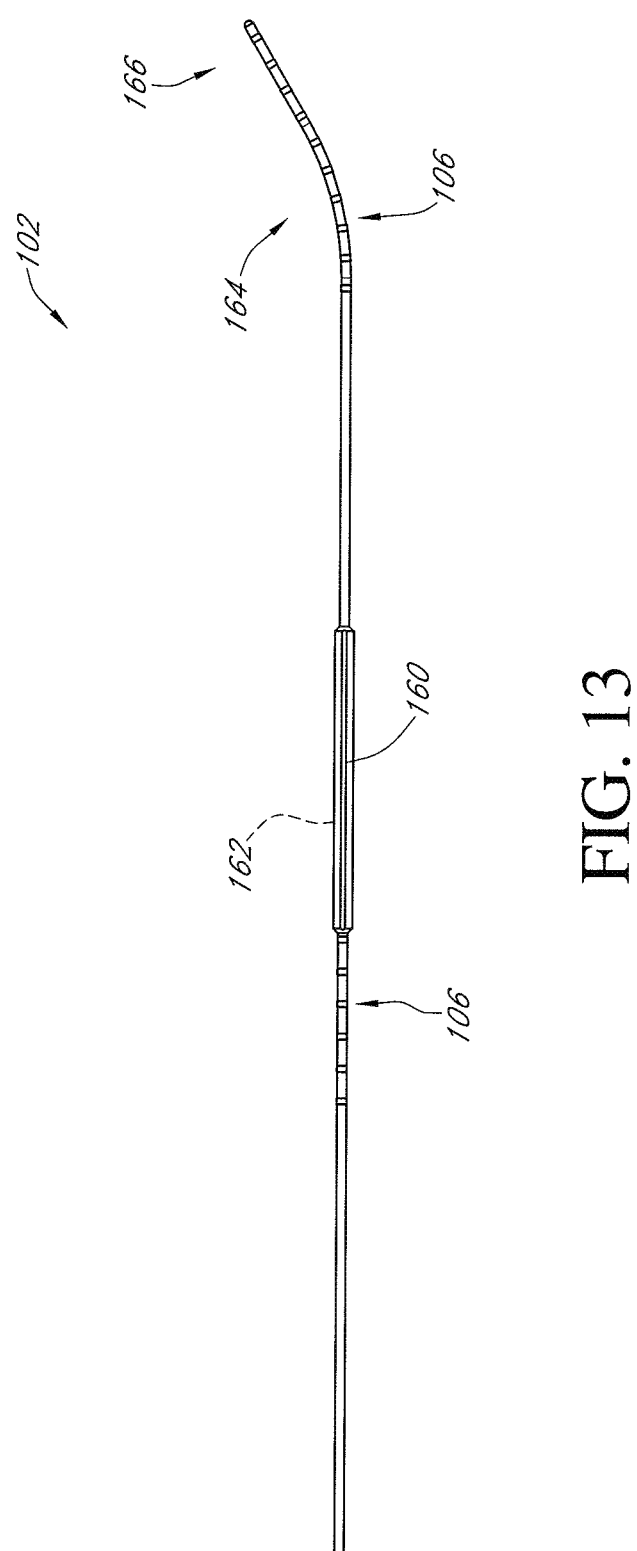
FIG. 13 illustrates a tandem portion of an applicator system according to embodiments of the present application.

As mentioned above, a tandem connector 124 mechanism is provided for coupling the tandem 102 with the ovoid assembly 110. The mechanism preferably enables the tandem 102 to pivot in the anterior/posterior direction about a point in reference to the ovoids 112, 114 using a spring-loaded ball bearing 154 within the ovoid assembly 110 to interface with a groove 160 on a side of the tandem as best seen in FIG. 13. The mechanism also preferably allows the user to translate and/or pivot the tandem to keep it at the mid-plane of the ovoids 112, 114 during treatment. Enabling the user to position the tandem 102 to bisect the ovoids 112, 114 helps to improve implant geometry and dose distribution. In some embodiments, a side of the tandem opposite the grooved side preferably has a flattened surface 162 that contacts a flattened surface 152 of the ovoid assembly 110 to limit inadvertent rotation of the tandem 102 during manipulation and treatment. Accordingly, the mechanism preferably limits the tandem from rotation around a longitudinal axis of the tandem and permits translational and pivotal motion to achieve an advantageous mid-plane position relative to the ovoids 112, 114.

Retractors

Retractor balloons 130, 132 are preferably added to the intracavitary brachytherapy applicator to retract the bladder and the rectum from the radiation sources, thus lowering the dose to these critical structures. This can reduce, and in some cases eliminate, the need to use of vaginal packing after the applicator is in place. The retractor balloons 130, 132 are coupled to catheters 184, 186 that are preferably anchored on the ovoid assembly 110. The retractor balloons 130, 132 are preferably inflated with saline. Other suitable inflation mediums can also be used. The balloons can be semi-cylindrical or semi-ellipsoid when inflated to push the vaginal mucosa, bladder, and rectum away from the radiation site. Balloons having other suitable shapes and sizes for providing retraction can also be used. The retraction mechanism is preferably inflatable to retract the bladder and the rectum by at least about 2 cm away from a plane of the implant defined at the plane of the tandem bisecting the ovoids. The retraction mechanism preferably retracts equidistance from the plane of the implant. The retraction mechanism comprises balloons 130, 132 and retractor supports 174, 176 coupled to the ovoid assembly 110 at retractor connection portions 134, 136.

Materials

The applicator system 100 can comprise environmentally friendly, disposable and/or recyclable materials. For example, plastics such as Delrin, Peek, GlassPeek, etc. can be used. Stainless steel or other suitable materials can be used. In some embodiments, use of allergy causing materials such as latex can be avoided. Balloon materials are preferably very strong, such as, for example, a double-layered polyurethane to avoid leaking and/or bursting. In some embodiments, the applicator is made of MRI and CT friendly materials.

Markers

As discussed above, radiographic markers can be provided along the catheters. Radiographic markers can be used to identify left and right ovoids 112, 114 by varying the number or style of markings 120, 122 on each ovoid. Radiographic markers can be provided on the external surfaces of the ovoid balloons 112, 114 to identify their placements and ensure proper expansion while being treated. Radiographic markers 106 can be provided on the tandem spaced one-cm apart to measure the length of the tandem 102 and/or to measure the magnification factor on the orthogonal radiographs. The applicator system preferably is adapted to be gamma ray, and gas sterilizable. The catheters of the applicator are preferably numbered and marked as corresponding to 1. Right Ovoid catheter 170, 2. Left Ovoid catheter 172, 3. The Luer Lock 182 inflating the Right Ovoid, 4. The Luer Lock 180 inflating the Left Ovoid, 5. The Luer Locks 184, 186 to inflate the retraction mechanism-one for the bladder and one for the rectum.

Guide Tubes

In some embodiments, the applicator 100 can be connected via three equal length transfer guide tubes or catheters 138, 140, 142 to the high dose brachytherapy afterloader with a 192-Iridium or 60-Cobalt High Dose Rate (HDR) radioactive source. In some embodiments the transfer guide tubes 138, 140, 142 can vary in length. The three transfer guide tubes 138, 140, 142 are coupled to the tandem 102 and the pair of inflatable ovoids 112, 114.

Radiation Treatment Modifications

In some embodiments, for Low Dose Rate (LDR) brachytherapy a similarly designed applicator can be used with either 137-Cs tubes or 192-Iridium ribbons (192-Ir seeds on a wire) placed inside plastic transfer guide tubes 138, 140, 142. The internal diameters of the tandem and the ovoids will be adjusted relative to the HDR applicator design to accommodate the commercially available 137-Cs tubes. For 192-Iridium ribbons the same tandem and ovoids designed for HDR can be used without any modifications to the internal diameter of the tandem and the ovoid catheters. Other parameters and characteristics of the applicator can be similar to those described for the HDR applicator. The LDR and HDR isodose distributions are preferably similar to the conventional FSD tandem and ovoids implants, yielding similar doses to the treatment site.

Endoscope Assembly

Figure 14:
FIG. 14 illustrates an endoscopic tandem portion of an applicator system according to embodiments of the present application.
Figure 15:
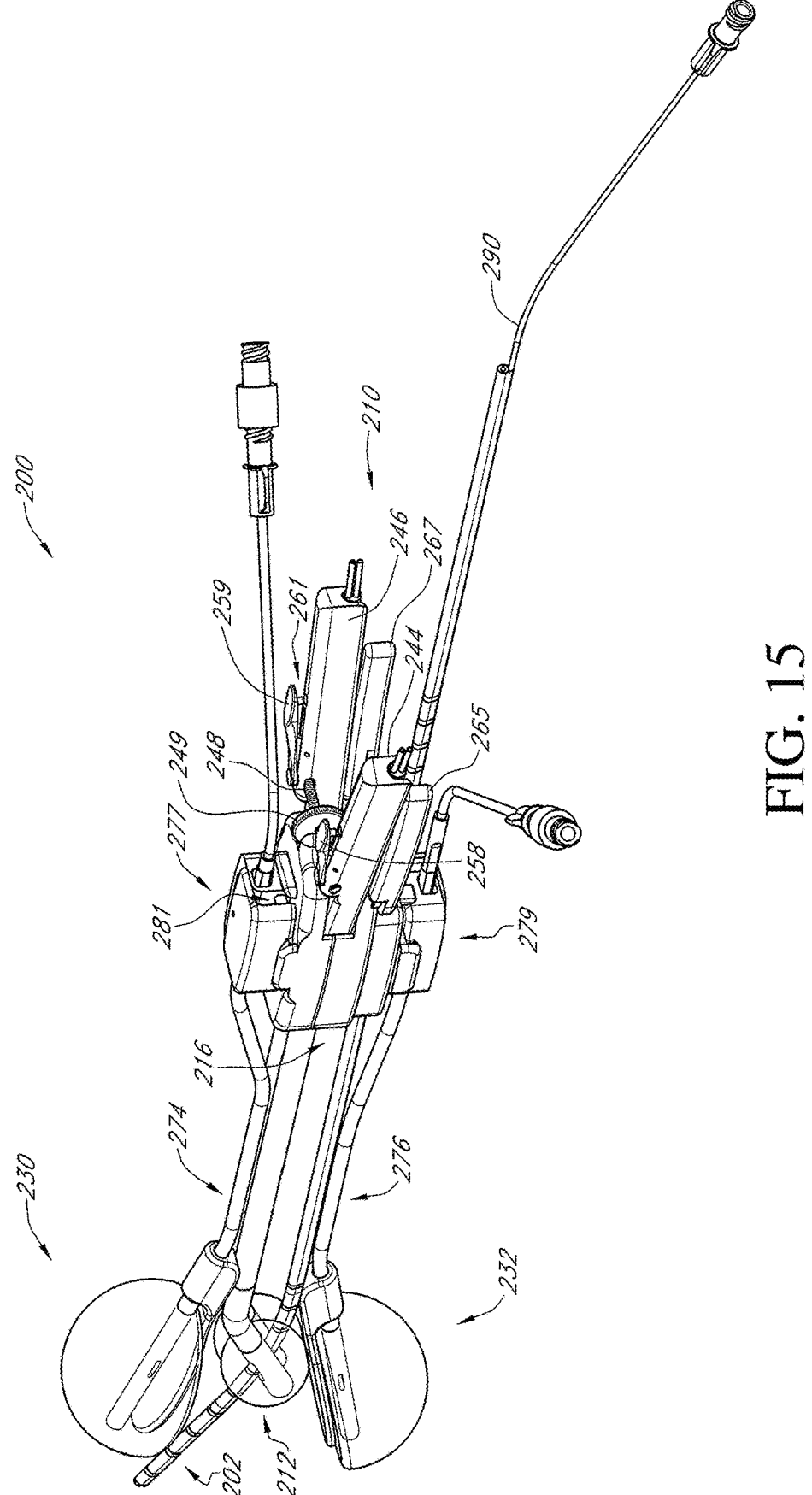
FIG. 15 illustrates a side perspective view of another assembled minimally invasive intracavitary brachytherapy applicator system according to embodiments of the present application.

With reference to FIG. 14, in some embodiments, a miniaturized endoscopic fiber optic bundle 190 is integrated with the tandem 102. In some embodiments, the fiber optic bundle 190 can be about 1 mm thick along the length of the tandem 102. The endoscope 104 can be illuminated by a battery operated LED light and connected to a CMOS or CCD camera. The images preferably can be seen on a display monitor or be captured in a laptop computer connected through a USB2 or USB3 connector, or other suitable connector, for further analysis. The eye piece can be attached to a coupler that can be attached to a CMOS or CCD camera and connected to a laptop computer or a display monitor. Endoscopic capabilities of the tandem 102 enables the physician to find the cervical os, guide the tandem into the cervical os and uterine canal, sound the uterus, and inspect the extent of the disease in vagina, cervix, uterine canal, and the uterus. The endoscope 104 can help the radiation oncologist to guide the tandem to the end of the uterine canal without perforating it. A mechanism, such as markings on the tandem 106, can be used to measure the length of the uterine canal from the cervical os to the end of the canal. This feature helps sound the uterine canal and position the flange on the tandem to limit the risk of the tandem perforating the uterus.

Methods of Use

In some embodiments, the applicator 100 comprises a tandem catheter adapted to be placed in the uterine canal with a cervical os stopper (e.g., a flange with a ring radiographic marker). The ovoid and retractable system assembly (collectively, ORSA) is preferably coupled prior to treatment to form an integrated unit as one part. The ORSA can be inserted after the tandem is in place. The tandem preferably slides through a central pivoting tract between the two ovoids of the ORSA. The ORSA is inserted inside the vaginal canal until it reaches the cervical fornices. A separator mechanism on the ORSA can be adjusted to open and separate horizontally the two ovoids and lock at the desired position with a locking knob. The inflatable ovoids can be filled with a mixture of water or saline, and 2% iodinated contrast solution through the luer lock for each ovoid. The luer locks can have a one way valve preventing the infused saline to leak out from the ovoids or the bladder and rectal retractor.

In some embodiments the ovoids are filled symmetrically. The saline volume will be dependent on the size of the fornices, and vaginal distal circumferential diameter. The inflatable ovoids are preferably made such that there is at least one cm distance posteriorly from the end of the catheter to the surface of the vaginal mucosa, thus lowering the dose to the vaginal mucosa and rectum. The adjustable volume of the ovoids and bigger diameter will conform to the shape of the fornices and improve the percentage depth dose to the tumor under treatment. The pivoting tandem mechanism can be fixed so the tandem bisects the ovoids and remains locked using a side locking knob. The square-shaped or flattened portion of the tandem is placed in the ovoid tract having a similar square-shaped or flattened configuration. This acts to limit the tandem from unwanted rotation in the uterine canal. Other shapes can be used to limit rotation of the tandem.

In some embodiments, one or both of the inflatable ovoids may be inflated with fluid (e.g., water, saline) that is warmed above a hyperthermic threshold and/or below a maximum critical threshold temperature. Additionally or alternatively, one or both of the retractors (e.g., bladder, rectal) may be filled with fluid that is cooled below a hypothermic threshold and/or above a minimum critical threshold temperature. Ovoids filled with such warmed fluid can support improved brachytherapeutic effects. This kind of thermoradiotheraphy may be used as a supplement/alternative for stage IIB-IV patients who, for example, are unable to receive the standard therapy of concurrent chemotherapy and radiotherapy (e.g. because of kidney failure). Achieving local and regional tumor control can be a challenge for locally advanced cervical cancers (e.g., FIGO stage IIB-IV). Alternative or additional to chemo-radiation is to include radiotherapy with hyper- and/or hypo-thermia treatment. For example, elevated body temperature can damage and even kill cancerous cells with minimal or relatively reduced injury to normal cells. Additionally or alternatively, lower body temperature can reduce blood flow to the area and may reduce the spread of toxic effects of radiotheraphy.

Hyperthermia can be an effective technique for cancer therapy by increasing tumor temperatures to above a hyperthermic threshold while staying below a maximum critical threshold temperature. The hyperthermic threshold can be about 38° C., about 39° C., about 40° C., about 41° C., about 42° C., about 43° C., about 44° C., about 45° C., about 46° C., about 47° C., any value therebetween, or fall within a range having any value therein as endpoints. For example, the hyperthermic threshold can be between about 40-45° C. in some embodiments. Using a hyperthermic threshold above, depending on the patient's own sensitivities and on other factors, locoregional hyperthermia combined with radiotherapy may be at least as effective in improving locoregional control for cervical tumors as chemoradiotherapy. The maximum critical threshold temperature can be about 52° C., about 53° C., about 54° C., about 55° C., about 56° C., about 57° C., about 58° C., about 59° C., about 60° C., about 61° C., any value therebetween, or fall within a range having any value therein as endpoints.

One advantage of hyperthermia that is given sequentially before or after radiotherapy is that an incidence of late toxicity grade 3 or higher may not be significantly different from the toxicity after treatment with radiotherapy alone. Although local tumor control under standard therapy (e.g., without thermal support) may be good, particularly if combined with image-guided brachytherapy, improved control of regional and distant disease and a reduction of side effects may be possible with thermoradiotherapy. Thus, hyperthermia may be effective in supporting radiotherapy in the embodiments described herein. The systems and methods described herein can apply hyperthermia and/or hypothermia before, during, and/or after brachytherapy by infusing fluid (e.g., water) heated and/or cooled to the target temperature, such as above the hyperthermic threshold described above but below the maximum critical threshold temperature, such as a temperature of about 45° C., into the ovoids positioned in the vaginal fornices next to or near the cervical cancer.

Additionally or alternatively, the bladder and/or the rectum balloon retractors can be infused with water (e.g., about 0° C.) to cool off the bladder and rectal walls to reduce the blood flow to these regions, thus lowering the blood flow and oxygenation to normal tissue while delivering the radiation dose. For hypothermia (e.g., in one or both of the retractors), the fluid may be cooled to below a hypothermic threshold but above a minimum critical threshold temperature. This can be done after a geometric position of the brachytherapy applicator is verified by endoscopic and CT image guidance some time (e.g., 30 minutes) prior to the radiation delivery. The hypothermic threshold can be about 0° C., about 1° C., about 2° C., about 3° C., about 4° C., about 5° C., about 6° C., about 7° C., about 8° C., about 9° C., any value therebetween, or fall within a range having any value therein as endpoints. For example, the hypothermic threshold can be between about 0-5° C. in some embodiments. The minimum critical threshold temperature can be about −5° C., about −4° C., about −3° C., about −2° C., about −1° C., any value therebetween, or fall within a range having any value therein as endpoints.

Both hyperthermia/hypothermia and brachytherapy can be advantageous for more effectively damaging the tumors and/or reducing the radiation toxicity to the organs at risk, thus increasing the therapeutic ratio, loco-regional tumor control, and minimizing morbidities due to radio toxicities. The external ovoid and/or retractor temperature can be monitored before and during radiation delivery. Additionally or alternatively, the fluid infused into the respective ovoid and/or retractor can be modified to adjust and/or maintain the temperature of the fluid toward a target temperature within the ovoids/retractors. Thus, the hyperthermic/hypothermic effects can be maintained and/or improved during a brachytherapeutic procedure.

The two inflatable retractors are filled with saline to retract the anterior and posterior wall of the vaginal canal from the plane of the implant. The retractors can be filled symmetrically in some embodiments. The volume of the saline is adjusted to preferably have at least two cm retraction from the plane of the tandem. An advantage of an embodiment wherein the inflatable retractors are made of soft polyurethane semi-cylindrical or disc-shaped balloons is that the patient will feel less pain and little pressure. Since insertion of the tandem is followed by the insertion of the assembled single piece ovoid and retractor assembly, the implant time is much shorter compared with devices that require assembly of several components in the patient. Accordingly, patient discomfort and pain is minimal, lowering the need for complete and prolonged anesthetics. Due to adjustable features of the applicator, most of the positioning and adjustments is done remotely outside uterus, cervix, and vagina, making it minimally invasive, lowering patient pain and discomfort and number of personnel required for assistance.

In some embodiments, the applicator is designed to have markers every one centimeter for radiographic identification and has magnification factors readily available for dose calculations. The disposable material made of high strength plastics (Peek, GlassPeek, Carbon Fiber) or lightweight stainless steel has minimal radiation self-absorption, removing the need for dosimetry corrections. The total length of the three catheters is preferably substantially identical to limit human errors during dosimetry calculations. In one embodiment, the applicator is designed such that the right ovoid will be connected through a transfer guide tube to channel one, the left ovoid to channel two, and the tandem to channel three of a commercially available 192-Ir HDR or Co-60 afterloader. In some embodiments, the tandem and ovoid system preferably comprises CT and MRI friendly material, making 3D dosimetry possible with no image artifacts.

Once the applicator is removed, the patient can then be allowed to heal. Advantageously, with the use of the applicator systems described herein, the recovery time is reduced compared to conventional treatments due to the improved dosimetry and limited invasiveness of the treatment.

Additional Features and Advantages of Some Embodiments

FIGS. 15-18 illustrate another assembled minimally invasive intracavitary brachytherapy applicator system according to embodiments of the present application. The applicator system of FIGS. 15-18 is similar in some respects to the systems and embodiments illustrated and described with reference to FIGS. 1-14. Some additional features and advantages are described below.

With reference to FIGS. 15-18, according to some embodiments, systems for treating cervical and/or uterine cancers in brachytherapy with an intracavitary brachytherapy applicator 200 comprise a tandem 202 adapted for insertion into a cervix of a patient. The tandem 202 can comprise an endoscopic viewing element 204 to facilitate treatment and one or more radiographic markers 206.

An ovoid assembly 210 comprises first and second adjustably inflatable ovoids 212, 214 and an ovoid support mechanism 216. The ovoid support mechanism 216 is adapted to support the ovoids 212, 214 and to allow for user manipulation to control the relative position of the ovoids for insertion of the ovoids within the fornices of a patient. The first and second adjustably inflatable ovoids 212, 214 have a deflated configuration for insertion into a patient and one or more adjustably inflated configurations for positioning the ovoid assembly during treatment. The first and second ovoids 212, 214 may have one or more radiographic markers. The ovoid assembly 210 comprises a tandem connector 224 adapted to releasably and adjustably couple the tandem 202 to the ovoid assembly 210 to allow for pivotal and translational motion of the tandem 202 relative to the ovoid assembly 210 and to limit rotational movement of the tandem 202 about a longitudinal axis of the tandem.

First and second adjustably inflatable retractors 230, 232 are adapted to be releasably coupled to the ovoid assembly at first and second retractor connector portions 234, 236. The first and second inflatable retractors 230, 232 have a deflated configuration for insertion into a patient and an adjustably inflated configuration for retraction of tissue during treatment. The first retractor 230 is adapted to be positioned to retract the bladder of a patient during treatment and the second retractor 232 is adapted to be positioned to retract the rectum of a patient during treatment. The tandem 202 and the first and second inflatable ovoids 212, 214 are adapted to be coupled to a radioactive source to deliver an implant radiation dose suitable for cancer treatment at a cancerous cervical treatment site in a patient.

Some embodiments are described in more detail below. The applicator systems and methods can have one or more of the following advantageous characteristics in some embodiments. For example, the applicator system of FIGS. 15-18 preferably has a configuration that makes the applicator system easier to implant, less invasive and traumatic for the patient, or provides improved inter-fraction implant geometric reproducibility by including one or more of the following features and functionalities in the system.

The ovoid support mechanism 216 is adapted to support the ovoids 212, 214 and to allow for user manipulation to control the relative position of the ovoids for insertion of the ovoids within the fornices of a patient. The ovoid support mechanism 216 supports first and second catheter shafts 240, 242 coupled with the ovoids for delivering radiation to the ovoids. The ovoid support mechanism 216 also comprises first and second handle portions 244, 246 coupled for pivotal movement relative to one another. Movement of the handle portions 244, 246 relative to each other controls the distance between the first and second ovoids 212, 214. The ovoid support mechanism 216 comprises a threaded shaft 248 extending between the first and second handle portions 244 and 246. An adjustment wheel 249 is coupled to a central portion of the threaded shaft 248.

The first and second handle portions 244 and 246 comprise first and second knobs 258, 259 coupled to the handle portions and configured to be coupled to the threaded shaft 248. In some embodiments the knobs comprise tabs or levers that are pivotally coupled to the handle portions and that are disposed in a first configuration wherein a spring 261 located between the handle portion and a proximal portion of the knob urges a distal portion of the knob into engagement with the threaded shaft 248. With the knobs in the first engaged configuration, the adjustment wheel 249 can be rotated by a user. Rotation of the threaded shaft 248 provides for fine adjustment to move the handle portions toward or away from each other, to precisely control the relative movement, position, and separation of the of the ovoids 212, 214. Additionally, the knobs have a second unengaged configuration. A user can press down on a proximal portion of the tab or lever against the spring force such that a distal portion of the knob disengages with the threaded shaft. In the disengaged configuration, the user is free to make large adjustments to the movement, position and separation of the ovoids by moving the handle portions toward or away from each other. Thus, the threaded shaft and knob features provide for quick and large adjustments in position by disengaging the knob from the threaded shaft, while allowing for precise control over the movement and positioning of the ovoids in an engaged configuration when the knob features are released and the spring forces the knob features into engagement with the threaded shaft. The relative position of the handle portions 244, 246 can be fixed relative to the ovoid support mechanism 216 by releasing or positioning the knobs to allow the knobs to engage with the threaded shaft 248. Accordingly, in some embodiments, the two knobs on the ovoid handles can be pressed to allow the two ovoid balloons to be separated horizontally in a coarse adjustment mode. In some embodiments, the adjustment wheel between the two ovoid handles allows the two ovoid balloons to be adjusted horizontally in a fine adjustment mode.

A lower portion of the ovoid support mechanism 216 comprises the tandem connector 224. In some embodiments, the tandem connector is a flexible clip. The tandem connector 224 preferably comprises a slot 252 for receiving the tandem 202. In some embodiments, the tandem connector has a generally horse-shoe-shaped cross-section. The tandem connector can be configured to grip the tandem to allow for translational and pivotal coupling of the tandem to the ovoid support mechanism.

The tandem connector 224 is preferably coupled to the ovoid support mechanism 216 such that the tandem connector can pivot relative to the ovoid support mechanism in some configurations and be clamped in position in other configurations. In some embodiments, the ovoid support mechanism comprises one or more handles 265, 267 operatively coupled with the tandem connector. When the one or more handles are positioned in a first open configuration, the tandem connector 224 can receive and hold a tandem and allow for movement of the tandem distally and proximally, and also allow for pivotal movement of the tandem and tandem connector relative to the ovoid support mechanism. The configuration of the tandem connector when engaged with the tandem preferably limits rotation of the tandem about a longitudinal axis of the tandem. When the one or more handles are positioned in a second clamped position, the tandem connector is compressed within the ovoid support mechanism 216 such that the tandem connector and tandem are generally held in position to limit movement distally or proximally, and to limit pivotal movement. Accordingly, positioning and adjustment of the tandem relative to the ovoid support mechanism is facilitated with the one or more handles in an open configuration and when a desired positioning has been achieved by the user, the one or more handles can be moved to the closed configuration to hold the tandem in the desired orientation.

Figure 16:
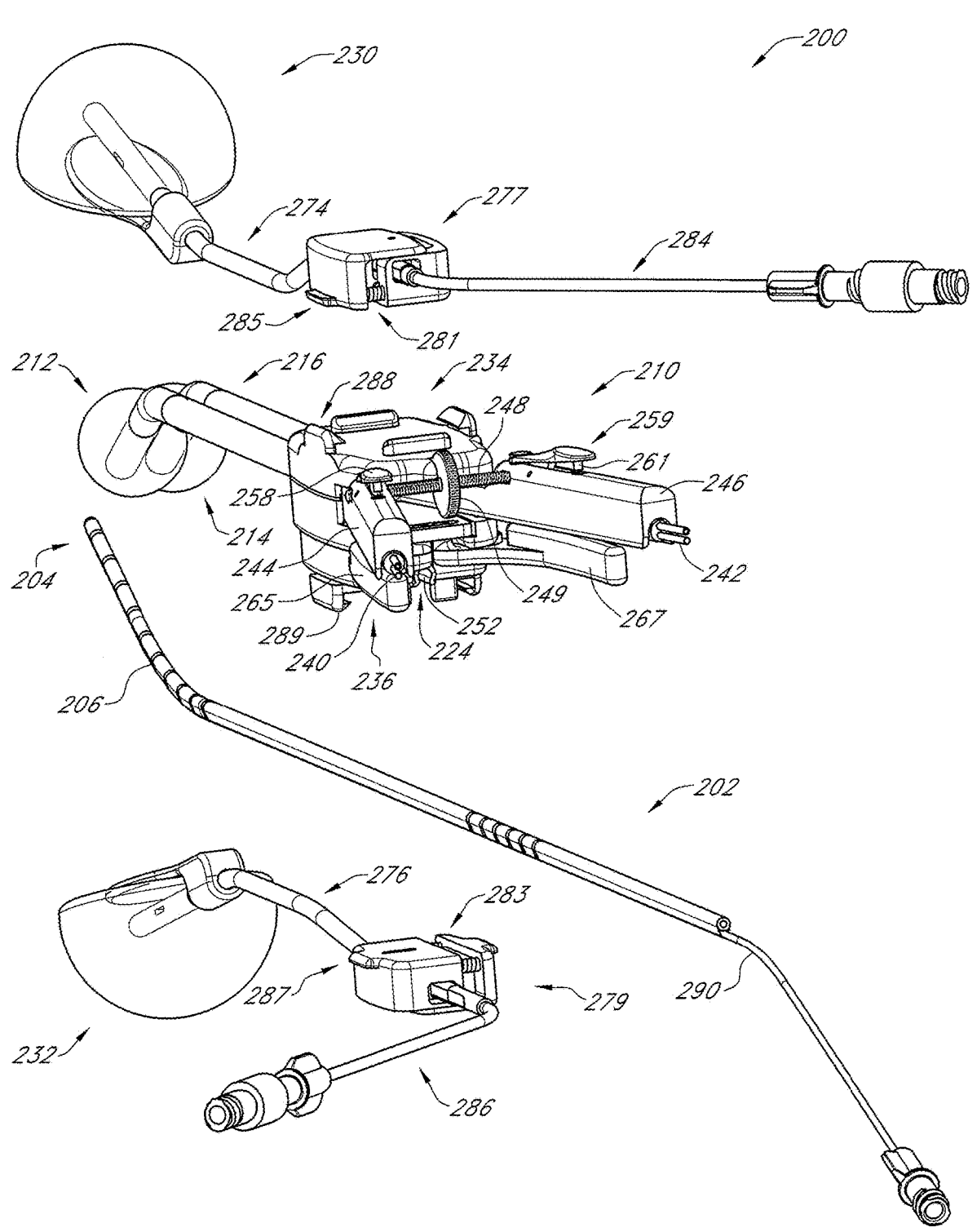
FIG. 16 illustrates an exploded view of the applicator system of FIG. 15.
Figure 17:
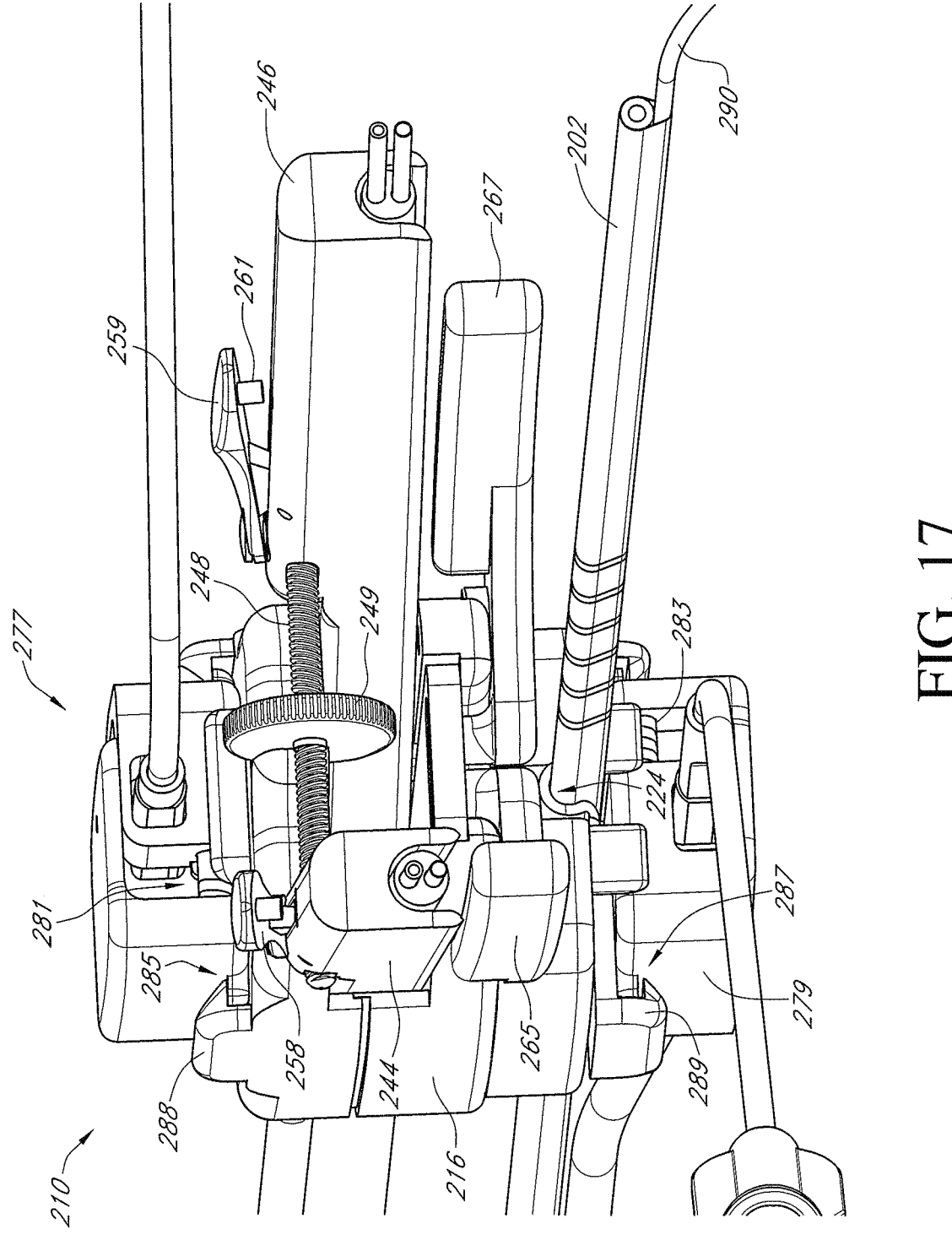
FIG. 17 illustrates rear side perspective view of the applicator system of FIG. 15 according to embodiments of the present application.
Figure 18:
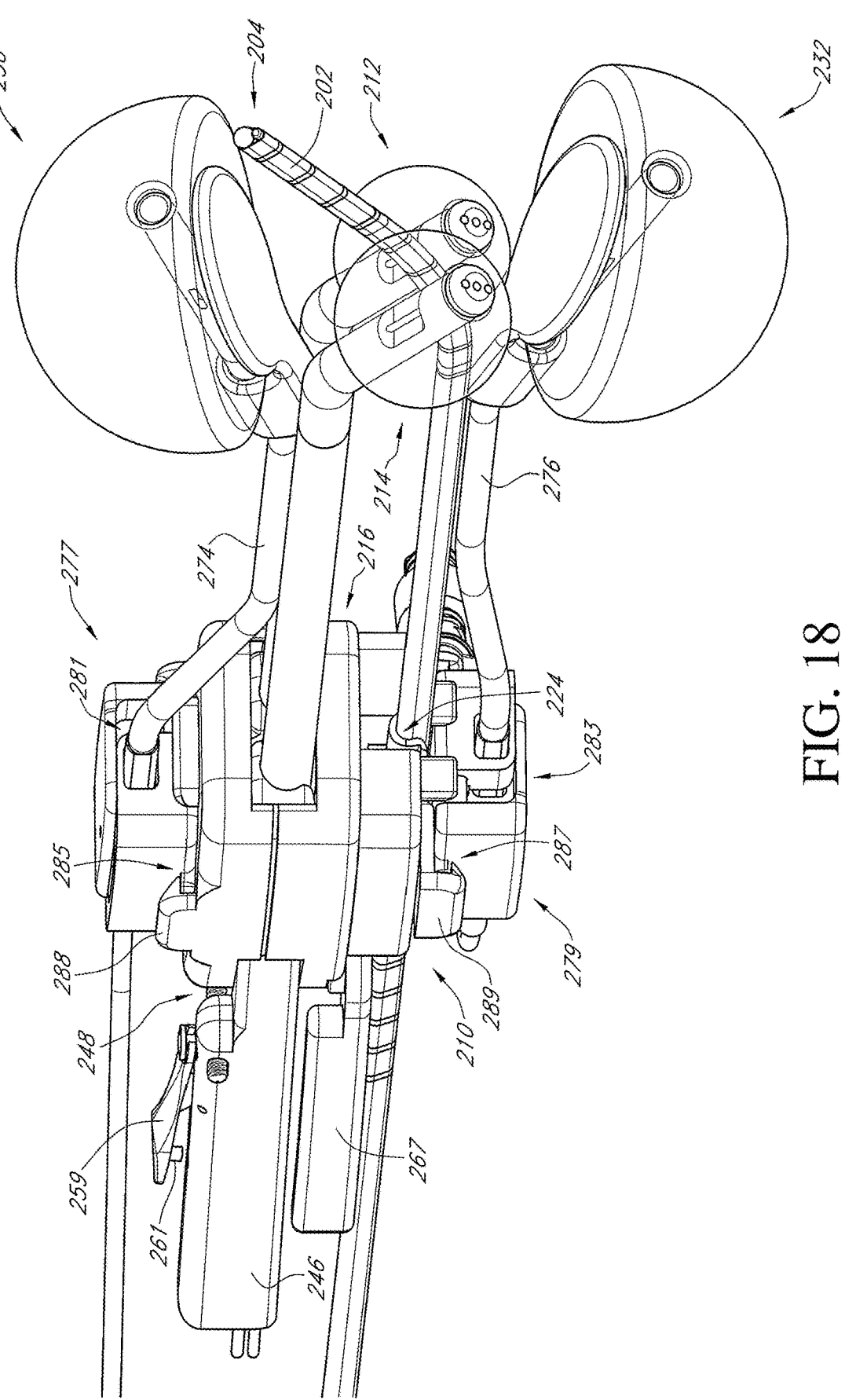
FIG. 18 illustrates a front side perspective view of the applicator system of FIG. 15 according to embodiments of the present application.

As mentioned above, a tandem connector 224 mechanism is provided for coupling the tandem 202 with the ovoid assembly 210. The mechanism preferably enables the tandem 202 to pivot in the anterior/posterior direction about a point in reference to the ovoids 212, 214 using a clip and clamping mechanism within the ovoid assembly 210 to interface with the tandem as best seen in FIGS. 16-18. The mechanism also preferably allows the user to translate and/or pivot the tandem to keep it at the mid-plane of the ovoids 212, 214 during treatment. Enabling the user to position the tandem 202 to bisect the ovoids 212, 214 helps to improve implant geometry and dose distribution. In some embodiments, the tandem is arranged to limit inadvert rotation of the tandem 202 during manipulation and treatment. Accordingly, the mechanism preferably limits the tandem from rotation around a longitudinal axis of the tandem and permits translational and pivotal motion to achieve an advantageous mid-plane position relative to the ovoids 212, 214.

Retractor balloons 230, 232 are preferably added to the intracavitary brachytherapy applicator 200 to retract the bladder and the rectum from the radiation sources, thus lowering the dose to these critical structures. This can reduce, and in some cases eliminate, the need to use of vaginal packing after the applicator is in place. The retractor balloons 230, 232 are coupled to catheters 284, 286 that are preferably anchored on the ovoid assembly 210. The retractor balloons 230, 232 are preferably inflated with saline. Other suitable inflation mediums can also be used. The balloons can be hemispherical when inflated to push the vaginal mucosa, bladder, and rectum away from the radiation site. Balloons having other suitable shapes and sizes for providing retraction can also be used. The retraction mechanism is preferably inflatable to retract the bladder and the rectum by at least about 2 cm away from a plane of the implant defined at the plane of the tandem bisecting the ovoids. The retraction mechanism preferably retracts equidistance from the plane of the implant. The retraction mechanism comprises balloons 230, 232 and retractor supports 274, 276 coupled to the ovoid assembly 210 at retractor connection portions 234, 236. The bladder and rectum retractor balloons preferably have attachment mechanisms 277, 279 that allow for the lengths of the retractor supports 274, 276 to be adjusted. By pressing a spring actuated lock mechanism 281, 283 on the attachment mechanisms 277, 279, the retractor supports 274, 276 can be moved proximally or distally relative to the attachment mechanisms for the desired length corresponding to the length of the vaginal canal. When the spring actuated lock mechanism 281, 283 is released, the retractor supports 274, 276 are held in position and preferably do not move proximally or distally while in the locked position. After insertion of the retractor, the attachment mechanism 277, 279 can be removably coupled to the ovoid assembly 210. In some embodiments, the attachment mechanism can be coupled to the ovoid assembly by pressing the attachment mechanism against the ovoid assembly 210. The ovoid assembly preferably has tabs 285, 287 that engage with tabs 288, 289 on the attachment mechanism 277, 279. As the attachment mechanism is pressed against the ovoid assembly, the tabs 288, 289 on the ovoid assembly preferably engage the tabs 285, 283 on the attachment mechanism such that the spring actuated lock mechanism 281, 283 compresses to allow the tabs on the attachment mechanism snap into place between the tabs on the ovoid assembly and a surface of the ovoid assembly in a configuration similar to a key-lock attachment. Both the bladder and the rectal balloons can have similar attachment configurations to adjust for the length of the vaginal canal by pressing the spring-actuated locking mechanism similar to a key-lock attachment. In some embodiments, the bladder retractor is preferably filled with air or a gas to push away the bladder from the radiation sources. Compared with a liquid, this may limit the retractor from leaning over the tandem and ovoid due to its weight or gravity to displace or change its optimal geometry. The rectum retractor is preferably filled with saline to push away the rectum from the source of radiation. The saline weight due to gravity will push away the rectum from the sources of radiation. In some embodiments, both retractors are suitable to be filled with either a gas or a liquid, such as for example, air or saline.

With reference to FIGS. 15-18, in some embodiments, a miniaturized endoscopic fiber optic bundle 290 is integrated with the tandem 202. In some embodiments, the fiber optic bundle 290 can be about 1 mm thick along the length of the tandem 202. An endoscope can be illuminated by a battery operated LED light and connected to a CMOS or a CCD camera. The CMOS or CCD endoscope can also be illuminated by about 120 fiber optic fibers surrounding the CMOS chip connected to a PC board and a laptop USB2 connector. In some embodiments, the tandem may have a high resolution fiber optic bundle of up to 10000 pixels, or more, for finding the cervical os, connected to a CCD or CMOS high resolution camera. The CCD or CMOS camera output may be connected to a laptop computer via USB2 or USB3 connector, or another connector, or wirelessly connected, to display static and/or video images of the cervix, cervical os, and uterine canal. The camera may be used for image guidance to find the cervical os, or to guide the tandem into the uterine canal all the way to the end without perforating the uterus. In some embodiments, an alternative configuration to the optical fiber bundle-camera is a miniaturized ultrasound transducer to perform these or other functions and that is configured to be attached to a display to view the ultrasound pictures of the cervical os, uterine canal, and evaluate the extent of disease and boost the radiation dose in the areas with gross cancerous tumor or evaluate the response of cancer to treatments.

Visualization capabilities of the tandem 202 enables the physician to find the cervical os, guide the tandem into cervical os and uterine canal, sound the uterus, and inspect the extent of the disease in vagina, cervix, uterine canal, and the uterus. The visualization can help the radiation oncologist to guide the tandem to the end of the uterine canal without perforating it. A mechanism, such as markings on the tandem 206, can be used to measure the length of the uterine canal from the cervical os to the end of the canal. This feature helps sound the uterine canal and position the flange on the tandem to limit the risk of the tandem perforating the uterus.

In some embodiments, methods of using the applicator 200 are similar to methods described previously in connection with other embodiments. With reference to FIGS. 15-18, in some embodiments, handles on the ovoid assembly can be adjusted to open and separate horizontally the two ovoids and lock at the desired position. In some embodiments, the two knobs on the ovoid handles can be pressed to allow the two ovoid balloons to be separated horizontally in a coarse adjustment mode. In some embodiments, the adjustment wheel between the two ovoid handles allows the two ovoid balloons to be adjusted horizontally in a fine adjustment mode. The inflatable ovoids can be filled with a fluid. The pivoting tandem mechanism can be adjusted or fixed so the tandem bisects the ovoids and remains locked using a tandem handle clamping mechanism. The two inflatable retractors are filled with fluid to retract the anterior and posterior wall of the vaginal canal from the plane of the implant. The length and positioning of the retractors can be adjusted by pressing the spring actuated lock mechanism and manipulating the retractor supports to the desired length relative the attachment mechanism. The attachment mechanism for the retractor can be pressed against the ovoid assembly to snap the retractors into position. Due to adjustable features of the applicator, most of the positioning and adjustments is done remotely outside uterus, cervix, and vagina, making it minimally invasive, lowering patient pain and discomfort and number of personnel required for assistance. Visualization of the procedure can be made as described above. Once the applicator is removed, the patient can then be allowed to heal. Advantageously, with the use of the applicator systems described herein, the recovery time is reduced compared to conventional treatments due to the improved dosimetry and limited invasiveness of the treatment.

Figure 19:
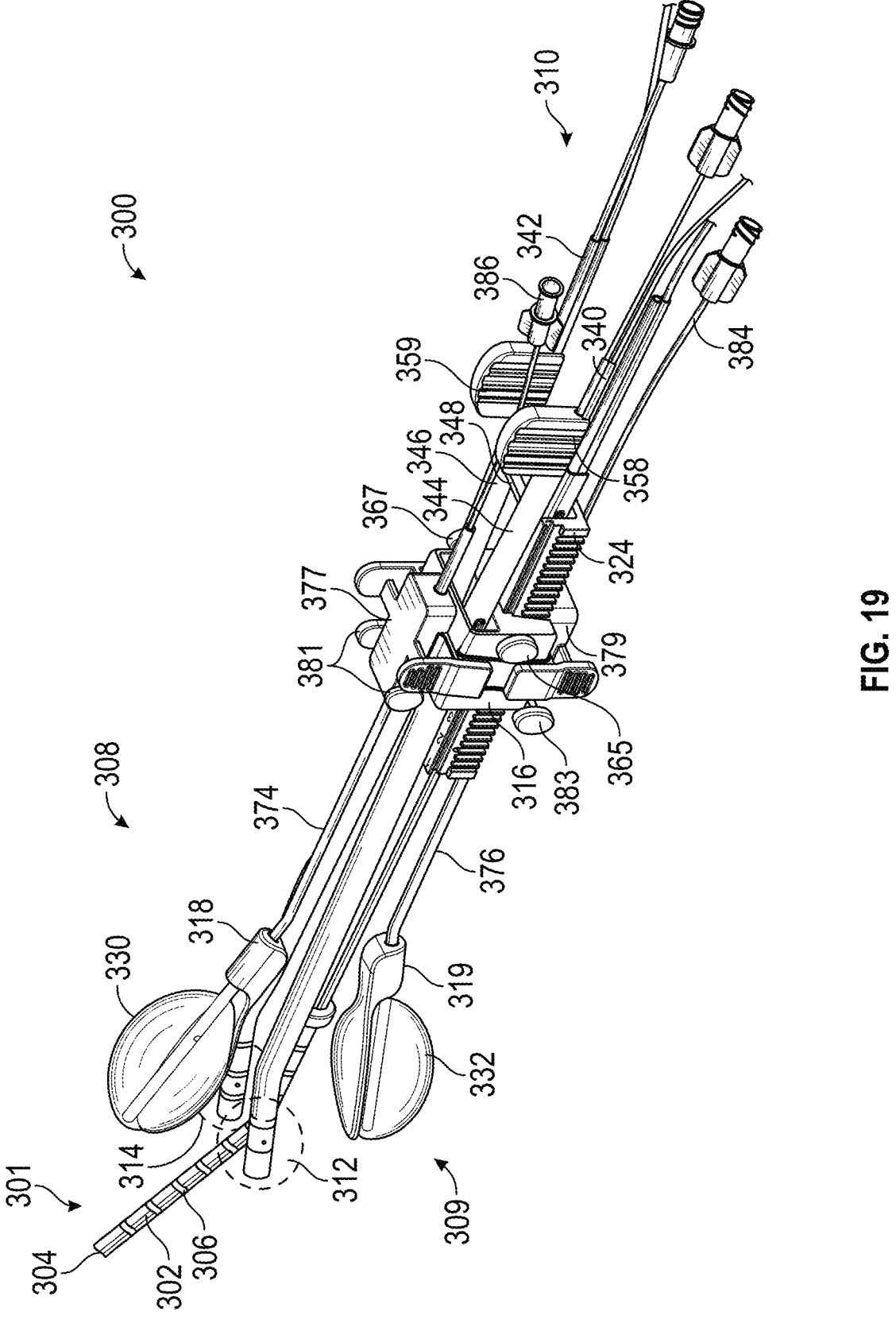
FIG. 19 shows a perspective view of an example applicator.

FIGS. 19-26 show various aspects of elements of another example applicator 300, according to one embodiment. FIG. 19 shows a perspective view of an example applicator 300. It may be advantageous to include a compact applicator 300 that is comprised of a manageable number of elements that can be coupled and uncoupled together. The applicator 300 can allow for easy access of the various features offered by the applicator 300. For example, the applicator 300 may include a unidirectional adjustment interface among one or more of the elements. Additionally or alternatively, the applicator 300 may include a grooved tandem connector 324. In some embodiments, the applicator 300 can include other advantages, such as a tandem connector 324 that is configured to receive the tandem 302 within an interior of the tandem connector 324. Other variants are possible.

One beneficial aspect is that the tandem 302 may contain an integrated holder for the addition of an endoscope. Thus as the applicator is advanced, the user may be able to visibly orient to anatomical landmarks within the vaginal vault. Endoscopic visualization of the cervical canal and os can reduce the need to use a speculum. Further, direct visualization of the pathological anatomy can improve placement of bladders used to protect surrounding organs (i.e. rectum and bladder). The tandem 302 may include a utility channel in which a miniaturized multi-frequency ultrasound imaging system can be inserted. The imaging system may be used for Intravascular Ultrasound Imaging (IVUS) and may be incorporating a higher frequency transducer (e.g., 80 to 150 MHz) with the conventional IVUS (30-50 MHz) system. The ultrasound transducer may be used for additional image guidance through the cervical os and uterine canal. The ultrasound imaging may have a diameter of less than 2 mm (e.g., 0.9 mm) to help identify the cervical os, gross abnormalities, and cancer tissues not responded to chemotherapy and external beam radiotherapy to boost these areas with our brachytherapy applicator. The ultrasound imaging and/or the optical imaging using CMOS or alternative camera types with fiber bundles may be used simultaneously in a multi-channel (e.g., three channel) tandem or be used one at a time utilizing the tandem's utility channel.

An ultrasonic imaging and CMOS camera visualization system for hysteroscopy may be used to more accurately diagnose and position the applicator next to any abnormalities in the cervix and/or the uterine cavity to make immediate treatment possible. Narrow-lumen tandem with hysteroscopy capabilities may enable procedures to be performed outside the Operating Room without anesthesia or dilation of the cervix. Furthermore, hysteroscopy can be used to rule out any obstacles to implantation prior to brachytherapy treatment. Further, the imaging systems can reduce the likelihood that the tandem will perforate the uterus, preventing a potentially damaging radiation dose from being delivered to the small bowel or preventing an infection caused by the perforation.

In some embodiments, a tandem with imaging capabilities may have a diameter of less than about 5 mm (e.g., about 3 mm), which may allow an atraumatic primary approach to the cervical and uterine cavity brachytherapy under visualization. In some embodiments, an LED may be supplied to shine light on tissue, for example near the endoscopic viewing element 304. A monitor, light source, camera control unit and data management system may be included in a single unit to provide a portable, mobile solution to an image guided brachytherapy of cervical and/or uterine cancers using a disposable tandem and inflatable ovoids with an imaging software with video or still image recording capabilities.

With continued reference to FIG. 19, the applicator 300 can include a tandem assembly 301, an ovoid assembly 310, a first retractor assembly 308, and/or a second retractor assembly 309. The tandem assembly 301 can include a tandem 302 and/or a tandem connector 324. The ovoid assembly 310 can include an ovoid support mechanism 316, one or more handle portions 344, 346, one or more adjustment mechanisms 358, 359, and/or corresponding one or more ovoids 312, 314. The first retractor assembly 308 can include corresponding elements, such as a first attachment mechanism 377, a first retractor support 374, a first retractor balloon support 318, and/or a first inflatable retractor 330. The second retractor assembly 309 can include corresponding elements, such as a second attachment mechanism 379, a second retractor support 376, a second retractor balloon support 318, and/or a second inflatable retractor 332.

The tandem assembly 301 can provide a useful tool for accurately and/or easily managing the relative location of the tandem 302 to the rest of the applicator 300 and/or to the patient's body. The tandem 302 may include one or more segments. For example, a longitudinal segment may define a longitudinal axis of the applicator 300. An angled segment of the tandem 302 may be attached to the longitudinal segment and may form an angle with the longitudinal section. This angle may be configured for easier and/or safer insertion into the fornices of a patient. The angle may be obtuse (e.g., between about 130° and) 170°. The tandem 302 may include an endoscopic viewing element 304 configured to allow a care provider to view tissue at or near the tip of the tandem 302 to provide treatment more accurately to the target location. The tandem 302 may include one or more radiographic markers 306. The radiographic markers 306 may be disposed at regular intervals from each other. The interval may be any interval, such as about 0.1 cm, 0.5 cm, 1 cm, 2 cm, 3 cm, 5 cm, 10 cm, or any interval within a range having any pair of these values as endpoints. The radiographic markers 306 may be disposed on the angled portion, the longitudinal portion, or both.

The tandem 302 may include one or more (e.g., one, two, three, four, five, or more) lumens for various purposes. For example, an ultrasonic transducer may be included in a utility channel of a dual lumen tandem to find the cervical os as well as diagnose the bulky tumors locations to escalate the radiation dose in these regions for improved local control. In some embodiments, the tandem 302 could comprise three lumens, one for the radiation source, simultaneous imaging using the second and third lumens for the CMOS camera, and a miniaturized ultrasonic transducer to improve positioning of the tandem without perforation of the uterus and improve diagnosis of regions that have not responded to chemo and external beam radiation therapies. A miniaturized ultrasound transducer with dual frequencies may be used with an outer diameter of less than 2 mm (e.g., 0.95 mm) may be included.

In some embodiments, a three lumens extrusion may be used for the tandem. A first lumen may be for the CMOS camera with fiberoptic bundles to carry LED light, laser light, and/or a fiberscope. A second lumen may be used for an ultrasound transducer. A third lumen may include a utility channel to deliver the radiation source (e.g., Ir-192, Cs-137, Co-60, etc.). Alternatively, as noted above, a dual lumen tandem 302 may be used. A first lumen may be used for dose delivery, and a second lumen may be used for optical imaging and/or ultrasound imaging to lower the external diameter of the tandem 302. The CMOS camera may be installed on a multi-lumen (e.g., dual-lumen) catheter with markers at regular intervals (e.g., at 1 cm intervals) to treat cancers of Esophagus, Trachea, Bronchi, Liver, Gall bladder, etc. The treatment can be image-guided to identify blocked or narrowed regions to boost the radiation dose and to position the radioactive source in proximity to those regions. The camera(s) may have a resolution of at least 160K at a 1.6 mm diameter or a 40K resolution in 0.65 mm square modules and may be manufactured by Fujikura. Other variations are possible.

A dedicated endoscopic system may be used to evaluate the geometry of the applicator post implant without the use of speculum. Such minimally invasive techniques can allow for an image-guided adjustment of the applicator and/or the balloon retractors 330, 332 to reproduce the implant between fractions. This approach may reduce the need for using repetitive x-rays, CT, and/or MR scans to modify an imperfect implant.

A multi-lumen (e.g., five lumen) design may be used for one or more of the ovoids 312, 314, for example to selectively and differentially deliver dose to areas closest to the lesion while reducing dose to the organs at risk (OARs). For example, two central lumens may be used where one is used for the water infusion to inflate the ovoid balloon while the other is used for radiation delivery in the central channel. Two additional channels may be used for delivery of the radiation delivery. Other combinations and configurations are possible with multi-lumen configurations.

The tandem 302 may fit within an interior of the tandem connector 324 along the longitudinal axis. The tandem connector 324 may allow for secure coupling of the tandem 302 and may allow for various height and/or longitudinal configurations (e.g., see FIG. 23).

With continued reference to FIG. 19, the ovoid assembly 310 may include handle portions 344, 346 that fit within an interior of the ovoid support mechanism 316. The ovoid support mechanism 316 may be configured to be releasably coupled to the tandem connector 324. For example, the tandem connector 324 may include a plurality of grooves or slots distributed longitudinally along the tandem connector 324. The ovoid support mechanism 316 may include corresponding coupling elements (e.g., protrusions) for fitting within the grooves. This arrangement can allow for reduced likelihood of slippage between the coupling between the tandem connector 324 and the ovoid support mechanism 316. Tandem holder locking mechanisms 365, 367 can be included on the ovoid support mechanism 316 to allow a user to quickly and easily lock the ovoid support mechanism 316 to the tandem connector 324. The tandem holder locking mechanisms 365, 367 may be laser etched with indicators, such as "Push to Lock" for easy reference to their function. The first tandem holder locking mechanism 365 may be released by pressing them together a second time. Additionally or alternatively, the tandem holder locking mechanisms 365, 367 may be released through manual releasing (e.g., pulling one or both of them away from each other). The tandem holder locking mechanisms 365, 367 can be configured to ensure a friction and/or toothed coupling between the ovoid support mechanism 316 and the tandem connector 324.

The handle portions 344, 346 may include corresponding adjustment mechanisms 358, 359 (e.g., tabs, buttons, etc.). The first adjustment mechanism 358 may be coupled with the second adjustment mechanism 359 at an adjustment interface 348. The adjustment interface 348 may include a unidirectional adjustment interface (e.g., a one-way ratchet). The adjustment interface 348 may include a plurality of interlocking teeth.

In some embodiments, the ovoid assembly 310 may be in a first configuration (e.g., a "closed" configuration) for insertion into the patient. The ovoid assembly 310 may be manually adjusted to a second configuration (e.g., "open" configuration) once the applicator 300 is at least partially inside the patient. The applicator 300 may be configured for transition between the first and second configurations by use of the adjustment mechanisms 358, 359. For example, a user may pinch the adjustment mechanisms 358, 359 toward each other to open the ovoids 312, 314 (e.g., move the ovoids 312, 314 away from each other). As the adjustment mechanisms 358, 359 are manipulated, the ovoids 312, 314 may be configured to move angularly about a focal point. The focal point may be disposed at or within the ovoid support mechanism 316. The ovoids 312, 314 may each be configured to sweep an angle of greater than 3° and/or less than 45° (e.g., about 5°, 10°, 15°, etc.). In some embodiments, the relative position of the handle portions 344, 346 relative to the ovoid support mechanism 316 may be fixed. For example, the handle portions 344, 346 may be configured to pivot about an axis intersecting the ovoid support mechanism 316 through the tandem connector 324.

The ovoid support mechanism 316 is adapted to support the ovoids 312, 314 and to allow for user manipulation to control the relative position of the ovoids for insertion of the ovoids within the fornices of a patient. The ovoid support mechanism 316 supports first and second catheter shafts 340, 342 coupled with the ovoids for delivering radiation to the ovoids. The ovoid support mechanism 316 also comprises first and second handle portions 344, 346 coupled for pivotal movement relative to one another, as noted above. Movement of the handle portions 344, 346 relative to each other controls the distance between the first and second ovoids 312, 314. The ovoids 312, 314 may be adjustably inflated and may have common functionality with one or more features of the inflatable ovoids 212, 214. The ovoids 312, 314 may include one or more radiographic markers 306, such as may be found on the tandem assembly 301. The radiographic markers may be disposed at regular intervals from each other, such as about 0.1 cm, 0.5 cm, 1 cm, 2 cm, 3 cm, 5 cm, 10 cm, or any interval within a range having any pair of these values as endpoints. Additionally or alternatively, the radiographic markers 306 may be disposed on other portions of the ovoid assembly 310.

The ovoids 312, 314 may be made into straight or angled. For example, one or both may be facing down towards the rectum or facing up toward the bladder. Angled ovoids 312, 314 may be advantageous, for example, if the rectal dose needs to be lowered (e.g., the ovoids 312, 314 may be configured to face upward). This may lower a maximum rectal dose by as much as 25%. Based on the American Brachytherapy Society recommendations, the bladder dose tolerance may be 90 Gy to 2 cc volume while the rectal dose tolerance may be 75 Gy to 2 cc volume. Therefore, using one or more angled ovoids 312, 314, the dose to the lesion may be increased while simultaneously meeting the dose tolerance criteria for the rectum, which tends to be a more radiosensitive organ.

Without being limited by theory, it is estimated that about 25% of patients have a retroverted uterus while the other 75% of patients have an anteverted uterus. To implant and lower the dose to the organs at risk, it may be beneficial for the tandem 302 to follow the uterine canal and the ovoids 312, 314 to bisect the tandem 302. It may be beneficial, for example, for the ovoids 312, 314 to face up for the retroverted uteri. However, mechanical limitations of existing systems do not adequately allow for this type of treatment. The embodiments described herein can allow for the radiation oncologist to implant the ovoids 312, 314 facing towards the bladder for improved dosimetry. In many retroverted uteri, the ovoids 312, 314 can be implanted facing up towards the bladder to reduce the dose to the rectum by up to 10% or 15%. The appropriate orientation of the ovoids 312, 314 for each case may be determined by a radiation oncologist after conducting an evaluation of the patient's anatomy after beam radiotherapy.

The retractor assemblies 308, 309 may be configured for releasable coupling to the tandem assembly 301 and/or the ovoid assembly 310. Design of the tandem and ovoid assemblies may employ modular systems so that each modular element (e.g., the tandem assembly 301, the ovoid assembly 310, and/or the retractor assemblies 308, 309) may be stacked on top of each other without using any screws or knobs.

Other benefits can apply to one or more embodiments described herein. As one example, one or more components of the applicator 300 may be formed (e.g., molded, printed) of any CT- and/or MRI-friendly materials. For example, the various components may comprise plastic or other polymer. Thus either or both imaging modalities may be used to verify the position of the applicator itself, verify correct placement of the radiation source, and/or to perform 3D dosimetry. The tandem and ovoids proposed herein can be made to be packaged and sterilized as a disposable complete applicator set to be used for one time use only. The tandem and/or ovoid assemblies can be configured to prevent the transmittance of human papillomavirus (HPV) and other viral disease or pathogens between the patients due to incomplete and inadequate sterilization of reusable tandem and ovoid applicators. There are reports of endoscopic systems in the studies of upper and lower GI and transmittance of pathogens to other patients with the reusable endoscopic systems in the literature. For example, the embodiments described herein can help reduce the incidence that patients become sick by inadequate sterilization of endoscopic reusable systems between patients.

Other advantages include a design of the inflatable retractors 330, 332. For example, the inflatable retractors 330, 332 can be configured, in applicable circumstances, to lift a bladder that is wrapping around the cervix. A dose of therapy can be improved using a dosimetric software algorithm configured to improve the dose distribution while reducing dose to the organs at risk (OARs) based on source activity, tandem length, ovoid volumes, and/or the dose prescription. Additionally or alternatively, the inflatable retractors 330, 332 may include dual compartment balloons for the bladder and/or rectum retractors. These dual compartments can infuse a solution (e.g., Fricke Dosimeter solution or Ferrous Sulfate) for the retraction balloons. Additionally or alternatively, using these solutions, dose received to the bladder and the rectum may be measured. For example, a calculation of net ferrous to ferric conversion may be used to measure an absolute dose received by the bladder and the rectum.

With continued reference to FIG. 19, the attachment mechanisms 377, 379 may have corresponding retractor locking mechanisms 381, 383. The retractor locking mechanisms 381, 383, can include a push-to-lock mechanism. The retractor locking mechanisms 381, 383 may be coupled to corresponding retractor supports 374, 376. The retractor supports 374, 376 may include a toothed interface, such as a one-way toothed interface, with which the corresponding retractor locking mechanisms 381, 383 is coupled. For example, the first retractor locking mechanism 381 may include a corresponding toothed interface with the first retractor support 374 to prevent proximal and/or distal axial movement of the first retractor support 374. Similar functionality may apply to the second retractor locking mechanism 383 with the second retractor support 376. Other interfaces are possible.

The retractor supports 374, 376 may be coupled to corresponding retractor balloon supports 318, 319. The retractor balloon supports 318, 319 may include corresponding inflatable retractors 330, 332. The inflatable retractors 330, 332 are adapted to be releasably coupled to the ovoid assembly at first and second retractor connection portions 334, 336. The first and second inflatable retractors 330, 332 have a deflated configuration for insertion into a patient and an adjustably inflated configuration for retraction of tissue during treatment. The first inflatable retractor 330 is adapted to be positioned to retract the bladder of a patient during treatment and the second retractor second inflatable retractor 332 is adapted to be positioned to retract the rectum of a patient during treatment. The tandem 302 and the first and second inflatable ovoids 312, 314 are adapted to be coupled to a radioactive source to deliver an implant radiation dose suitable for cancer treatment at a cancerous cervical treatment site in a patient. The retractor balloons 330, 332 are coupled to catheters 384, 386 that are preferably coupled to the ovoid assembly 310. The retractor balloons 330, 332 are preferably inflated with saline. The inflatable retractors 330, 332 may include functionality of the retractors 230, 232 described herein.

Figure 20:
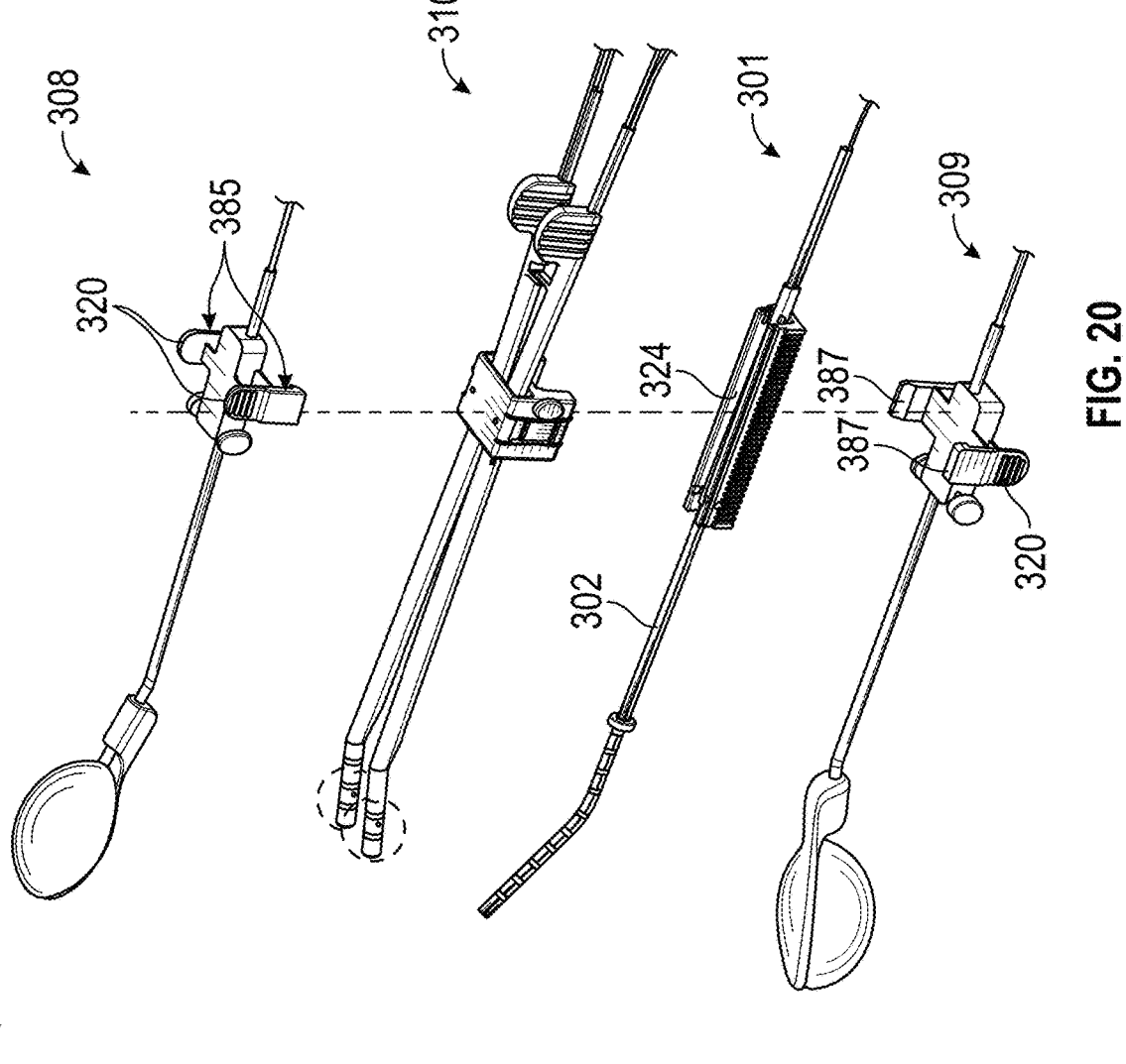
FIG. 20 shows an exploded view of an example applicator.

FIG. 20 shows an exploded view of an example applicator 300. The applicator 300 includes a tandem assembly 301, ovoid assembly 310, and retractor assemblies 308, 309. The retractor assemblies 308, 309 can be configured to be releasably coupled to the ovoid assembly 310. For example, a snap, friction, or other fit may be used. The ovoid assembly 310 may be attached to the tandem assembly 301 via the tandem connector 324. The retractor assemblies 308, 309 may include one or more grip elements 320 as shown. The grip elements 320 may be included for ease in decoupling the corresponding retractor assemblies 308, 309. Grip elements 320 can be disposed opposite attachment elements 385. The attachment elements 385 can be configured to couple to the ovoid support mechanism 316. Similarly attachment elements 387 of the second retractor assembly 309 can be included to couple to the ovoid support mechanism 316. Other configurations are possible.

Figure 21:
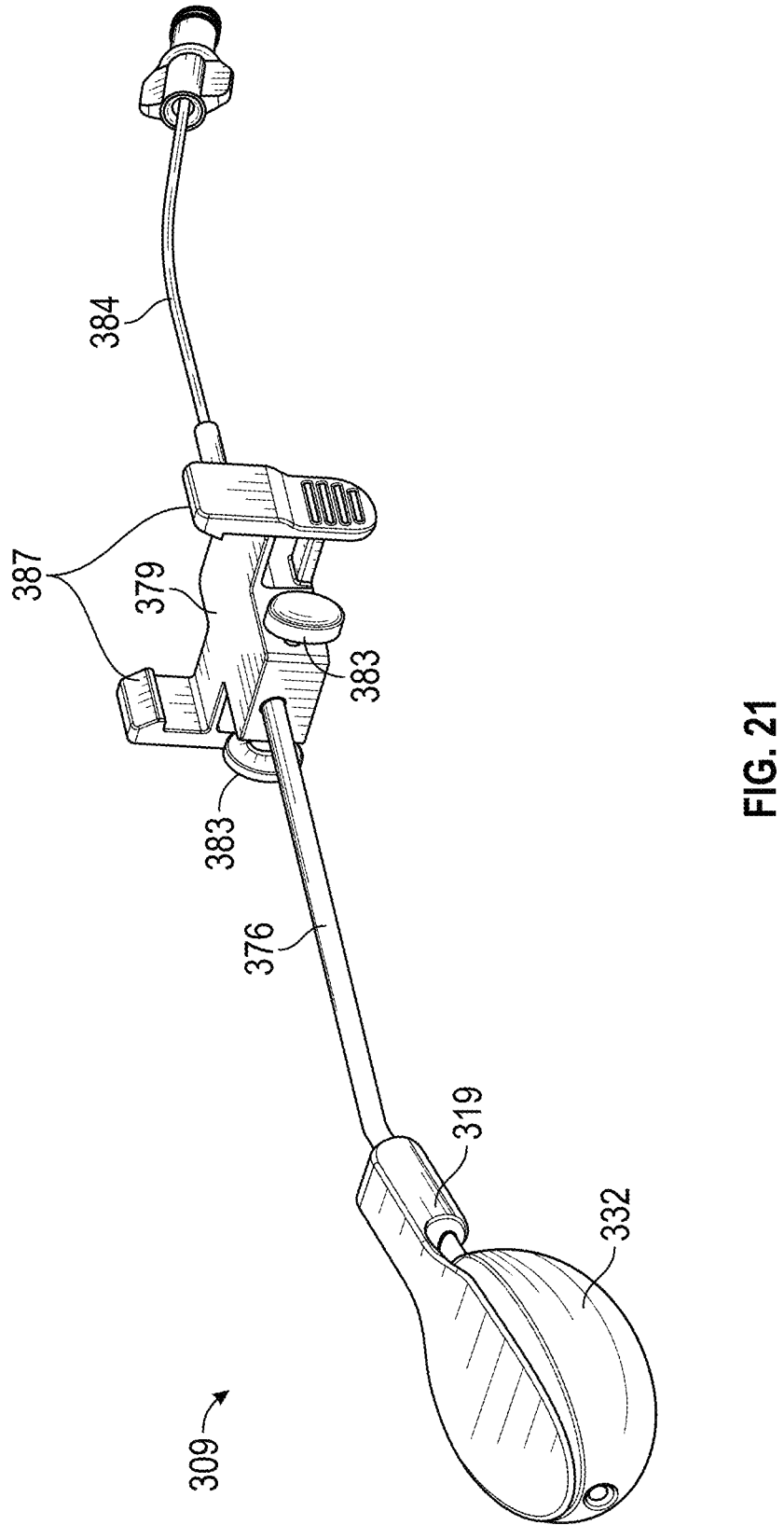
FIG. 21 shows an example second retractor assembly.

FIG. 21 shows an example second retractor assembly 309. One or more corresponding features may be included in and/or apply to the first retractor assembly 308. The second retractor assembly 309 may include a corresponding second attachment mechanism 379 configured to couple to the ovoid support mechanism 316. As noted, the second retractor locking mechanism 383 may be configured to secure a location of the second retractor assembly 309 relative to the tandem 302 and/or other elements of the applicator 300. A first catheter 384 can be included for filling the second inflatable retractor 332 with a fluid (e.g., saline, air, etc.). The first catheter 384 may pass through the second retractor support 376.

Figure 22:
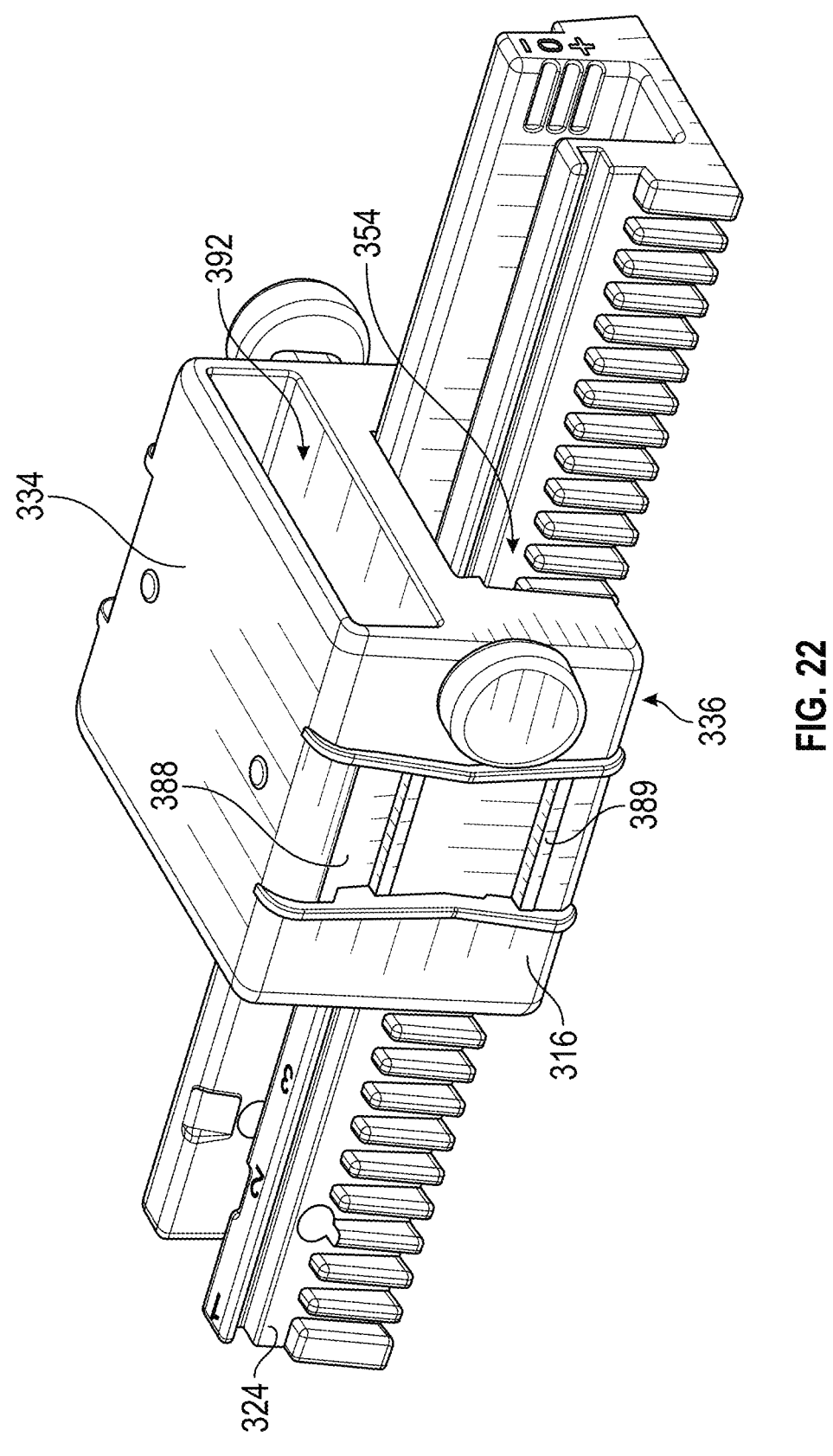
FIG. 22 shows a detail perspective view of an example ovoid support mechanism coupled to a tandem connector.

FIG. 22 shows a detail perspective view of an example ovoid support mechanism 316 coupled to a tandem connector 324. The ovoid support mechanism 316 can include a first connection portion 334 and a second connection portion 336. The first connection portion 334 can be configured for receiving a corresponding first retractor assembly 308 and the second connection portion 336 can be configured for receiving a second connection portion 336. One or both of the connection portions 334, 336 can include a substantially flat surface configured to mate with a corresponding flat surface of the retractor assemblies 308, 309. The ovoid support mechanism 316 can be coupled to the tandem connector 324 at an ovoid assembly interface 354. The ovoid assembly interface 354 can include one or more protrusions or teeth configured for mating with respective indentations or teeth of the ovoid support mechanism 316. The one or more protrusions or teeth of the ovoid assembly interface 354 may be disposed axially such that the coupling between the ovoid support mechanism 316 and the tandem connector 324 can be adjusted axially. Advantageously, a toothed ovoid assembly interface 354 can reduce slippage between the ovoid support mechanism 316 and the tandem connector 324. The ovoid support mechanism 316 may include an ovoid guide mechanism 392. The ovoid guide mechanism 392 can include a cavity for receiving the handle portions 344, 346 therethrough. Rods or pins (not labeled) may be inserted to couple the ovoid support mechanism 316 with the handle portions 344, 346 within the ovoid guide mechanism 392. The attachment elements 385, 387 (discussed above) can be configured to couple to the ovoid support mechanism 316 at corresponding attachment elements 387, 389, for example, via a snap fit.

Figure 23:
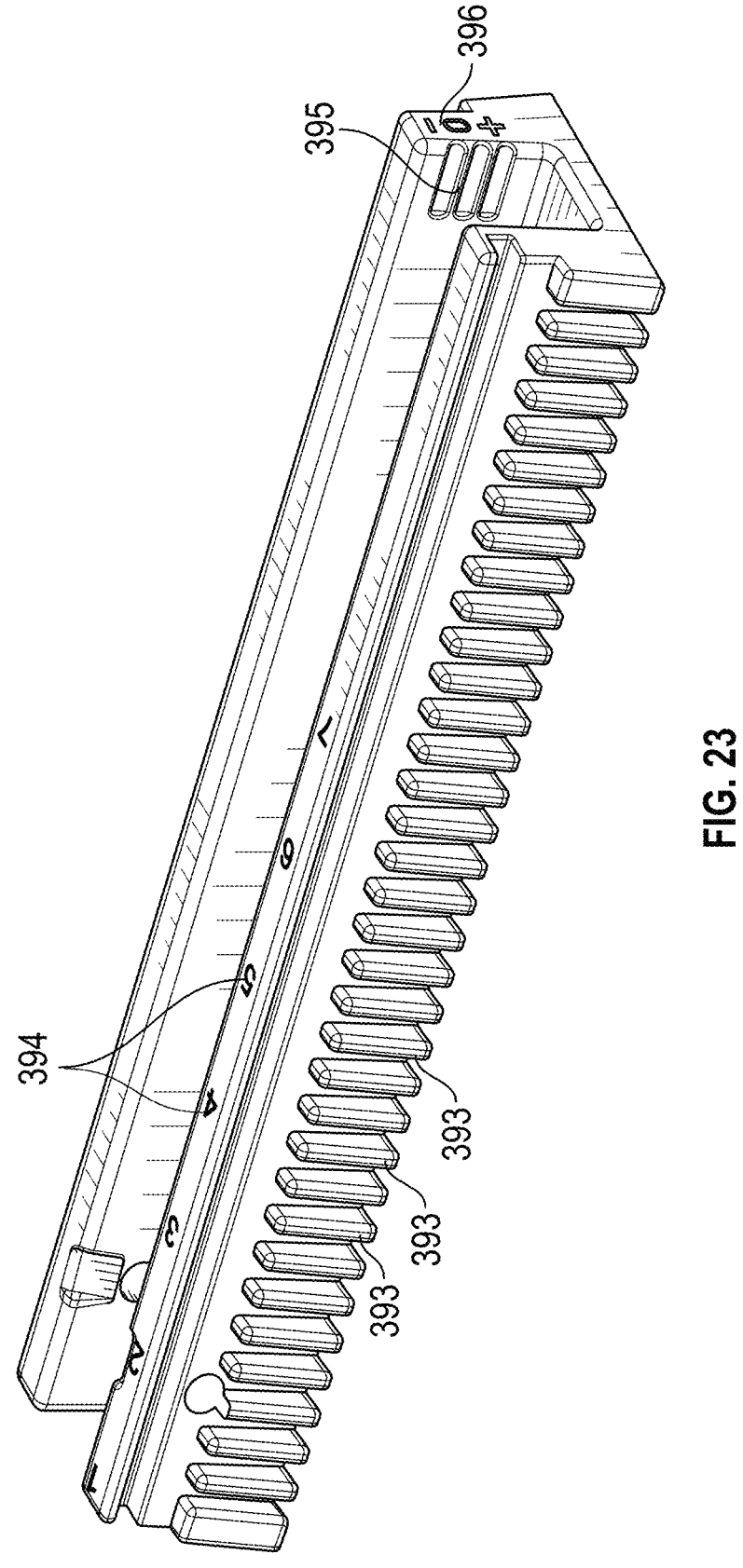
FIG. 23 shows an example tandem connector.

FIG. 23 shows an example tandem connector 324. The tandem connector 324 can include a plurality of adjustment elements 393 to allow for coupling and/or decoupling the ovoid support mechanism 316 thereto. The adjustment elements 393 may include teeth, ridges, protrusions, etc. For ease of replication of a distance or aligning the ovoid support mechanism 316 on the tandem connector 324, the tandem connector 324 may include adjustment indicators 394 corresponding to the tandem length inside the uterus (from tandem tip to the flange) showing the point the ovoid assembly to be placed, such as shown in FIG. 23. Additionally or alternatively, height adjusters 395 may be included to allow additional degrees of freedom of the tandem 302 in anterior-posterior direction. The height adjusters 395 may include recesses, teeth, or other mechanisms to reduce a likelihood of slippage. Corresponding height indicators 396 can be included to aid a user.

Figure 24:
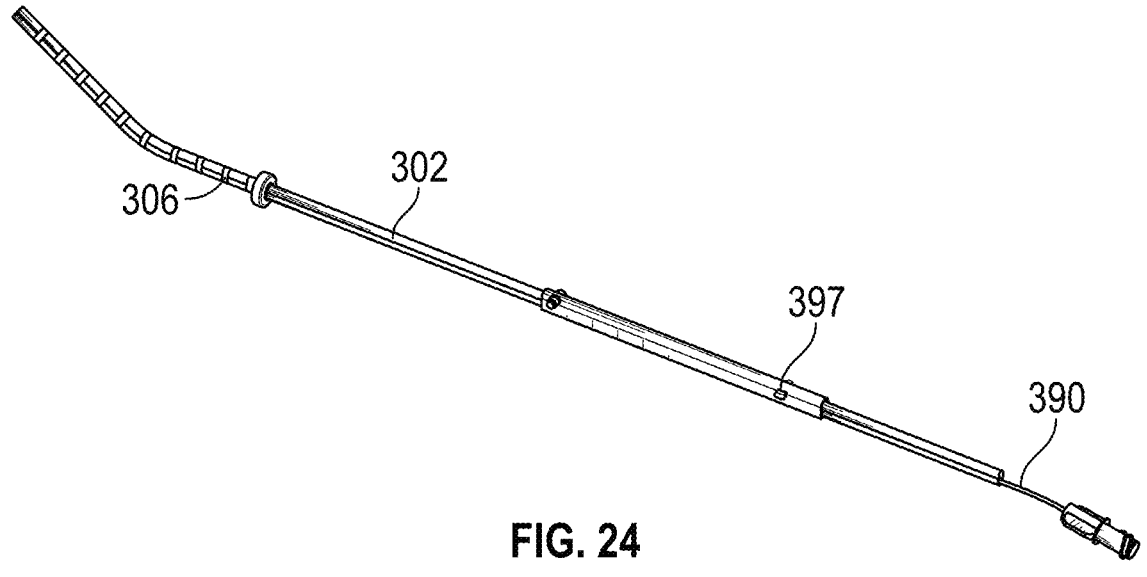
FIG. 24 shows an example tandem.

FIG. 24 shows an example tandem 302. The tandem 302 can include a tandem coupling mechanism 397 configured to couple with the height adjusters 395. The tandem coupling mechanism 397 may include one or more protrusions, for example, to couple with corresponding grooves or recesses. One or more radiographic markers 306 may be included near a proximal end of the tandem 302. The radiographic markers 306 may be spaced at regular intervals. The tandem may include a shaft that may include a fiber optic bundle 390. The fiber optic bundle 390 may be included in a lumen of a multi-lumen shaft of the tandem 302, as described herein. The fiber optic bundle 390 may be connected to a camera, such as one described herein, for imaging an interior of a patient during a procedure.

Figure 25:
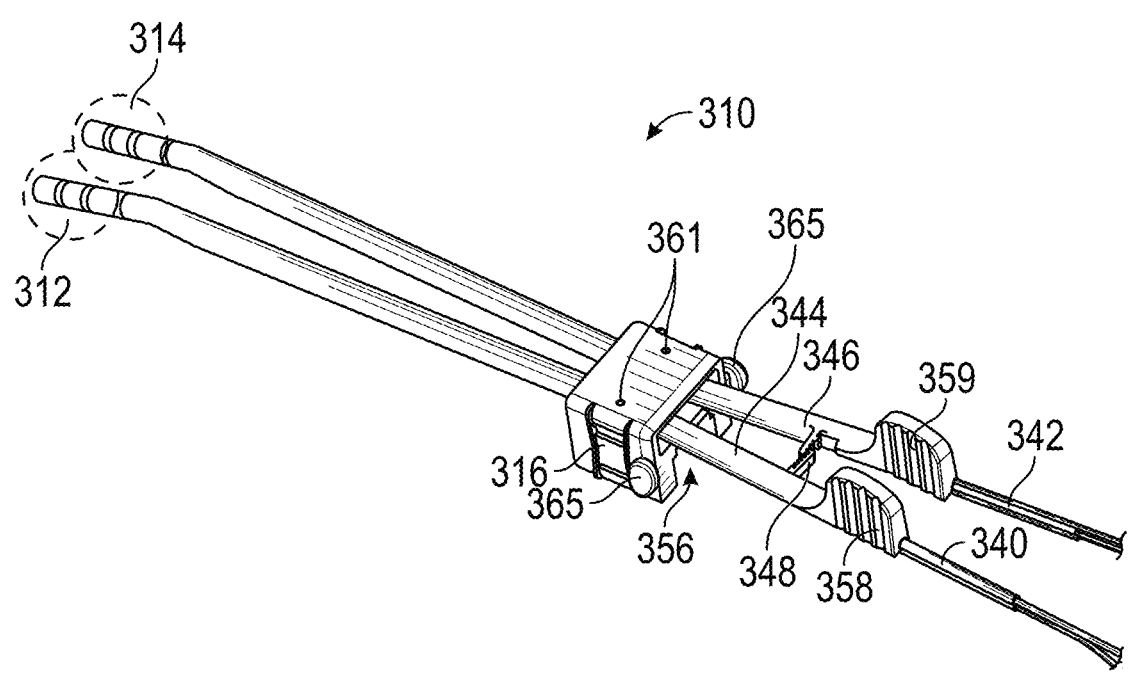
FIG. 25 shows an example ovoid assembly.

FIG. 25 shows an example ovoid assembly 310. As shown, connector elements 361, such as rods or pins, may couple the handle portions 344, 346 to the ovoid support mechanism 316. The connector elements 361 may promote pivotal or angular motion of the handle portions 344, 346 while reducing axial movement of the handle portions 344, 346. Ovoids 312, 314 may include radiographic markers. The ovoids 312, 314 may be disposed at a proximal end of the handle portions 344, 346. As adjustment mechanisms 358, 359 are utilized, an adjustment interface 348 (e.g., a unidirectional interface) may adjustably secure a relative position (e.g., angular position) of the ovoids 312, 314 relative to one another. A single- or multi-lumen shaft may be used for one or both of the catheter shafts 340, 342. Fluid may be passed therethrough and/or optical fiber (e.g., for use with an imaging device) may be inserted therein. The ovoid support mechanism 316 can allow for the tandem 302 through a tandem assembly receiver 356. When coupled with the tandem connector 324, the tandem assembly receiver 356 can form a cavity through which the tandem 302 can be disposed.

Figure 26:
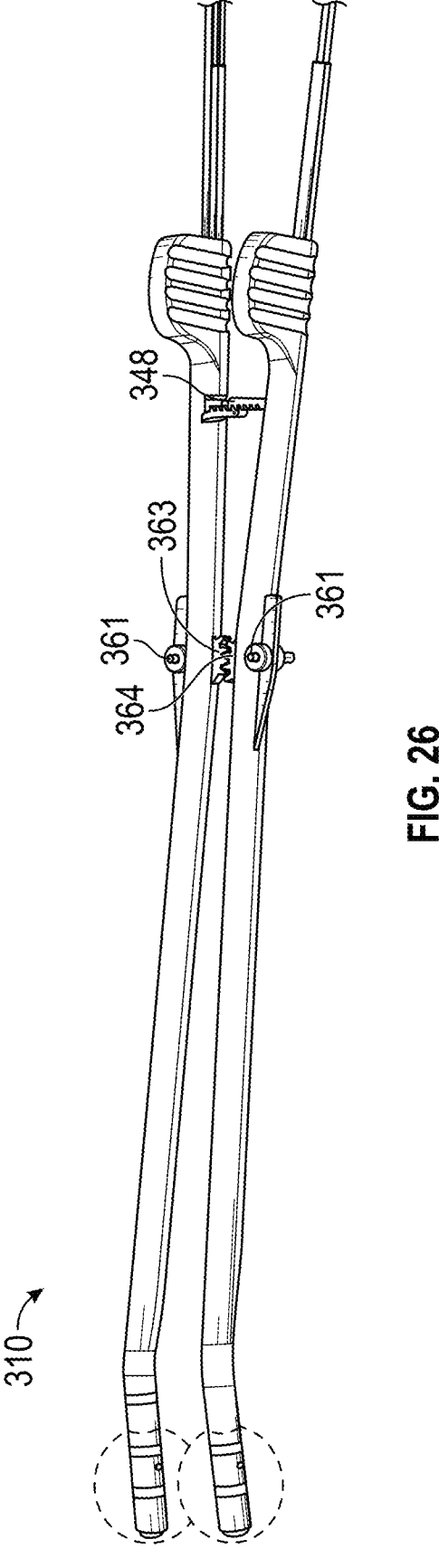
FIG. 26 shows an example ovoid assembly without an ovoid support mechanism.

FIG. 26 shows an example ovoid assembly 310 without an ovoid support mechanism 316. Ovoid rotation interfaces 363, 364 can be included on corresponding handle portions 344, 346. The ovoid rotation interfaces 363, 364 can include a toothed or geared interface with each other. Each of the handle portions 344, 346 can rotate about corresponding connector elements 361.

Additional Shielding Considerations in IMRT

The HDR brachytherapy dosimetry systems described herein may have two degrees of freedom, such as source dwell position and dwell time to work with to make the dose distribution conformal to the lesions being treated. Intensity modulation of the HDR dose distribution can include using a moving shielded wire in tandem with the Ir-192 source to add a third degree of freedom to lower the dose in the direction of the OARs completely or partially. Shielding the dose can improve or optimize the dose based on the dose tolerances recommended by American Brachytherapy Society (ABS), and protect the organs-at-risk, and limit short and/or long term injuries to these structures such as proctitis, fistulas, etc.

A multi-lumen tandem and inflatable ovoid system can enable the use of the IMBT advantageously to send the radioactive (e.g., Ir-192) source to a central channel of the tandem or ovoids, and send a gold or tungsten tipped wire to the lumen facing the organ at risk, such as the rectum or sigmoid colon. Therefore, the dwell time, the dwell position, and the shielding position are the three degrees of freedom to use advantageously for dose shaping and conformal treatment planning to maximize the high dose intensity in the tumors and minimizing it for the OARs. Various minimally invasive multi-lumen catheters can be included to use in the proposed IMBT technique. Vaginal packing may be avoided, for example, in patients undergoing the T&O procedure utilizing this technique if the dose is adequately lowered to the OARs.

The multi lumen design for the ovoids can be used to selectively and differentially deliver dose to areas closest to the lesion and minimize dose to the OAR. Advance cervical cancer that does not significantly respond to external beam radiation therapy and/or chemotherapy may need an interstitial implant using multiple invasive needles. This may be avoided using multi lumen ovoids by selectively loading the catheters closest to the unresponsive tumor in the cervix and vaginal wall and delivering high doses while sparing the bladder and rectum using the balloon retractors. FIGS. 27-29C show examples of multi lumen ovoids. One lumen can be used for the water infusion to inflate the ovoid balloon, the others for radiation delivery in the central channel and/or one or more channels used for delivery of the radiation. Additional channels (e.g., posterior channels) can be used for shielding wire to dwell in synchronously with the source wire to make the dose distribution conformal and spare the organs at risk.

An inverse planning algorithm optimization can be defined to apply the degrees of freedom outlined herein to maximize tumor dose coverage and minimize OARs dose. The inverse planning algorithm improves or optimizes the dose by simulated annealing optimization using the tumor and the OARs objective functions defined by the dosimetrists physicist for the target and the OARs by maximizing dose intensity distribution and conformity of the target and minimizing the dose to OARs. The parameters in the optimization included the source dwell position, dwell time, and the position and fractional transmission of radiation through the shielding material. As the source and the shielding wires are moving synchronously, the optimization program can make the shielding sequences at which the shielding wires dwell with the source, and/or automatically retract the shielding wires when not needed.

An afterloader capable of delivering IMBT can be used by utilizing 3 degrees of freedom treatment planning and redesign of the afterloader to add an extra dummy wire with, for example, a 0.5 cm to 2 cm tip made out of a minimum 1 mm diameter, e.g., gold rod or a square shaped rod to block the radiation in the direction of the gold block. Other high atomic number and density metals such as the one outlined in Table 1 can be used for this purpose. The afterloader will have an extra indexer for the blocking wire. The original indexer is used for the active and dummy wire traveling to different channel as per treatment plan at a programmed dwell position and dwell time. The proposed extra drive and indexer moves the gold block wire to the channel behind the active wire at the same dwell time and position planned by the treatment planning computer. The first indexer sends the first dummy wire to all the channels used for treatment to make sure the transfer guide tubes as well as the applicator channels are open and not blocked. The same step may be done with the second indexer traveling to the channels that are supposed to block the radiation to make sure these channels are open as well. After this step, the active wire and the gold wire simultaneously travel to their planned channels and deliver the dose.

Figure 27:
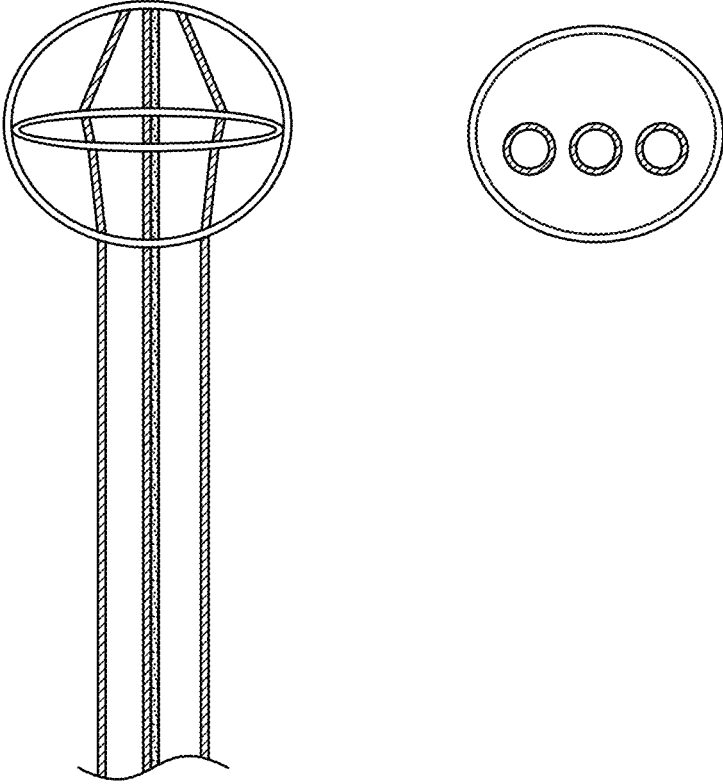
FIG. 27 shows an example of multi-channel radiation delivery system (4 channels are shown).

FIG. 27 shows an example of multi-channel radiation delivery system (4 channels are shown). The delivery system can deliver differential doses to different ovoids to improve the therapeutic ratio. As shown, one of the central lumens (shown in blue) can be used to infuse water to inflate the ovoid balloon. The other central lumen and/or the two peripheral lumens (shown in red) can be used selectively to deliver radiation doses.

As shown, a three lumen extrusion for the tandem can be used: one for the CMOS camera with fiberoptic bundles carrying light, laser light, or a fiberscope, second channel for an ultrasound transducer, and the third as utility channel to deliver radiation source, i.e. Ir-192, Cs-137, Co-60, etc. Alternatively, a dual lumen tandem can be used, with one lumen for dose delivery, and the second to be used as a utility channel for either optical imaging or ultrasound imaging or insertion of the shielding wire for IMBT to lower the dose to the sigmoid colon and keep the tandem diameter to a minimum. Additional variations are possible, such as those described herein.

Figure 28A:
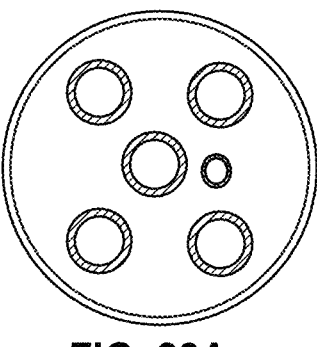
FIG. 28A-C show an example of a 6- or 5-lumen ovoid, according to some embodiments.
Figure 28B:
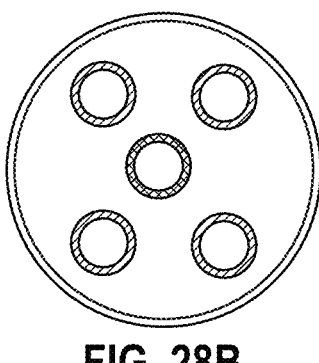
Figure 28C:
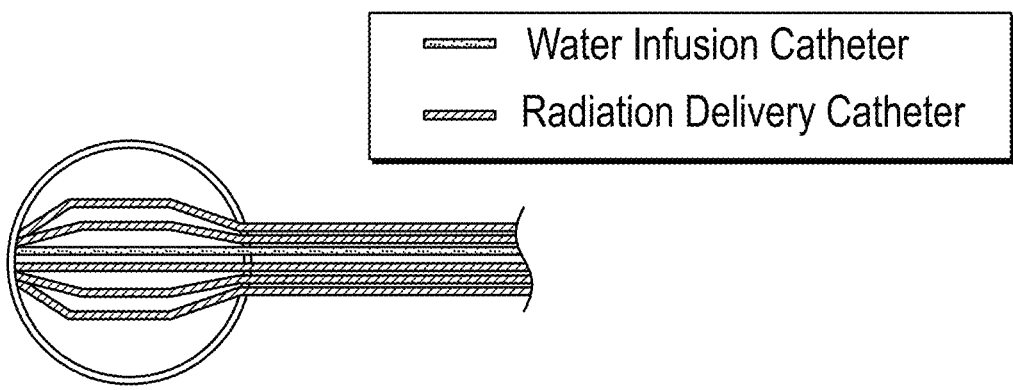

FIGS. 28A-C show an example of a 6- or 5-lumen ovoid, according to some embodiments. The smaller lumen (shown in blue) can be used to infuse water/saline to inflate the balloon. The other lumens (shown in red) may be selectively programmed to deliver radiation doses to the areas closest to the regions with cancer.

Figure 29A:
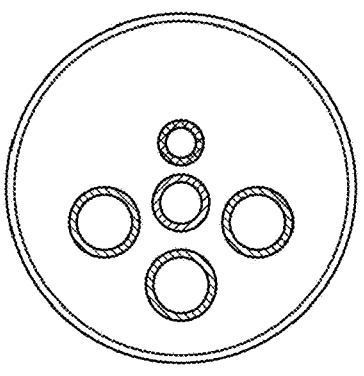
FIG. 29A-B show examples of a multi-lumen ovoid with 5 channels or 10 channels, respectively.
Figure 29B:

FIGS. 29A-B show examples of a multi-lumen ovoid with 5 channels or 7 channels, respectively. In FIG. 29A, a light blue color is used to show a lumen that can infuse water. The channels depicted in red can deliver radiation. The 3 channels shown in green can be used for shielding the radioactive source. The green channels can include a corresponding gold- or tungsten-tipped wire. These tipped wires can be operated and/or moved to be substantially synchronous with the movements of the active source in order to generate an intensity modulated brachytherapy IMBT plan that can better protect the organs situated posteriorly and/or laterally to the source.

FIG. 29B shows an example of a 7-lumen vaginal cylinder cross section to treat post-surgical endometrial and vaginal cancers with HDR brachytherapy. The lumens are shown in red. The 3 catheters (shown in green) are designed for gold or tungsten shielding catheters. As with the wires of FIG. 29A, these catheters can be operated in synchrony with the active wire to protect the OARs in the left or right lateral directions or posteriorly or using all 3 catheters with an afterloader with three gold or tungsten shielding wires.

As shown in FIG. 29B, sets of multi lumen cylinders can take advantage of the proposed feature to protect the bladder or the rectum when treating the primary vaginal cancer using the vaginal cylinder or for prophylactic treatment of the vaginal cuff region for post-surgical endometrial carcinomas. The central channel with the HDR sources dwelling surrounded by three lumens designed for the shielded wire or wires can dwell synchronously and in steps sequenced by the treatment planning IMBT optimizer can deliver a conformal dose with sparing the OARs.

Figure 30:
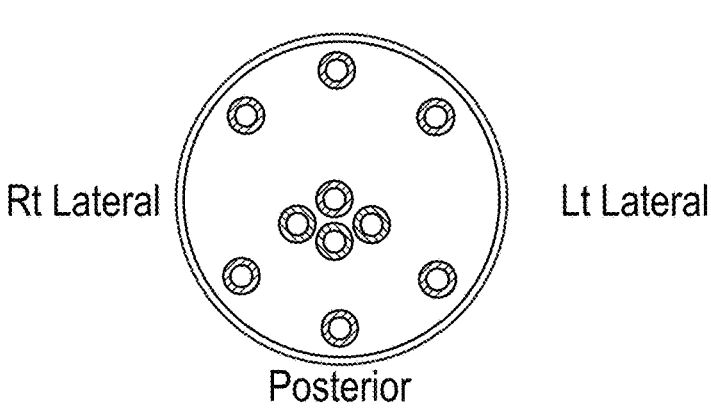
FIG. 30 shows different positions of the radioactive wire with Ir-192 source (shown in red) and the shield wire(s) (shown in green).

FIG. 30 shows different positions of the radioactive wire with Ir-192 source (shown in red above a corresponding shield wire) and the shield wire(s) (shown in green below a corresponding source). As shown, the radioactive wire is moved along at the same rate as the shield wires. Thus, the dwell time for each is the same. Additionally or alternatively, the dwell positions and dwell times for each step for both wires may be the same. One or both wires may retract with a step size of about 5 mm. This procedure can be accomplished by using multiple lumen catheters designed to protect the organs at risk, such as those described herein.

Figure 31:
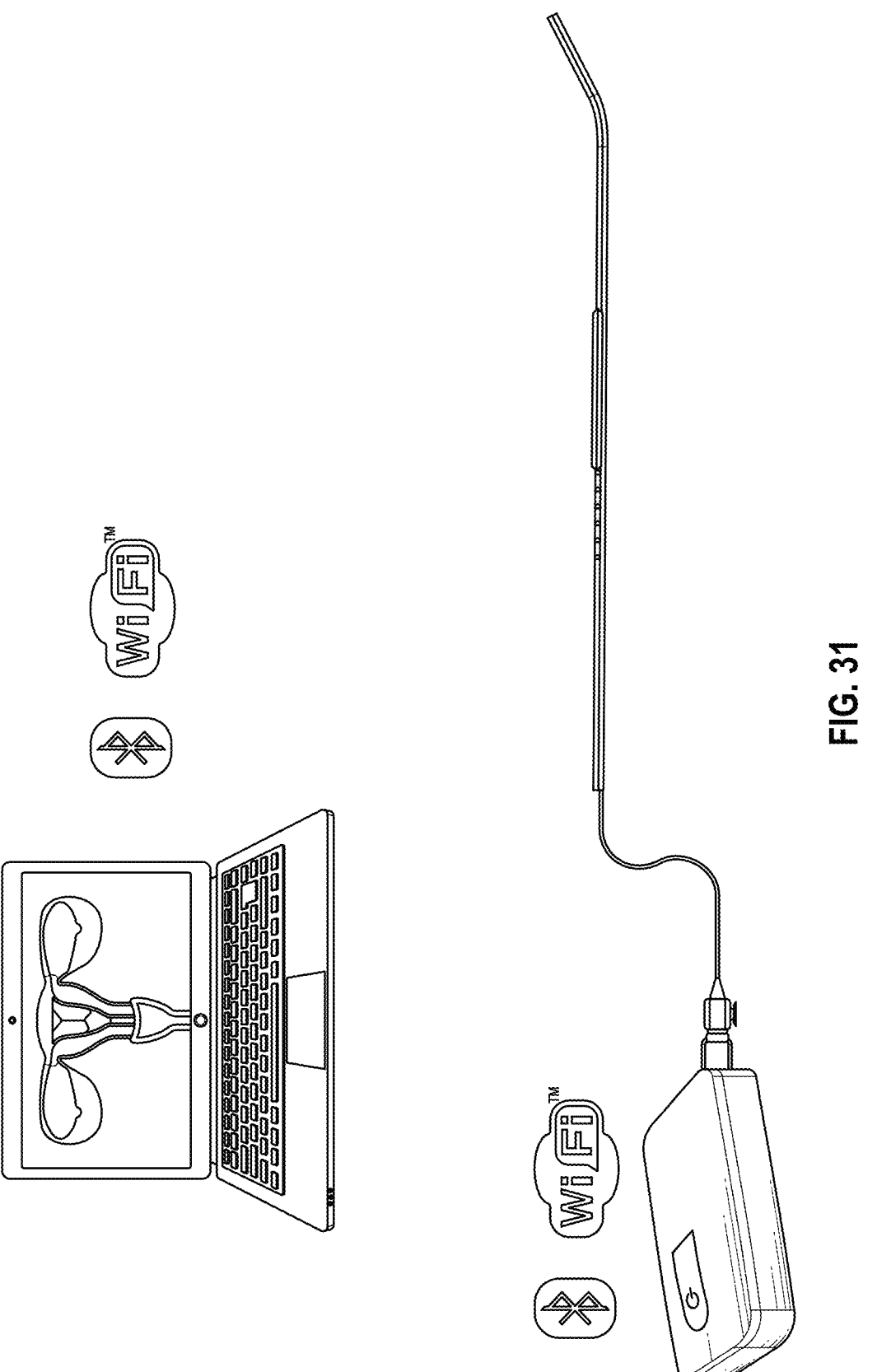
FIG. 31 shows a schematic view of a wireless CMOS camera system connected to a Bluetooth/WIFI and camera Light Emitting Diodes (LED) driver.

FIG. 31 shows a schematic view of a wireless CMOS camera system connected to a Bluetooth/WIFI and camera Light Emitting Diodes (LED) driver with an IP address for streaming, making the images/videos to be captured using an image processing software in the Laptop/iPad/iPhone, or desktop computers paired with the Bluetooth/WIFI. The images can be displayed so the physician can guide the tandem or any other catheter wirelessly. It is convenient for the physician to not be limited by the cables hardwired connections as well as saving the video or static images on the different computer/telephone/tablet/ipad platforms. The CMOS camera may be replaced with a miniaturized transducer to perform ultrasound imaging and wirelessly transfer the images to a computer/laptop/tablet/iphone system via Bluetooth/WIFI streaming system.

Figure 11:
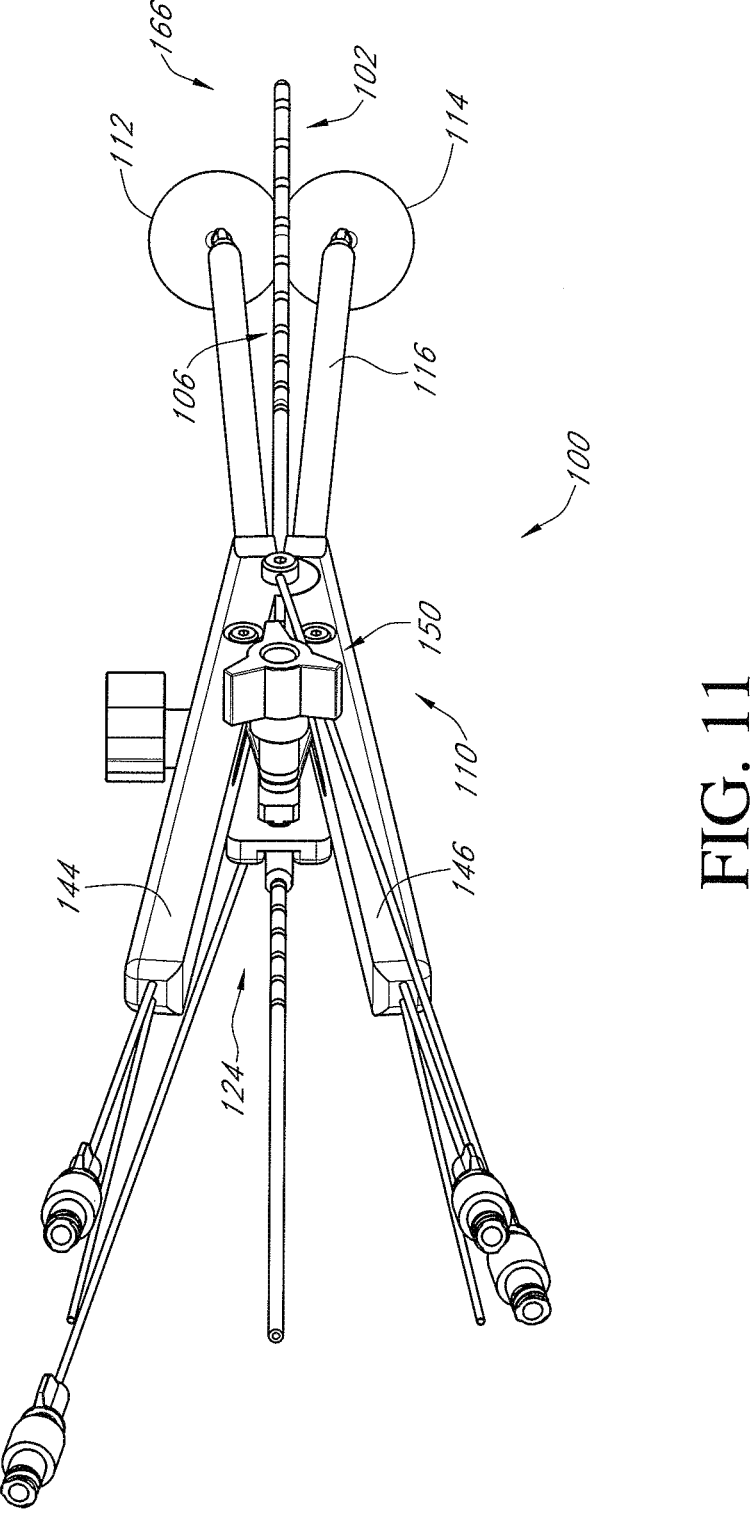
FIG. 11 illustrates a top rear view of the applicator system of FIG. 7 according to embodiments of the present application.
Figure 12:
FIG. 12 illustrates a top front view of the applicator system of FIG. 7 according to embodiments of the present application.

A CMOS camera lit with diodes or multiple fiber optics can carry light to the tip of the camera, that is connected to a Bluetooth/WIFI module streaming the video images on a closed circuit that can be detected by any computer, laptop, iPad, iPhone or other cellular telephone paired with the Bluetooth to record the images and show and display the images so the physician can guide the tandem or any other catheter wirelessly (FIG. 11). This is extremely convenient for the physician to not be limited by the cables hardwired connections as well as saving the video or static images on the different computer/telephone/tablet/ipad platforms. The images can further be analyzed, i.e. for sounding the uterus, visualization of abnormal tumor growth, diagnosing a tumor and its pathology or histology by using diffuse optical spectroscopy for example (2-3).

The CMOS camera may be replaced with a miniaturized transducer to perform ultrasound imaging or diffuse optical spectroscopy as proposed above and wirelessly transfer the images to a computer/laptop/tablet/iphone system via Bluetooth/WIFI streaming system.

Figure 32:
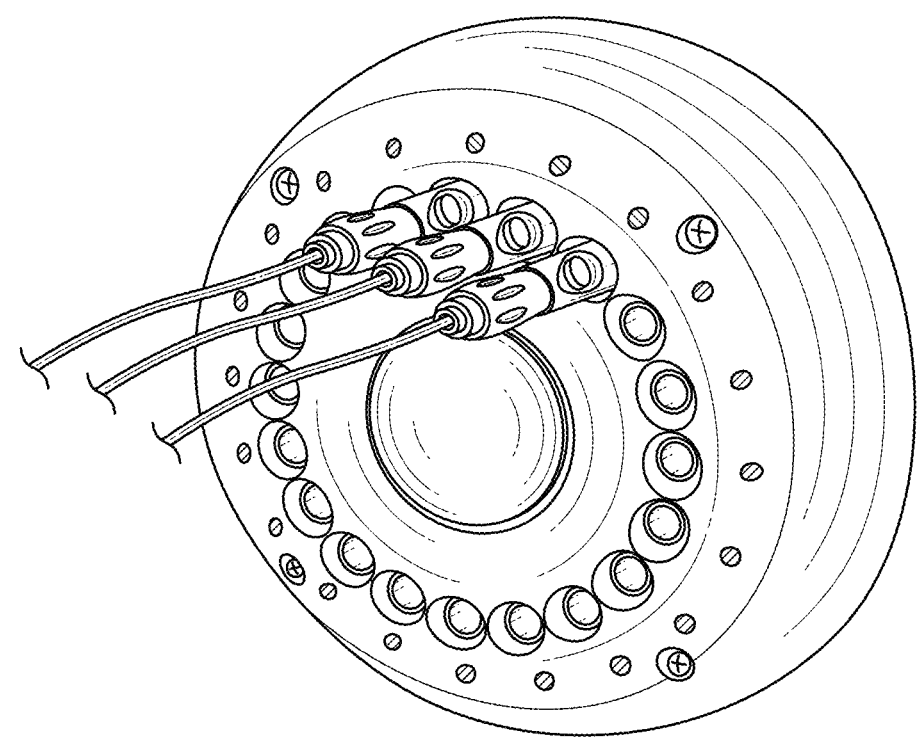
FIG. 32 shows an example 20-channel turret in which the radioactive Ir-192 delivery delivers the radiation dose.

FIG. 32 shows an example 20-channel turret (e.g., from Varian Medical) in which the radioactive Ir-192 delivers the radiation dose. One, two, or more channels such as Channels 18-20 can be programmed to send the Gold or Tungsten shielding catheters one at a time or all simultaneously in synchrony with the active wire to modulate the intensity of the radiation as the source is dwelling in the central catheter. The afterloader may include the dummy wires with gold or tungsten tips descried herein to dwell at the same time as the Ir-192 wire with the same dwell times to spare the organs-at risk from the radiation.

Figure 33:
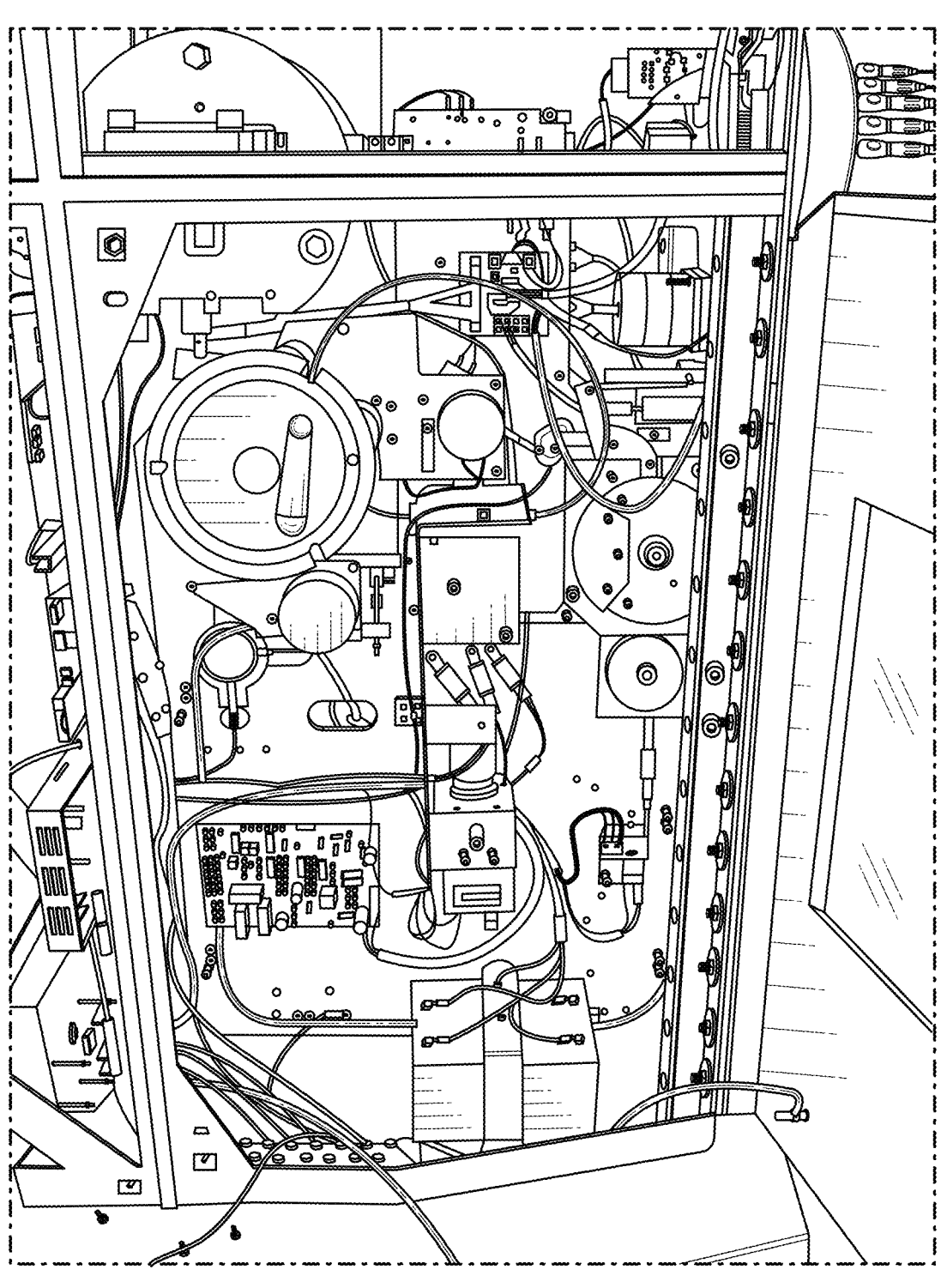
FIG. 33 shows the afterloader with one active wire drive and a dummy wire check drive with the 20-channel turret such as the one shown in FIG. 32.
Figure 34:
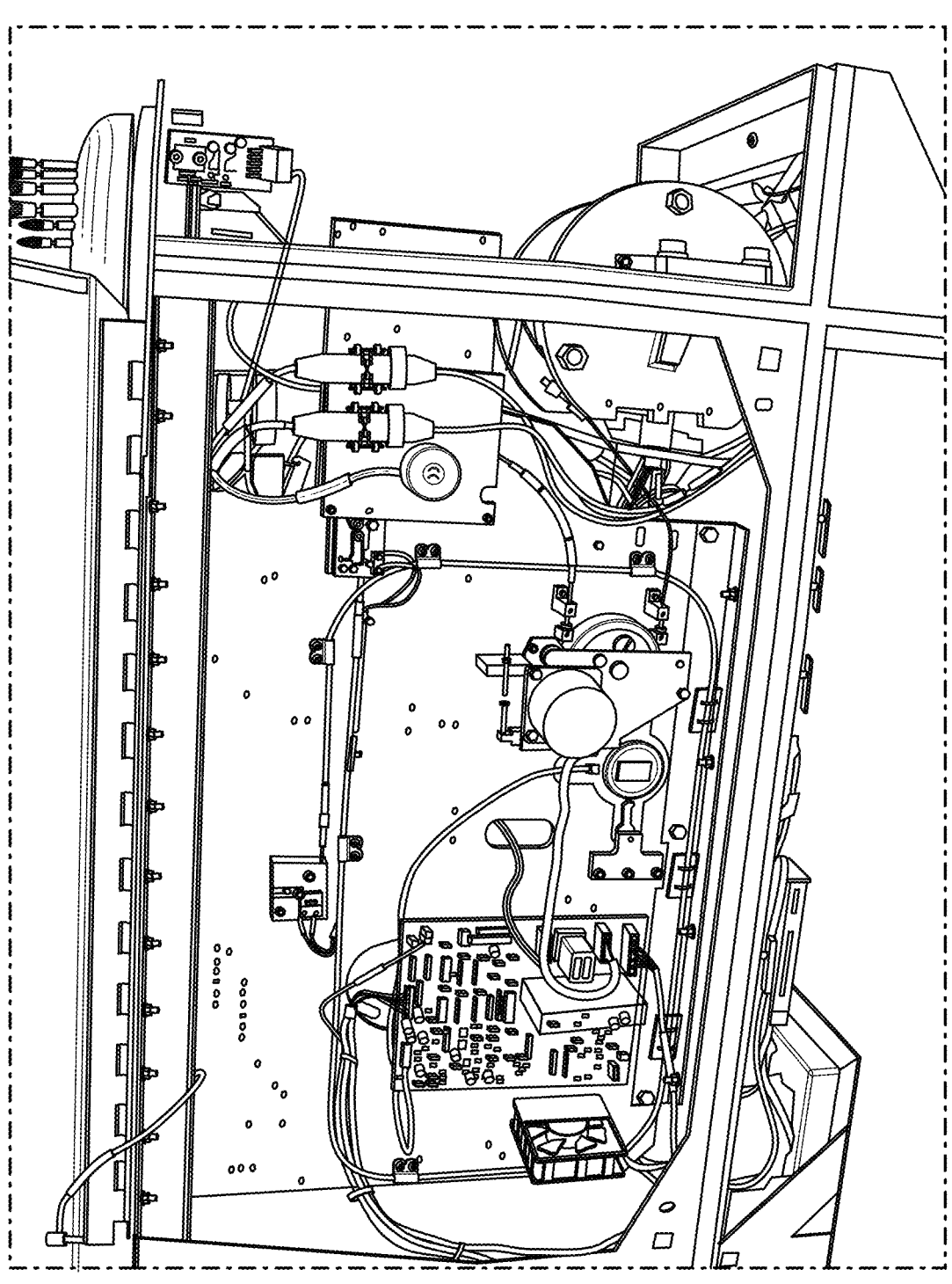
FIG. 34 shows the afterloader with one active wire drive and a dummy wire check drive with the 20-channel turret such as the one shown in FIG. 32.
Figure 35:
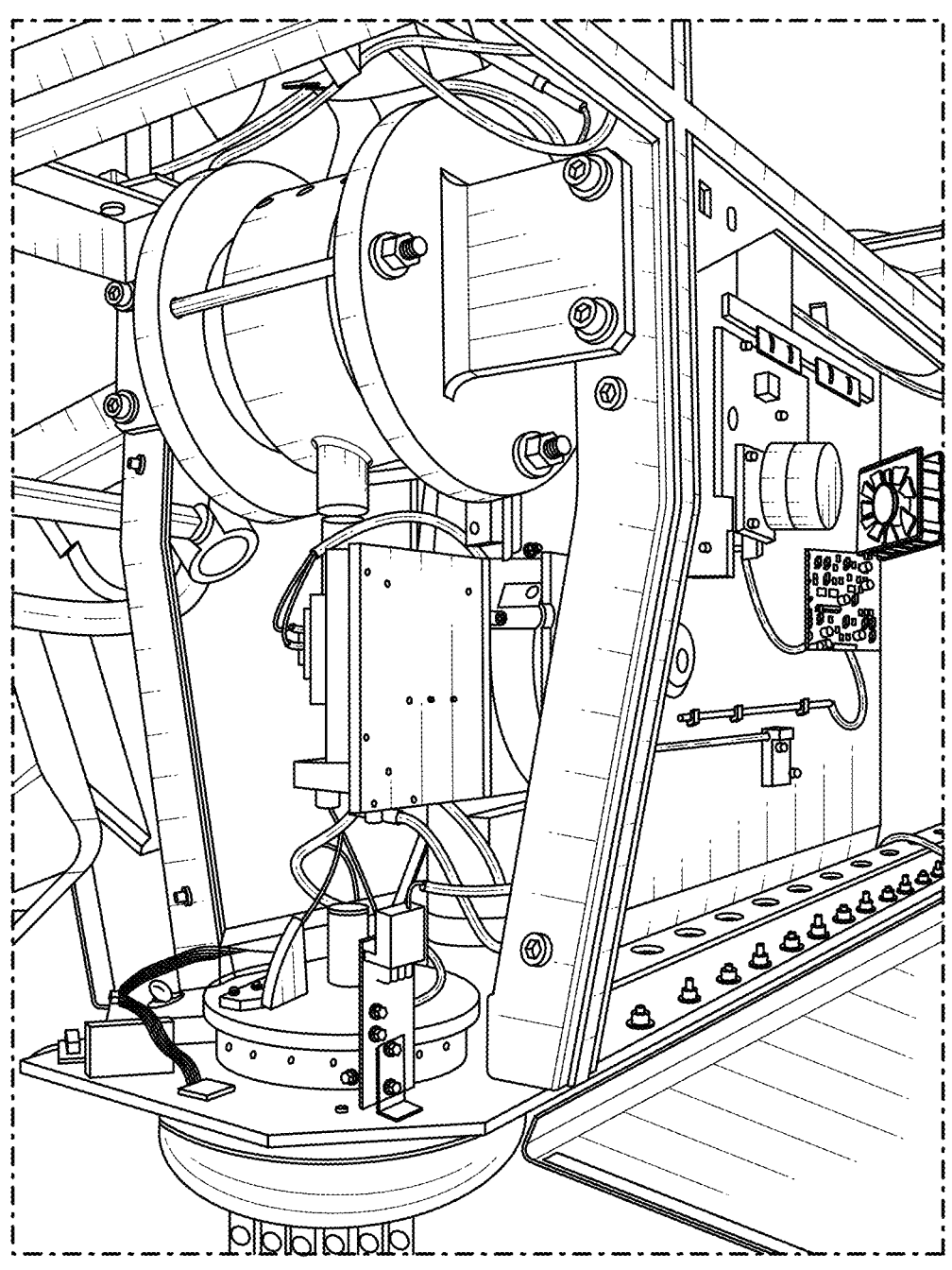
FIG. 35 shows how three of the 20 channels can be allocated to shielding wires with gold or tungsten tips.

FIGS. 33-35 show an alternative to the manual insertion of the gold or tungsten rod using a modified afterloader. Different perspectives of an internal circuitry of a Varian Medical System's Ir-192 afterloader are shown. The afterloader can modulate the dummy wire(s) with a tip made out of gold, or tungsten or other high atomic dense metals to partially and preferentially modulate the dose received by certain areas of the target organ and spare the organs at risk. A third or fourth dummy wires with gold or tungsten or other high atomic number and high density metal wires for intensity modulation in addition to the active and dummy check wires. The insertion can be done automatically by adding a 0.5 cm or 1 cm (range 0.5 cm-2 cm) long with a diameter of 1.2 to 3 mm gold or tungsten rod laser welded to the tip of a dummy stainless steel or Nitinol wire. This shielding wire or wires can be programmed to leave the afterloader and dwell into the lumen or lumens immediately facing the organ at risk behind or next to the lumen the active wire is traversing. The treatment planning system can be programmed to move the active and tungsten wire simultaneously to partially shield the 360-degrees radiation emission in the direction of the OARs. The amount of shielding depends on the diameter of the gold or tungsten rods behind the source.

FIGS. 33-34 show the afterloader with one active wire drive and a dummy wire check drive with the 20-channel turret such as the one shown in FIG. 32. The active drive is painted in black and red color. FIG. 35 shows how three of the 20 channels can be allocated to shielding wires with gold or tungsten tips to dwell in the lumens surrounding the central channel to shape the dose and protect the OARs.

It will be apparent to those skilled in the art that various modifications and variations can be made in the present embodiments and methods without departing from the scope or spirit of the advantages of the present application. Thus, it is intended that the present application cover the modifications and variations of these embodiments and their equivalents.

What is claimed is:

1. A system for treating cervical and/or uterine cancers in intensity modulated brachytherapy with an intracavitary brachytherapy applicator, comprising:

a tandem assembly comprising a tandem and a tandem connector, the tandem configured for insertion into a cervix of a patient and the tandem connector configured to receive the tandem within an interior of the tandem connector along a longitudinal axis, the tandem connector comprising one or more grooves arranged along the longitudinal axis, the tandem comprising a multi-lumen shaft configured to receive one or more wires therethrough, each of the one or more wires comprising a metal having an atomic number greater than 70;

an ovoid assembly comprising first and second adjustably inflatable ovoids and an ovoid support mechanism, the ovoid assembly comprising first and second handles configured to support the respective first and second inflatable ovoids, wherein the handles are configured to allow for user manipulation to control the relative position of the ovoids using a unidirectional adjustment mechanism, each of the handles comprising a multi-lumen shaft, the handles configured to allow for user manipulation to control the relative position of the ovoids for insertion of the ovoids within the fornices of the patient, the first and second adjustably inflatable ovoids having a deflated configuration for insertion into the patient and one or more adjustably inflated configurations for positioning the ovoid assembly during treatment, the ovoid support mechanism configured to establish a longitudinal position of the ovoid assembly relative to the tandem based on a coupling of the ovoid support mechanism with the one or more grooves of the tandem connector; and a first inflatable retractor configured to be releasably coupled to the ovoid assembly, the first inflatable retractor having a deflated configuration for insertion into the patient and an adjustably inflated configuration for retraction of tissue during treatment;

wherein the tandem and the first and second inflatable ovoids are configured to be coupled to a radioactive source to deliver an implant radiation dose suitable for cancer treatment at a cancerous cervical and/or uterus treatment site in the patient; and wherein a first lumen of the multi-lumen shaft of the tandem is configured to receive a first radiation source positioned within the first lumen during treatment, and wherein a second lumen of the multi-lumen shaft of the tandem is configured to receive a first wire of the one or more wires comprising a metal having an atomic number greater than 70 positioned within the second lumen during treatment with substantially synchronous movement relative to the first radiation source to provide radiation shielding in a direction of tissue not intended for radiation treatment.

2. The system of claim 1, wherein the metal comprises at least one of gold or tungsten.

3. The system of claim 1, further comprising an optical fiber, wherein the optical fiber is configured for coupling to a camera to facilitate positioning of the tandem.

4. The system of claim 1, wherein the multi-lumen shaft of the tandem comprises at least three lumens.

5. The system of claim 1, wherein the multi-lumen shaft of the tandem is configured to link an optical fiber therethrough.

6. A system for treating cervical and/or uterine cancers, the system comprising:

a tandem assembly comprising a tandem and a tandem connector, the tandem configured for insertion into a cervix of a patient and the tandem connector configured to receive the tandem within an interior of the tandem connector along a longitudinal axis;

an ovoid assembly comprising first and second adjustably inflatable ovoids and an ovoid support mechanism, wherein the ovoid assembly comprises first and second handles configured to support the respective first and second inflatable ovoids, wherein the handles are configured to allow for user manipulation to control the relative position of the ovoids, wherein the handles are configured to allow for user manipulation to control the relative position of the ovoids for insertion of the ovoids within the fornices of the patient, the first and second adjustably inflatable ovoids having a deflated configuration for insertion into the patient and one or more adjustably inflated configurations for positioning the ovoid assembly during treatment;

first and second adjustably inflatable retractors configured to be releasably coupled to the ovoid assembly, the first and second inflatable retractors having a deflated configuration for insertion into the patient and an adjustably inflated configuration for retraction of tissue during treatment; and at least one wire comprising a metal having an atomic number of greater than 70, the wire configured to reduce an amount of radiation passing therethrough;

wherein the ovoid support mechanism is configured to establish a position of the ovoid assembly relative to the tandem based on a coupling of the ovoid support mechanism with the tandem assembly, wherein the tandem and the first and second inflatable ovoids are configured to be coupled to a radioactive source to deliver an implant radiation dose suitable for cancer treatment at a cancerous cervical and/or uterus treatment site in the patient, wherein at least one of the tandem and the first and second inflatable ovoids is configured as a multi-lumen component; and wherein each multi-lumen component has a radiation lumen configured to receive a radiation source positioned therein during treatment, and wherein each multi-lumen component also has a shielding lumen configured to receive a wire of the at least one wire comprising a metal having an atomic number of greater than 70 positioned therein during treatment with substantially synchronous movement relative to the radiation source to provide radiation shielding in a direction of tissue not intended for radiation treatment.

7. The system of claim 6, wherein, the tandem comprises a multi-lumen shaft with at least three lumens configured to deliver shielded radiation therapy therethrough.

8. The system of claim 7, further comprising an optical fiber, wherein the optical fiber is configured for coupling to a camera to facilitate positioning of the tandem.

9. The system of claim 7, wherein the multi-lumen shaft of the tandem comprises at least three lumens.

10. The system of claim 7, wherein the ovoid assembly comprises a unidirectional adjustment mechanism configured to allow modification of an angular position of the first and second inflatable ovoids relative to the tandem assembly.

11. The system of claim 6, wherein each of the handles comprises a multi-lumen shaft with at least three lumens, respectively, configured to deliver shielded radiation therapy therethrough.

12. A method for providing intensity-modulated thermoradiotherapy, the method comprising:

providing a system comprising:

a tandem assembly comprising a tandem and a tandem connector, the tandem configured for insertion into a cervix of a patient and the tandem connector configured to receive the tandem within an interior of the tandem connector along a longitudinal axis;

an ovoid assembly comprising first and second adjustably inflatable ovoids and an ovoid support mechanism, wherein the ovoid assembly comprises first and second handles configured to support the respective first and second inflatable ovoids, wherein the handles are configured to allow for user manipulation to control a relative position of the ovoids, wherein the handles are configured to allow for user manipulation to control the relative position of the ovoids for insertion of the ovoids within the fornices of the patient, the first and second adjustably inflatable ovoids having a deflated configuration for insertion into the patient and one or more adjustably inflated configurations for positioning the ovoid assembly during treatment;

first and second adjustably inflatable retractors configured to be releasably coupled to the ovoid assembly, the first and second inflatable retractors having a deflated configuration for insertion into the patient and an adjustably inflated configuration for retraction of tissue during the treatment; and at least one wire comprising a metal having an atomic number of greater than 70, the wire configured to reduce an amount of radiation passing therethrough;

wherein the ovoid support mechanism is configured to establish a position of the ovoid assembly relative to the tandem based on a coupling of the ovoid support mechanism with the tandem assembly, wherein the tandem and the first and second inflatable ovoids are configured to be coupled to a radioactive source to deliver an implant radiation dose suitable for cancer treatment at a cancerous cervical and/or uterus treatment site in the patient, wherein at least one of the tandem and the first and second inflatable ovoids is configured as a multi-lumen component; and wherein each multi-lumen component has a radiation lumen configured to receive a radiation source positioned therein during the treatment, and wherein each multi-lumen component also has a shielding lumen configured to receive a wire of the at least one wire comprising the metal having an atomic number of greater than 70 positioned therein during the treatment with substantially synchronous movement relative to the radiation source to provide radiation shielding in a direction of tissue not intended for radiation treatment;

inserting the tandem into the cervix of a patient inflating the ovoid assembly comprising the first and second adjustably inflatable ovoids with fluid;

manipulating the handles of the ovoid assembly to control the relative position of the ovoids within the fornices of the patient;

inflating the first and second adjustably inflatable retractors coupled to the tandem with fluid; and delivering the implant radiation dose suitable for the cancer treatment at the cancerous cervical treatment site in the patient, wherein each radiation lumen receives a respective radiation source positioned within each respective radiation lumen, and wherein each shielding lumen receives a respective wire of the at least one wire comprising the metal having an atomic number of greater than 70 positioned within each respective shielding lumen with the substantially synchronous movement relative to the respective radiation source to provide the radiation shielding in the direction of the tissue not intended for the radiation treatment.

13. The method of claim 12, wherein the metal comprises at least one of gold or tungsten.

14. A system for treating cervical and/or uterine cancers, the system comprising:

a tandem configured for insertion into a cervix of a patient;

an ovoid assembly configured to be coupled to the tandem via at least one groove on the tandem, the ovoid assembly comprising first and second inflatable ovoids and an ovoid support mechanism, wherein the ovoid assembly comprises first and second handles configured to support the respective first and second inflatable ovoids, wherein the handles are configured to allow for user manipulation to control the relative position of the ovoids with respect to each other, wherein the handles are configured to allow for user manipulation to control the relative position of the ovoids for insertion of the ovoids within the fornices of the patient, the first and second inflatable ovoids having a deflated configuration for insertion into the patient and one or more inflated configurations for positioning the ovoid assembly during treatment;

wherein the ovoid support mechanism is configured to establish a position of the ovoid assembly relative to the tandem based on a coupling of the ovoid support mechanism with the tandem assembly, wherein the tandem and the first and second inflatable ovoids are configured to be coupled to a radioactive source to deliver an implant radiation dose suitable for cancer treatment at a cancerous cervical and/or uterus treatment site in the patient, wherein at least one of the tandem and the first and second inflatable ovoids is configured as a multi-lumen component; and wherein each multi-lumen component has a radiation lumen configured to receive a radiation source positioned therein during treatment, and wherein each multi-lumen component also has a shielding lumen configured to receive a wire comprising a metal having an atomic number greater than 70 positioned therein during treatment with substantially synchronous movement relative to the radiation source to provide radiation shielding in a direction of tissue not intended for radiation treatment.

15. The system of claim 14, further comprising an optical fiber, wherein the optical fiber is configured for coupling to a camera to facilitate positioning of the tandem.

16. The system of claim 14, further comprising one or more wires comprising one or more metals having an atomic number of greater than 70, the one or more wires configured to reduce an amount of radiation passing therethrough.

17. The system of claim 14, wherein the metal comprises at least one of gold or tungsten.

18. The system of claim 14, wherein the tandem comprises a multi-lumen configuration.

19. The system of claim 14, wherein at least one of the ovoids comprises a multi-lumen configuration.

20. The system of claim 14, wherein the tandem comprises a multi-lumen configuration with at least one lumen configured to link to an optical fiber positioned therethrough.

21. The system of claim 14, comprising first and second inflatable retractors configured to be releasably coupled to the ovoid assembly, the first and second inflatable retractors having a deflated configuration for insertion into the patient and an inflated configuration for retraction of tissue during treatment.

* * * * *